(12) United States Patent
Barraud et al.

(10) Patent No.: US 9,156,855 B2
(45) Date of Patent: Oct. 13, 2015

(54) REGULATION OF NITRIC OXIDE RELEASE AND BIOFILM DEVELOPMENT

(75) Inventors: Nicolas Barraud, New South Wales (AU); Bharat Gangadhar Kardak, Maharashtra (IN); Michael John Kelso, New South Wales (AU); Staffan Kjelleberg, New South Wales (AU); Scott Rice, New South Wales (AU)

(73) Assignees: Newsouth Innovation Pty Limited, Sydney, NSW (AU); University of Wollongong, Wollongong, NSW (AU)

( * ) Notice: Subject to any disclaimer, the term of this patent is extended or adjusted under 35 U.S.C. 154(b) by 29 days.

(21) Appl. No.: 14/117,742

(22) PCT Filed: May 16, 2012

(86) PCT No.: PCT/AU2012/000542
§ 371 (c)(1),
(2), (4) Date: Apr. 10, 2014

(87) PCT Pub. No.: WO2012/155203
PCT Pub. Date: Nov. 22, 2012

(65) Prior Publication Data
US 2014/0221331 A1     Aug. 7, 2014

(30) Foreign Application Priority Data

May 16, 2011   (AU) ................ 2011901872

(51) Int. Cl.
| | | |
|---|---|---|
| *C07D 501/42* | (2006.01) |
| *C07D 501/54* | (2006.01) |
| *C07D 501/56* | (2006.01) |
| *A01N 51/00* | (2006.01) |
| *A61K 31/545* | (2006.01) |
| *A61K 31/546* | (2006.01) |
| *C07D 501/46* | (2006.01) |
| *C07D 501/30* | (2006.01) |
| *C07D 501/34* | (2006.01) |
| *C07D 503/18* | (2006.01) |

(52) U.S. Cl.
CPC .............. *C07D 501/46* (2013.01); *A01N 51/00* (2013.01); *A61K 31/545* (2013.01); *A61K 31/546* (2013.01); *C07D 501/30* (2013.01); *C07D 501/34* (2013.01); *C07D 501/42* (2013.01); *C07D 501/54* (2013.01); *C07D 501/56* (2013.01); *C07D 503/18* (2013.01)

(58) Field of Classification Search
CPC .. C07D 501/42; C07D 501/54; C07D 501/56; A01N 51/00; A61K 31/545; A61K 31/546
See application file for complete search history.

(56) References Cited

U.S. PATENT DOCUMENTS

2009/0131342 A1 *  5/2009  Ellis ................................ 514/29

FOREIGN PATENT DOCUMENTS

| CN | 101213292 | 7/2008 |
|---|---|---|
| DE | 10 2007 035 323 A1 | 1/2009 |
| WO | WO 2006/081619 | 8/2006 |
| WO | WO 2006/125262 A1 | 11/2006 |
| WO | WO 2009/049208 A1 | 4/2009 |
| WO | WO 2009/124379 | 10/2009 |

OTHER PUBLICATIONS

Barraud et al., "Nitric oxide-mediated dispersal in single- and multi-species biofilms of clinically and industrially relevant microorganisms," Biotechnology, 2(3):370-376 (2009).

* cited by examiner

*Primary Examiner* — Robert Havlin
(74) *Attorney, Agent, or Firm* — Fanelli Haag PLLC

(57) ABSTRACT

The present invention relates generally to methods and compounds for regulating the release of nitric oxide in the vicinity of biofilm-forming microorganisms to regulate programmed cell death in the microorganisms and thereby promote dispersal of microorganism from biofilms and/or inhibit biofilm formation or development. More particularly, the invention relates to the use of compounds to provide spatial and temporal control over nitric oxide release.

18 Claims, 7 Drawing Sheets

REGULATION OF NITRIC OXIDE RELEASE AND BIOFILM DEVELOPMENT

FIELD OF THE INVENTION

This application is a U.S. National Stage Application of PCT international Patent Application No. PCT/AU2012/00542, which was filed on May 16, 2012 which claims priority to Australian Patent Application No. 2011901872 filed May 16, 2011.

The present invention relates generally to methods and compounds for regulating the release of nitric oxide in the vicinity of biofilm-forming microorganisms to regulate programmed cell death in the microorganisms and thereby promote dispersal of microorganism from biofilms and/or inhibit biofilm formation or development. More particularly, the invention relates to the use of compounds to provide spatial and temporal control over nitric oxide release.

BACKGROUND OF THE INVENTION

Biofilms are three dimensional microbial growth forms comprising microbial communities and the extracellular matrix they produce. Biofilms are ubiquitous in nature, forming on any surface or at any interface where water or suitable fluid is available, or in suspension, for example as flocs or granules.

Biofilms are etiologic agents of a number of diseases and are associated with a variety of chronic infections in humans, forming on a variety of surfaces within the body, for example on surfaces in the respiratory tract and lungs (associated with cystic fibrosis and Legionnaire's disease), on surfaces of the ear (associated with otitis media), and on surfaces of the heart and heart valves (associated with bacterial endocarditis). Biofilms offer increased protection to the microorganism inhabitants, for example in the form of substantially increased resistance to antibiotics compared to planktonic cells and resistance to phagocytosis, which render biofilms very difficult to eradicate and explains the severity and high level of persistence of biofilms and the morbidity associated with infections produced by biofilms. In the case of cystic fibrosis, for example, a principal cause of respiratory infections is *Pseudomonas aeruginosa*, and *P. aeruginosa* biofilms on the surface of the lungs in cystic fibrosis sufferers imparts a greater degree of antibiotic resistance and resistance to host immune defences. Consequently the major cause of chronic lung infections, and in turn of morbidity and mortality, in cystic fibrosis sufferers is biofilm-associated *P. aeruginosa*.

Biofilms also readily form on medical equipment such as catheters and cannulas, and on implantable medical devices including stents and contact lenses. Indeed many long term catheterization patients acquire infections caused by biofilm-forming bacteria, and more generally biofilms are responsible for a range of hospital acquired infections, adding considerable cost to health systems.

From a public health perspective, biofilms are important reservoirs of pathogens in water systems such as drinking water, reservoirs, pipes and air-conditioning ducts. Biofilms also cause significant industrial damage, causing, for example, fouling and corrosion in fluid processes such as water distribution and treatment systems, pulp and paper manufacturing systems, heat exchange systems and cooling towers, and contributing to the souring of oil in pipelines and reservoirs.

Biofilms are essentially multicellular microbial communities, the formation and development of which are dependent on various multicellular traits of the member organisms, such as cell-cell signalling. Extracellular signalling systems such as quorum sensing are used by bacteria to assess cell density and initiate changes in gene expression and phenotypes when sufficient concentrations of signalling molecules are reached. This is associated with differential gene expression, leading to the induction of, for example, virulence factors and/or defence mechanisms, and with cell differentiation such that biofilm-associated cells become highly differentiated from planktonic cells.

As the cells within biofilms differentiate and biofilms mature, reduced metabolic rates, the cellular expression of defence mechanisms and the reduced ability of antimicrobial agents to penetrate the biofilm results in increased antimicrobial resistance and make biofilms particularly difficult to eradicate. Present biofilm control strategies typically target the early stages of biofilm development and involve the use of toxic antimicrobial agents. However such toxic agents can present their own downstream problems, for example when used industrially due to their release into the environment. Improved strategies for biofilm control are clearly required.

Studies of *P. aeruginosa*, as well as other model biofilm forming bacteria, mixed species oral biofilms, and mixed species granular biofilms in waste water treatment processes have shown that programmed cell death induces detachment and dispersal of cells from biofilms (see, for example, Hope et al., 2002 and Webb et al, 2003) and is a general feature of biofilm development. Inventors of the present invention have previously found that programmed cell death in biofilms is linked to the accumulation of reactive oxygen and nitrogen species (RONS) within biofilm-forming organisms, and that programmed cell death and dispersal of cells from a biofilm into planktonic cells can be induced using low, non-toxic concentrations of nitric oxide generators or donors (see co-pending WO 2006/125262, the disclosure of which is incorporated herein by reference in its entirety).

The exploitation of this finding offers the prospect of novel technologies for the removal of biofilms in a broad range of environments and settings, including medical, industrial and bioprocessing by exposing biofilms to nitric oxide to induce the dispersal of cells. However in some settings, in particular in human health and medical applications, the uncontrolled and widespread release of nitric oxide may be associated with unacceptable side effects and toxicity levels. Improving the stability of nitric oxide donors in solution also poses a challenge. Accordingly, there is a need for the development of effective mechanisms to regulate, spatially and/or temporally, the release of nitric oxide such that this release can be localised in the vicinity of a biofilm to thereby minimise side effects and toxicity at other locations.

Now provided herein are compounds, methods and compositions for regulating the release of nitric oxide temporally and spatially and in turn providing novel mechanisms for promoting dispersal of cells from biofilms and regulating biofilm development.

SUMMARY OF THE INVENTION

In a first aspect the present invention provides a compound of the formula (I), or a salt thereof:

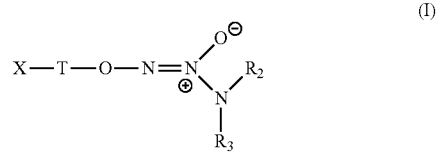

wherein T is a bond or a linker, $R_2$ and $R_3$ are organic residues and X is selected from the group consisting of:

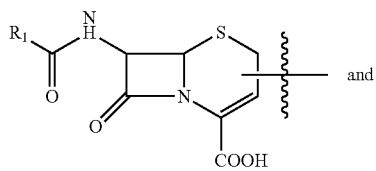

and

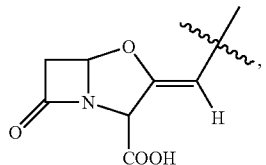

wherein $R_1$ is an organic residue.

In one embodiment, the compound of the formula (I) has the following structure:

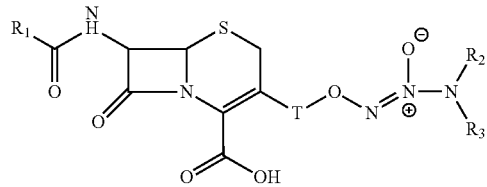

wherein $R_1$, $R_2$, $R_3$ and T are as defined above.

T may be a linker which is a bivalent hydrocarbon having between 1 and 6 carbon atoms, for example —$CH_2$—, —$CH_2CH_2$—, —$CH_2CH_2CH_2$—, —$CH(CH_3)CH_2$— or —$CH_2CH_2CH_2CH_2$—. In one embodiment T is $CH_2$.

$R_1$ may be a substituent that corresponds to a substituent attached to the 7-NHC(O)— group of a cephalosporin antibiotic.

In one embodiment, $R_1$ is Y-aryl or Y-heteroaryl and Y is a bivalent hydrocarbon having between 1 and 4 carbon atoms. The aryl group may be selected from: phenyl, biphenyl, naphthyl, anthracenyl and phenanthrenyl, and the heteroaryl group may be a 5- or 6-membered ring wherein between 1 and 4 carbon atoms are replaced with nitrogen and/or sulfur atoms.

The heteroaryl group may be selected from: thienyl, tetrazolyl, imidazolyl, triazolyl and pyrrolyl.

In one embodiment, $R_1$ is selected from the group consisting of —$CH_2$-phenyl, —$CH_2$-thienyl and —$CH_2$-tetrazolyl.

$R_2$ and $R_3$ may be independently selected from the group consisting of: $C_1$-$C_{10}$ alkyl, or alternatively $R_2$ and $R_3$ together with the nitrogen to which they are attached may form a 5- or 6-membered ring which may optionally contain between 1 and 3 additional nitrogen atoms, and which may optionally be substituted with an aryl or heteroaryl group.

In an alternative embodiment $R_2$ and $R_3$ are independently selected from $C_1$-$C_6$ alkyl, or alternatively $R_2$ and $R_3$, together, with the nitrogen to which they are attached, form a saturated 5- or 6-membered ring which may optionally contain 1 additional nitrogen atom, and which may optionally be substituted with a substituent selected from the group consisting of: pyrimidinyl and phenyl.

In another embodiment $R_2$ and $R_3$ are independently selected from $C_1$-$C_6$ alkyl, or alternatively $R_2$ and $R_3$, together with the nitrogen to which they are attached, form a structure selected from the group consisting of:

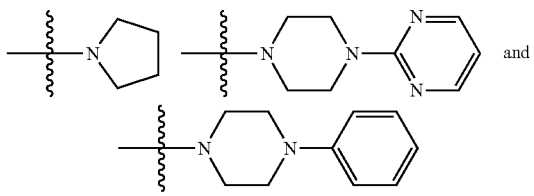

and

In one embodiment the compound of formula (I) has a structure selected from the group consisting of:

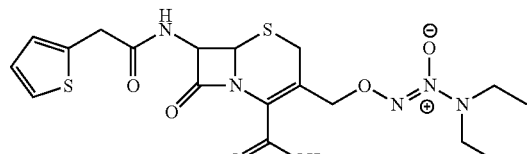

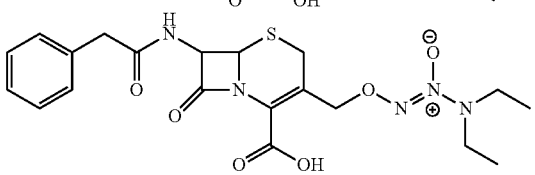

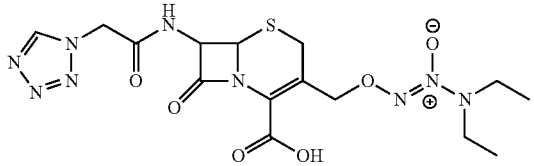

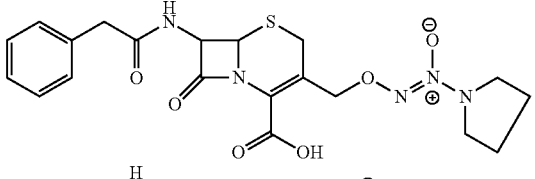

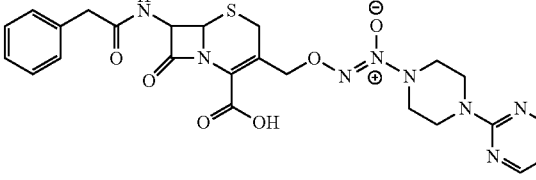

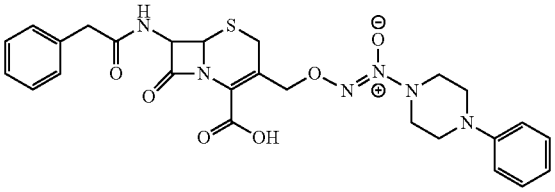

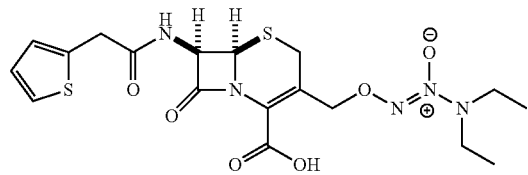

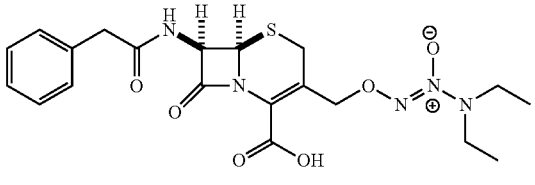

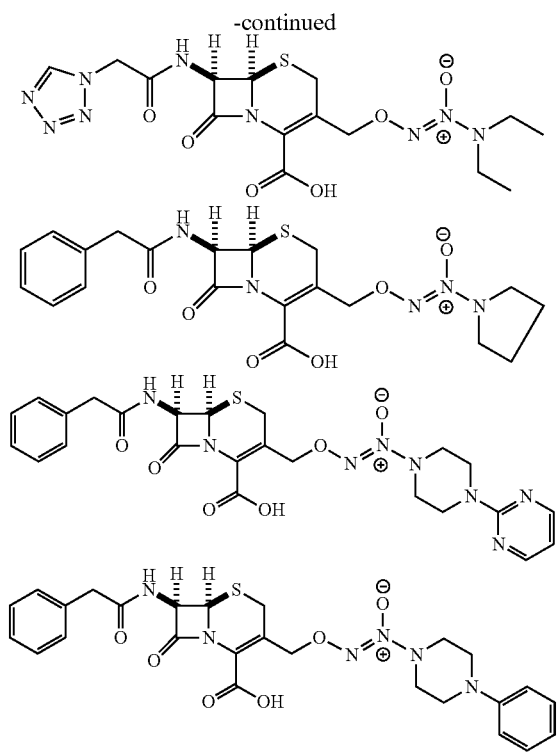

The compounds of formula (I) may further comprise an antibiotic compound which is attached via the $R_2$ and/or $R_3$ substituent. The antibiotic may be, for example, ciprofloxacin or N-desmethyl levofloxacin.

In a second aspect the invention provides a composition for promoting the dispersal of microorganisms from a biofilm or inhibiting the formation and/or development of biofilms, the composition comprising a compound according to the first aspect.

The composition may further comprise one or more additional antibiotics or antimicrobial agents. In exemplary embodiments the one or more additional antibiotics may be selected from ceftazidime, tobramycin and ciprofloxacin.

In a third aspect the invention provides a method for promoting dispersal of microorganisms from a biofilm, the method comprising exposing the biofilm to an effective amount of a compound of the first aspect or a composition of the second aspect.

In a fourth aspect the invention provides a method for inhibiting biofilm formation and/or development, the method comprising exposing biofilm-forming microorganisms to an effective amount of a compound of the first aspect or a composition of the second aspect.

In accordance with the fourth aspect, the compound or composition comprising the same may be coated, impregnated or otherwise contacted with a surface or interface susceptible to biofilm formation. In one embodiment the surface may be a surface of an implantable medical device, prosthesis or medical or surgical equipment.

In accordance with the methods of the third and fourth aspects the biofilm-containing or biofilm-forming microorganisms typically express a β-lactamase or a transpeptidase. The β-lactamase may be encoded chromosomally or extrachromosomally and expression may be constitutive or inducible. In particular embodiments the β-lactamase is a penicillinase. The biofilm or biofilm-forming microorganisms may be exposed to a β-lactam antibiotic prior to or concomitant with exposure to the compound or composition. The β-lactam antibiotic may induce production of extracellular β-lactamase in said biofilm-forming microorganisms. The β-lactam antibiotic may be provided in a subinhibitory, bacteriostatic or bacteriocidal concentration. In particular embodiments the β-lactam antibiotic is imipenem.

In particular embodiments of the third and fourth aspects the biofilm may be on a bodily surface of a subject, internal or external to the subject, and exposure of the biofilm or biofilm-forming microorganisms to the compound or composition may be via administration of the compound or composition to the subject. Administration may be via any suitable route depending on the nature and location of the biofilm or biofilm-forming microorganisms.

Methods for promoting dispersal of or preventing formation of biofilms may comprise inducing differentiation events in microorganisms within biofilms which lead to dispersal or may comprise preventing induction of differentiation events in microorganisms which lead to biofilm formation. Alternatively, or in addition, methods may comprise increasing the sensitivity of a microorganism to antimicrobial agents.

In accordance with the above aspects and embodiments, the biofilm may be surface-associated or suspended. The suspended biofilm may be in the form of flocs or granules. Typically in accordance with the above aspects and embodiments the biofilm or biofilm-forming microorganisms are exposed to an effective amount of a compound or composition as defined here such that the concentration of the nitric oxide donor or nitric oxide released and thus exposed to the biofilm or microorganisms is non-toxic to the environment or to the subject in which the biofilm or microrganisms are found. For example, the concentration of nitric oxide may be in the nanomolar, micromolar or millimolar range. The nitric oxide concentration may be, for example, from about 1 nM to about 500 μM.

The microorganisms present in the biofilm may be of a single species or of multiple species. The microorganisms within the biofilm or capable of forming a biofilm may comprise one or more species selected from, for example, *Pseudomonas* spp., *Pseudoalieromonas* spp., *Staphylococcus* spp., *Streptococcus* spp., *Shigella* spp., *Mycobacterium* spp., *Enterococcus* spp., *Escherichia* spp., *Salmonella* spp., *Legionella* spp., *Haemophilus* spp., *Bacillus* spp., *Desulfovibrio* spp., *Shewanella* spp., *Geobacter* spp., *Klebsiella* spp., *Proteus* spp., *Aeromonas* spp., *Arthrobacter* spp., *Micrococcus* spp., *Burkholderia* spp., *Serratia* spp., *Porphyromonas* spp., *Fusobacterium* spp. and *Vibrio* spp. In particular embodiments the microorganism may be *Pseudomonas aeruginosa*, *Staphylococcus epidermidis*, *Staphylococcus aureus*, *Mycobacterium tuberculosis*, *Escherichia coli*, *Bacillus licheniformis*, *Burkholderia cenocepacia*, *Serratia marcescens*, *Fusobacterium nucleatum*, or *Vibrio cholerae*.

In particular embodiments the biofilm is on or within the body of a subject and may be associated with a disease or disorder suffered by the subject. The disease or disorder may be, for example, cystic fibrosis, bacterial endocarditis, otitis media, Legionnaire's disease, tuberculosis or kidney stones.

Accordingly, in a fifth aspect there is provided a method for treating or preventing a biofilm-associated infection, disease or disorder in a subject wherein the infection is caused by a microorganism capable of forming a biofilm, the method comprising administering to the subject an effective amount of a compound of the first aspect or a composition of the second aspect.

The present invention also provides the use of a compound of the first aspect for the manufacture of a composition for use in promoting dispersal of microorganisms from a biofilm or for inhibiting the formation or development of a biofilm.

The present invention also provides the use of a compound of the first aspect for the manufacture of a medicament for treating or preventing a biofilm-associated infection, disease or disorder in a subject wherein the infection is caused by a microorganism capable of forming a biofilm.

BRIEF DESCRIPTION OF THE DRAWINGS

Embodiments of the invention are described herein, by way of non-limiting example only, with reference to the following drawings.

DETAILED DESCRIPTION

Figure 1:
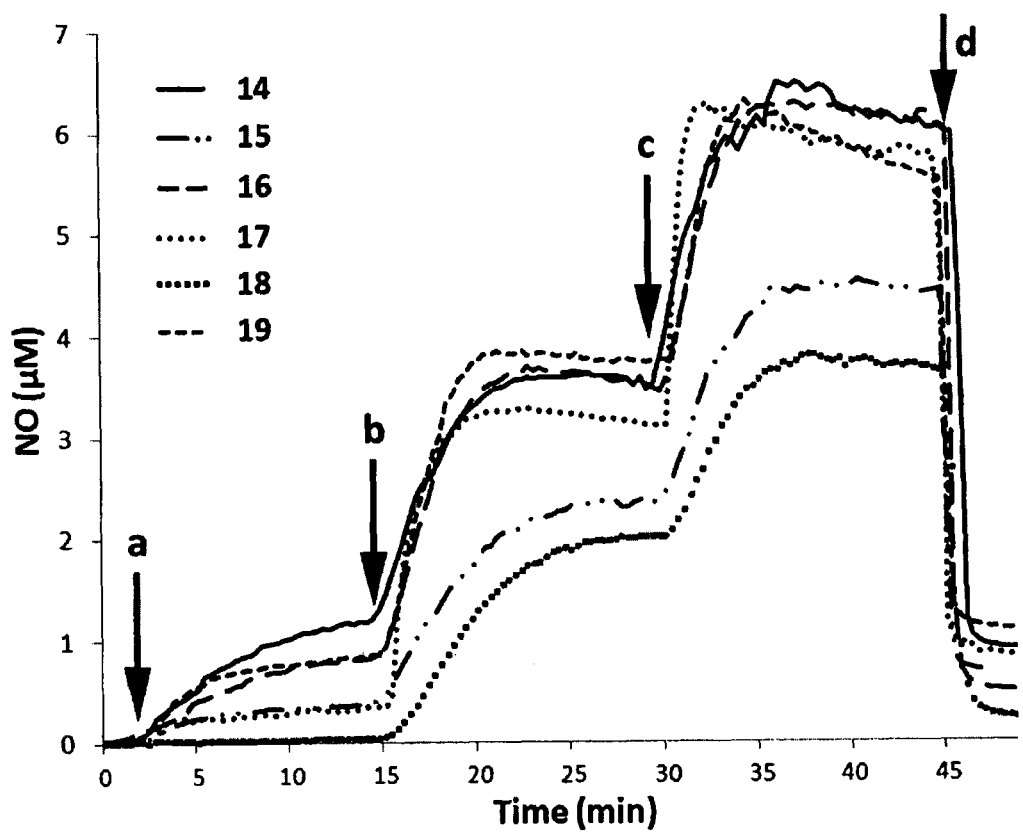
FIG. 1. Amperometric characterization of nitric oxide release from cephalosporin-3'-diazeniumdiolate free acids (Compounds 14 to 19). Arrows indicate addition of the following to a reaction vial containing 10 mL Tris buffer at pH 7.0: (a) 10 μL of 100 mM cephalosporin-3'-diazeniumdiolate, (b) 10 μl 1 U/μl penicillinase, (c) 20 μl 1 U/μl penicillinase, (d) 80 μL of 10 mM free radical scavenger PTIO.

The articles "a" and "an" are used herein to refer to one or to more than one (i.e., to at least one) of the grammatical object of the article. By way of example, "an element" means one element or more than one element.

In the context of this specification, the term "about" is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein the term "antimicrobial agent" refers to any agent that, alone or in combination with another agent such as an antibiotic, is capable of killing or inhibiting the growth of one or more species of microorganisms.

As used herein the term "biofilm" refers to any three-dimensional, matrix-encased microbial community displaying multicellular characteristics. Accordingly, as used herein, the term biofilm includes surface-associated biofilms as well as biofilms in suspension, such as flocs and granules. Biofilms may comprise a single microbial species or may be mixed species complexes, and may include bacteria as well as fungi, algae, protozoa, or other microorganisms.

The term "biofilm-forming microorganism" refers to any microorganism that is capable of forming biofilms, either single species or mixed species biofilms.

As used herein the term "dispersal" as it relates to a biofilm and microorganisms making up a biofilm means the process of detachment and separation of cells and a return to a planktonic phenotype or behaviour of the dispersing cells.

As used herein the term "effective amount" includes within its meaning a non-toxic but sufficient amount of an agent to provide the desired effect. The exact amount required will vary from subject to subject depending on factors such as the species of microorganisms being treated, the extent, severity and/or age of the biofilm being treated, whether the biofilm is surface-associated or suspended, the particular agent(s) being administered and the mode of administration and so forth. Thus, it is not possible to specify an exact "effective amount". However, for any given case, an appropriate "effective amount" may be determined by one of ordinary skill in the art using only routine experimentation.

As used herein the term "exposing" means generally bringing into contact with. Typically direct exposure refers to administration of the agent to the microorganism or biofilm to be treated or otherwise bringing the microorganism or biofilm into contact with the agent itself. Typically indirect exposure refers to the administration of a precursor of the active agent or a compound or molecule capable of generating, either solely or in reaction with other compounds or molecules, the active agent to the microorganism or biofilm or otherwise bringing the microorganism or biofilm into contact therewith. Thus, a microorganism or biofilm may be exposed to compound or composition as defined herein directly or indirectly. Further, a microorganism or biofilm may be exposed to nitric oxide released from a compound directly or indirectly. In the context of the present disclosure, indirectly "exposing" a biofilm or microorganisms to a compound or composition as defined herein also includes the administration of the compound or composition to a subject in or on which the biofilm or microorganisms reside. Thus, in the present disclosure the terms "exposing", "administering" and "delivering" and variations thereof may, in some contexts, be used interchangeably.

The term "inhibiting" and variations thereof such as "inhibition" and "inhibits" as used herein in relation to biofilms means complete or partial inhibition of biofilm formation and/or development and also includes within its scope the reversal of biofilm development or processes associated with biofilm formation and/or development. Further, inhibition may be permanent or temporary. The inhibition may be to an extent (in magnitude and/or spatially), and/or for a time, sufficient to produce the desired effect. Inhibition may be prevention, retardation, reduction or otherwise hindrance of biofilm formation or development. Such inhibition may be in magnitude and/or be temporal or spatial in nature. Further, such inhibition may be direct or indirect. By indirect inhibition is meant that the agent may effect the expression or activity of molecules which in turn regulate biofilm formation or development.

As used herein the term "programmed cell death" means a developmental event within a biofilm that occurs at defined stages and causes autolysis, cellular differentiation and the development of subpopulations of cells with specific phenotypes.

Similarly, the term "promoting" and variations thereof such as "promotion" and "promotes" as used herein in the context of promoting the dispersal of microorganisms from a biofilm also complete or partial promotion of dispersal, which may be permanent or temporary, to an extent (in magnitude and/or spatially), and/or for a time, sufficient to produce the desired effect. Such promotion may be direct or indirect.

As used herein the term "surface" includes both biological surfaces and non-biological surfaces. Biological surfaces typically include surfaces both internal (such as organs, tissues, cells, bones and membranes) and external (such as skin, hair, epidermal appendages, seeds, plant foliage) to an organism. Biological surfaces also include other natural surfaces such as wood or fibre. A non-biological surface may be any artificial surface of any composition that supports the establishment and development of a biofilm. Such surfaces may be present in industrial plants and equipment, and include medical and surgical equipment and medical devices, both implantable and non-implantable. Further, for the purposes of the present disclosure, a surface may be porous (such as a membrane) or non-porous, and may be rigid or flexible.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery.

In the context of this specification, the term "$C_1$-$C_{20}$ alkyl" is taken to include straight chain and branched chain monovalent saturated hydrocarbon groups having 1 to 20 carbon atoms, such as methyl, ethyl, propyl, isopropyl, butyl, isobutyl, secbutyl, tertiary butyl, pentyl, hexyl, heptyl, octyl, nonyl, decyl, undecyl, dodecyl and the like.

In the context of this specification, the term "$C_1$-$C_{10}$ alkyl" is taken to include straight chain and branched chain monovalent saturated hydrocarbon groups having 1 to 10 carbon atoms, such as methyl, ethyl, propyl, isopropyl, butyl, isobutyl, secbutyl, tertiary butyl, pentyl, hexyl, heptyl, octyl and the like.

In the context of this specification, the term "$C_1$-$C_6$ alkyl" is taken to include straight chain and branched chain monovalent saturated hydrocarbon groups having 1 to 6 carbon atoms, such as methyl, ethyl, propyl, isopropyl, butyl, isobutyl and the like.

In the context of this specification, the term "$C_2$-$C_{20}$ alkenyl" is taken to include straight chain and branched chain monovalent hydrocarbon radicals having 2 to 20 carbon atoms and at least one carbon-carbon double bond, such as vinyl, propenyl, 2-methyl-2-propenyl, butenyl, pentenyl, hexenyl, heptenyl, undecenyl and the like.

In the context of this specification, the term "$C_2$-$C_{10}$ alkenyl" is taken to include straight chain and branched chain monovalent hydrocarbon radicals having 2 to 10 carbon atoms and at least one carbon-carbon double bond, such as vinyl, propenyl, 2-methyl-2-propenyl, butenyl, pentenyl and the like.

In the context of this specification, the term "$C_2$-$C_6$ alkenyl" is taken to include straight chain, and branched chain monovalent hydrocarbon radicals having 2 to 6 carbon atoms and at least one carbon-carbon double bond, such as vinyl, propenyl, 2-methyl-2-propenyl and the like.

In the context of this specification, the term "$C_2$-$C_{20}$ alkynyl" is taken to include straight chain and branched chain monovalent hydrocarbon radicals having 2 to 20 carbon atoms and at least one carbon-carbon triple bond, such as ethynyl, propynyl, butynyl, pentynyl, hexynyl, undecynyl and the like.

In the context of this specification, the term "$C_2$-$C_{10}$ alkynyl" is taken to include straight chain and branched chain monovalent hydrocarbon radicals having 2 to 10 carbon atoms and at least one carbon-carbon triple bond, such as ethynyl, propynyl, butynyl, pentynyl, hexynyl and the like.

In the context of this specification, the term "$C_2$-$C_6$ alkynyl" is taken to include straight chain and branched chain monovalent hydrocarbon radicals having 2 to 6 carbon atoms and at least one carbon-carbon triple bond, such as ethynyl, propynyl, butynyl and the like.

In the context of this specification, the term "aryl" is taken to include monovalent aromatic radicals having between 6 and 30 carbon atoms, for example phenyl, biphenyl, naphthyl, anthracenyl, phenanthrenyl and the like.

In the context of this specification, the term "heteroaryl" is taken to include monovalent aromatic radicals having between 4 and 25 atoms, wherein 1 to 6, or 1 to 5, or 1 to 4, or 1 to 3, or 1 or 2 atoms are heteroatoms selected from nitrogen, oxygen and sulfur, for example furanyl, quinazolinyl, quinolinyl, isoquinolinyl, indolyl, isoindolyl, benzopyranyl, benzooxazolyl, benzimidazolyl, pyrazolyl, tetrazolyl, oxazolyl, oxadiazolyl, isoxazolyl, thiadiazolyl, quinolizinyl, pyranyl, isothiazolyl, thiazolyl, thienyl, imidazolyl, pyrazinyl, pyridazinyl, pyrimidinyl, isothiazolyl, pyridyl, triazolyl, benzothienyl, pyrrolyl, benzothiazolyl, quinoxalinyl, naphthyridinyl, pteridinyl, carbazolyl, azepinyl, acridinyl, benzisothiazolyl, benzoxazolyl, benzisoxazolyl, benzofuryl, purinyl, benzimidazolyl, triazinyl and the like.

In the context of this specification, the terms "halo" and "halogen" may be used interchangeably and are taken to include fluoro, chloro, bromo and iodo.

In the context of this specification, the term "$C_3$-$C_7$ cycloalkyl" is taken to include cyclic alkyl groups having between 3 and 7 carbon atoms, for example cyclobutyl, cyclohexyl and the like.

In the context of this specification, the term "$C_5$-$C_7$ cycloalkyl" is taken to include cyclic alkyl groups having between 5 and 7 carbon atoms, for example cyclopentyl and the like.

In the context of this specification, the term "$C_3$-$C_7$ cycloalkenyl" is taken to include cyclic hydrocarbon groups having between 3 and 7 carbon atoms and at least one carbon-carbon double bond, for example cyclopropenyl, cyclopentenyl, cyclohexenyl and the like.

In the context of this specification, the term "$C_1$-$C_3$ alkylene" is taken to include bivalent hydrocarbon radicals having between 1 and 3 carbon atoms, for example methylene and ethylene.

β-lactamases are enzymes produced by bacteria in defence against β-lactam antibiotics. Many biofilm-forming microorganisms such as *Pseudomonas aeruginosa* are capable of producing β-lactamases and produce large quantities of these enzymes during biofilm formation and within biofilms, assisting to render β-lactam antibiotics ineffective in eradicating biofilms. As described and exemplified herein the present inventors have now found that the coupling of a β-lactam antibiotic or the β-lactam ring-containing core of a β-lactam antibiotic or antimicrobial agent to a nitric oxide donor compound enables the targeted delivery of effective concentrations of nitric oxide and the spatial and temporal control over nitric oxide release upon exposure to biofilms and biofilm-forming microorganisms to promote dispersal of microorganisms from biofilms. As exemplified herein the conjugate compounds of the present disclosure are stable in solution and effectively make nitric oxide available to microorganisms in biofilms, being demonstrated to induce the rapid dispersal of *P. aeruginosa* biofilms after only 10 minutes exposure at concentrations in the micromolar range.

Accordingly, provided herein are conjugate compounds, compositions comprising the same and uses thereof, wherein the conjugates comprise a β-lactam antibiotic or β-lactam ring-containing antimicrobial agent, or a derivative thereof, complexed with a nitric oxide donor compound. Such conjugates are stable in solution and act as nitric oxide prodrugs enabling the delivery of low, non-toxic concentrations of nitric oxide to desired sites to promote the dispersal of microorganisms from biofilms and inhibit the formation and/or development of biofilms.

In one aspect the present invention provides a compound of the formula (I), or a salt thereof:

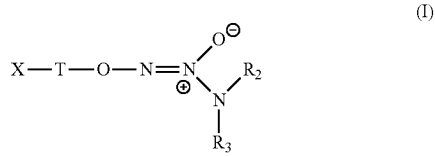

wherein T is a bond or a linker, $R_2$ and $R_3$ are organic residues and X is selected from the group consisting of:

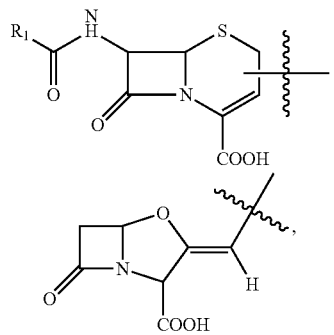

wherein $R_1$ is an organic residue.

The compounds of formula (I) may have one or more chiral centres. The present invention includes all enantiomers and diastereoisomers, as well as mixtures thereof in any proportions. The invention also extends to isolated enantiomers or pairs of enantiomers. In embodiments of the invention X is selected from the group consisting of:

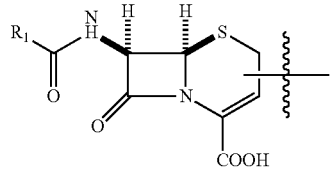

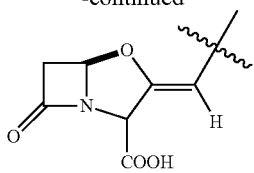

Also within the scope of the compounds of formula (I) are salts, including pharmaceutically acceptable salts. Salts of the compounds of formula (I) may be prepared by conventional methods known to those skilled in the art. For example, base-addition salts may be prepared by reacting the compounds of formula (I) with a suitable base. Examples of such salts include alkali metal salts, such as lithium, potassium and sodium, and alkali earth metal salts, such as calcium, magnesium and barium. Additional basic salts include, but are not limited to, ammonium, copper, iron, manganese and zinc salts. Acid addition salts may be prepared by reacting the compounds of formula (I) with organic or inorganic acids. Examples of such salts include HCl, HBr and HI salts, salts of other mineral acids such as sulfate, nitrate, phosphate and the like, alkyl and monoarylsulfonates such as ethanesulfonate, toluenesulfonate and benzene sulfonate, and salts of other organic acids, such as acetate, trifluoroacetate, tartrate, maleate, citrate, benzoate, ascorbate and the like. Compounds of the formula (I) may also be quaternised by reaction with compounds such as $(C_1-C_4)$alkyl halides, for example, methyl, ethyl, isopropyl and butyl halides.

T may be a bivalent linker having between 1 and 20 carbon atoms. In one embodiment, T is a bivalent hydrocarbon linker having between 1 and 20 carbon atoms, 1 and 15 carbon atoms, or between 1 and 10 carbon atoms. In another embodiment, T is selected from the group consisting of: —$CH_2$—, —$CH_2CH_2$—, —$CH(CH_3)CH_2$—, —$CH_2CH_2CH_2$— and —$CH_2CH_2CH_2CH_2$—.

$R_1$ may be a substituent corresponding to a substituent attached to the 7-NHC(O)— group of a cephalosporin antibiotic. For example, $R_1$ may be a substituent corresponding to a substituent attached to the 7-NHC(O)— group of any of the following: i, cephaloram, cefazolin, cefacetrile, cefadroxil, cefalexin, cefaloglycin, cefalonium, cefaloridine, cefalotin, cefapirin, cefatrizine, cefazedone, cefazaflur, cefradine, cefroxidine, ceftezole, cefachlor, cefatnandole, cefininox, cefonicid, ceforanide, cefotiam, cefprozil, cefbuperazone, cefuroxime, cefuzonam, cephamycin, cefotetan, cefmetazole, flomoxef, cefixime, ceftriaxone, ceftazidine, cefoperazone, cefcapene, cefdaloxime, cefdinir, cefditoran, cefetamet, cefmenoxime, cefodizime, cefotaxime, cefpimizole, cefpirimide, cefpodoxime, cefsulodin, cefteram, ceftibuten, ceftiolene, ceftizoxime, latamoxef, cefepine, cefozopram, cefpirome, cefquinome, ceftobiprole, ceftaroline fossamil and ceftiofur. It is to be noted that $R_1$ may be a substituent corresponding to a substituent attached to the 7-NHC(O)— group of any clinically useful cephalosporin antibiotic.

In one embodiment $R_1$ is selected from the group consisting of

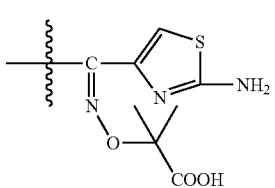

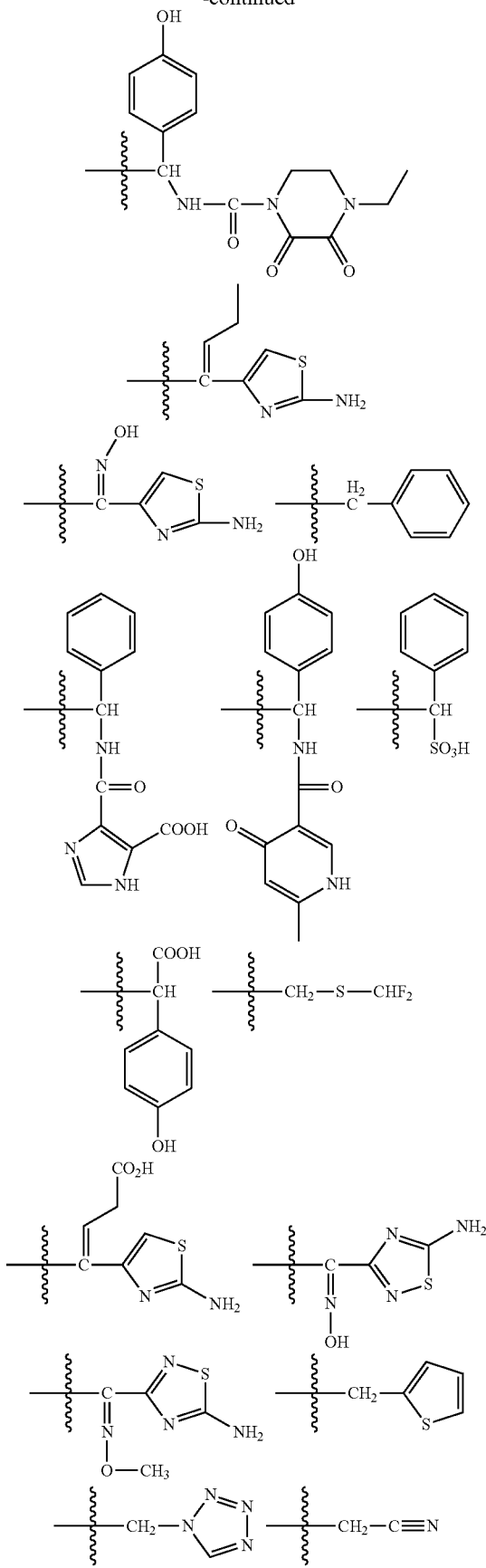

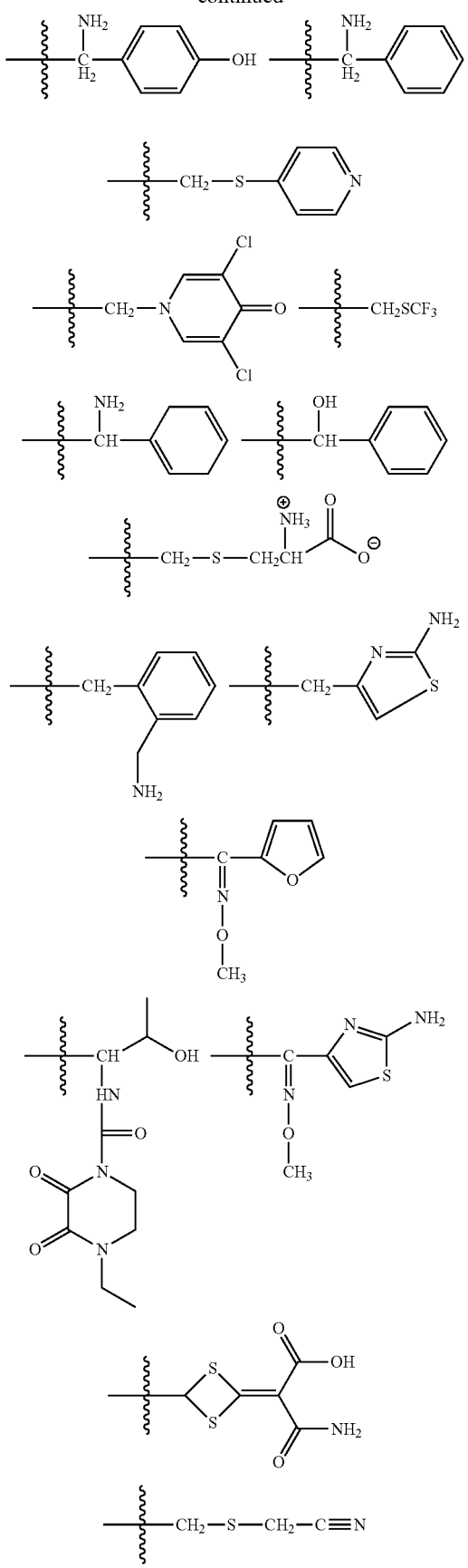

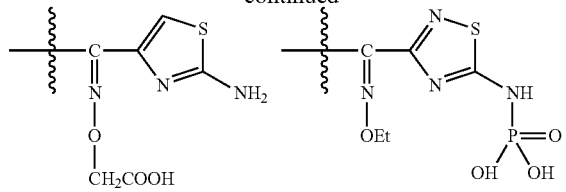

The above noted groups correspond to the substituents attached to the 7-NHC(O)— group of the specific cephalosporin antibiotics recited above.

In an alternative embodiment, $R_1$ is of the formula —Y-aryl, wherein Y is a bivalent hydrocarbon having between 1 and 6 carbon atoms. In one embodiment, Y is a straight chain or branched chain hydrocarbon having between 1 and 4 carbon atoms and aryl is phenyl or naphthyl.

In another embodiment, $R_1$ is Y-aryl or Y-heteroaryl where Y is a bivalent hydrocarbon having 1 to 4 carbon atoms and aryl and heteroaryl are optionally substituted.

In a further embodiment, $R_1$ is Y-aryl or Y-heteroaryl where Y is a bivalent hydrocarbon having 1 to 4 carbon atoms, and the aryl group is selected from: phenyl, biphenyl, naphthyl, anthracenyl and phenanthrenyl, and the heteroaryl group is a 5- or 6-membered ring wherein between 1 and 4 carbon atoms are replaced with nitrogen and/or sulfur atoms, and wherein the aryl and heteroaryl groups may optionally be substituted with one or more substituents selected from: $C_{1-6}$ alkyl, halo, amino, hydroxyl, methoxy and ethoxy.

In a further embodiment, $R_1$ is Y-aryl or Y-heteroaryl where Y is a bivalent hydrocarbon having 1 to 4 carbon atoms, and the aryl group is selected from: phenyl, biphenyl, naphthyl, anthracenyl and phenanthrenyl, and the heteroaryl group is a 5- or 6-membered ring wherein between 1 and 4 carbon atoms are replaced with nitrogen and/or sulfur atoms.

In a further embodiment, $R_1$ is Y-aryl or Y-heteroaryl where Y is a bivalent hydrocarbon having 1 to 3 carbon atoms, and the aryl group is selected from: phenyl, biphenyl and naphthyl, and the heteroaryl group is selected from thienyl, tetrazolyl, imidazolyl, triazolyl, thiazolyl, isothiazolyl and pyrrolyl.

In a further embodiment, $R_1$ is Y-aryl or Y-heteroaryl where Y is a bivalent hydrocarbon having 1 or 2 carbon atoms, and the aryl group is selected from: phenyl, biphenyl and naphthyl, and the heteroaryl group is selected from thienyl, tetrazolyl, imidazolyl, triazolyl, thiazolyl, isothiazolyl and pyrrolyl.

In a further embodiment, $R_1$ is Y-aryl or Y-heteroaryl where Y is —$CH_2$—, and the aryl group is selected from: phenyl, biphenyl and naphthyl, and the heteroaryl group is selected from thienyl, tetrazolyl, imidazolyl, triazolyl, thiazolyl, isothiazolyl and pyrrolyl.

In one embodiment, $R_1$ is selected from the group consisting of: —$CH_2$-phenyl, —$CH_2$-thienyl and —$CH_2$-tetrazolyl.

$R_2$ and $R_3$ may independently be selected from: hydrogen, $C_3$-$C_7$ cycloalkyl, $C_3$-$C_7$ cycloalkenyl, $(CH_2)_p OC(O)PhOC(O)C_1$-$C_6$alkyl, $(CH_2)_p OC(O)APhC_1$-$C_6$alkyl, branched or straight chain $C_1$-$C_{20}$ alkyl, branched or straight chain $C_2$-$C_{20}$ alkenyl, branched or straight chain $C_2$-$C_{20}$ alkynyl, wherein the alkyl, alkenyl or alkynyl chains may optionally be interrupted by one or more groups/heteroatoms selected from O, S, NH, $NH_2^+$, and wherein the alkyl, alkenyl or alkynyl groups may optionally be substituted by one or more substituents selected from the group consisting of: halogen, cyano, COOH, $(CH_2)_p C(O)OC_1$-$C_6$alkyl, $C(O)OC_1$-$C_6$alkenyl, $SO_3H$, $SO_2$halogen, $SO_2NH_2$, $NH_2$, $NH_3^+$, OH, SH, $OC_1$-

$C_6$alkyl, $OC_2$-$C_6$alkenyl, $OC_2$-$C_6$alkynyl, aryl and heteroaryl, or alternatively $R_2$ and $R_3$, together with the nitrogen to which they are attached, form a 4-, 5-, 6-, 7- or 8-membered ring which may optionally contain 1, 2, 3, 4, 5 or 6 additional nitrogen atoms and may be saturated, unsaturated or partially unsaturated, and wherein the 4-, 5-, 6-, 7- or 8-membered ring may optionally be substituted by one or more substituents selected from the group consisting of: —C(O)$C_1$-$C_3$alkylenenaphthyl-O$C_1$-$C_6$alkyl, —C(O)$C_1$-$C_3$alkylene-Ph-C(O)-Ph, —C(O)$CH_2$O$(CH_2)_p$O$CH_3$, —C(O)OPhNO$_2$, —C(O)OPhNH$_2$, —C(O)O$(CH_2)_p$Chalogen$_3$, —C(O)O($CH_2$O$)_p$CH$_3$, $C_1$-$C_6$-alkyl, $C_2$-$C_6$alkenyl, $C_2$-$C_6$alkynyl, —C(O)$C_1$-$C_6$alkyleneCOO$C_1$-$C_6$alkyl, —C(O)$C_1$-$C_3$alkylenePh$C_1$-$C_6$alkyl, —C(O)O-pyrrolidinyl-2,5-dione, —C(O)$C_1$-$C_3$alkylenePh$C_1$-$C_6$alkyl, —C(O)($CH_2)_p$O$C_1$-$C_6$alkyl, —C(O)O$(CH_2)_p$halogen, —C(O)O$(CH_2)_p$Ph, —$(CH_2)_p$SH, —SO$_2$naphthyl-N$C_1$-$C_6$alkyl, —C(O)ON$C_1$-$C_6$alkyl, —$(CH_2)_p$OH, —C(O)PhOAc, —C(O)$(CH_2)_p$NHC(O)$C_1$-$C_6$alkyl, —C(O)NH$_2$, —C(O)M, —C(O)N$R_4R_5$, —$(CH_2)_p$CH(OH)CHOH, halogen, cyano, —COOH, —C(O)O$(CH_2)_p$Ph, —C(O)O$C_1$-$C_6$alkyl, —C(O)O$C_2$-$C_6$alkenyl, —C(O)O$C_2$-$C_6$alkynyl, —C(O)S$C_1$-$C_6$alkyl, —C(O)S$C_2$-$C_6$alkenyl, —C(O)S$C_2$-$C_6$alkynyl, —C(O)$C_1$-$C_6$alkyl, SO$_3$H, SO$_2$halogen, SO$_2$phenyl, SO$_2$NH$_2$, SO$_2$N$R_4R_5$, SO$_2$PhNHCO$C_1$-$C_6$alkyl, NH$_2$, OH, SH, O$C_1$-$C_6$alkyl, O$C_2$-$C_6$alkenyl, O$C_2$-$C_6$alkynyl, aryl and heteroaryl, and wherein A is a bivalent hydrocarbon radical having between 1 and 4 carbon atoms, p is a number between 0 and 4, $R_4$ and $R_5$ independently represent $C_1$-$C_6$alkyl and M is pyridyl, pyrimidinyl, pyrazinyl, phenyl or triazinyl.

In an alternative embodiment, $R_2$ and $R_3$ may independently be selected from: hydrogen, $C_5$-$C_7$ cycloalkyl, $(CH_2)_p$OC(O)PhOC(O)$C_1$-$C_6$alkyl, $(CH_2)_p$OC(O)APh$C_1$-$C_6$alkyl, branched or straight chain $C_1$-$C_{10}$ alkyl, branched or straight chain $C_2$-$C_{10}$ alkenyl and branched or straight chain $C_2$-$C_{10}$ alkynyl, wherein the alkyl, alkenyl or alkynyl chains may optionally be interrupted by between one and three groups/heteroatoms selected from O, S, NH and NH$_2^+$, and wherein the alkyl, alkenyl or alkynyl chains may optionally be substituted by between one and six substituents selected from the group consisting of: halogen, phenyl, ethoxy, methoxy, propoxy, COOH, $(CH_2)_p$COO$C_1$-$C_4$alkyl, NH$_2$, NH$_3^+$, OH and SH, and wherein A is a bivalent hydrocarbon radical having between 1 or 2 carbon atoms and p is 0, 1 or 2.

In another embodiment, $R_2$ and $R_3$ may independently be selected from: hydrogen, $C_5$-$C_7$ cycloalkyl, branched or straight chain $C_1$-$C_{10}$ alkyl, branched or straight chain $C_2$-$C_{10}$ alkenyl, branched or straight chain $C_2$-$C_{10}$ alkynyl, wherein the alkyl, alkenyl or alkynyl chains may optionally be interrupted by between one and three groups selected from O, NH and NH$_2^+$, and wherein the alkyl, alkenyl or alkynyl chains may optionally be substituted by between one and four substituents selected from the group consisting of: halogen, phenyl, methoxy, COOH, —CH$_2$COO$C_1$-$C_4$alkyl, NH$_2$ and NH$_3^+$.

In yet another embodiment, $R_2$ and $R_3$ may independently be selected from: hydrogen, cyclohexyl, branched or straight chain $C_1$-$C_{10}$ alkyl or branched or straight chain $C_2$-$C_{10}$ alkenyl, wherein the alkyl or alkenyl chains may optionally be interrupted by one or two groups selected from NH and NH$_2^+$, and wherein the alkyl, alkenyl or alkynyl chains may optionally be substituted by between one and three substituents selected from the group consisting of: phenyl, methoxy, COOH, NH$_2$ and NH$_3^+$.

In still a further embodiment, $R_2$ and $R_3$, together with the nitrogen to which they are attached, form a 4-, 5-, 6- or 7-membered ring which may optionally contain 1, 2, 3, 4 or 5 additional nitrogen atoms and may be saturated, unsaturated or partially unsaturated, and wherein the 4-, 5-, 6- or 7-membered ring may optionally be substituted by one or more substituents selected from the group consisting of: SO$_2$NMe$_2$, SO$_3$H, SO$_2$halogen, SO$_2$NH$_2$, —C(O)O(CH$_2)_p$Ph, —C(O)Me, —C(O)pyridyl, —(CH$_2)_p$OH, —C(O)NH$_2$, —COOH, —C(O)NMe$_2$, —C(O)NEt$_2$, phenyl, naphthyl, pyridinyl, pyrimidinyl, pyrazinyl, triazinyl, pyrrolidinyl, imidazolyl, $C_1$-$C_6$-alkyl, $C_2$-$C_6$alkenyl, $C_2$-$C_6$alkynyl, —C(O)O$C_1$-$C_6$alkyl, —C(O)O$C_2$-$C_6$alkenyl, —C(O)O$C_2$-$C_6$alkynyl, —C(O)O(CH$_2)_p$Ph, —(CH$_2)_p$SH, halogen, SO$_2$PhNHCO$C_1$-$C_6$alkyl, NH$_2$, SH, O$C_1$-$C_6$alkyl, and wherein p is a number between 0 and 2, In another embodiment, $R_2$ and $R_3$, together with the nitrogen to which they are attached, form a 5-, 6-, or 7-membered ring which may optionally contain 1, 2 or 3 additional nitrogen atoms and may be saturated, unsaturated or partially unsaturated, and wherein the 5-, 6-, or 7-membered ring may optionally be substituted by between one and four substituents selected from the group consisting of: SO$_2$NMe$_2$, SO$_2$NH$_2$, —COO(CH$_2)_p$Ph-C(O)Me, —C(O)pyridyl, —(CH$_2)_p$OH, —C(O)NH$_2$, —COOH, —C(O)NMe$_2$, —C(O)NEt$_2$, phenyl, pyridinyl, pyrimidinyl, pyrazinyl, triazinyl, pyrrolidinyl, imidazolyl, $C_1$-$C_6$-alkyl, $C_2$-$C_6$alkenyl, $C_2$-$C_6$alkynyl, —C(O)O$C_1$-$C_6$alkyl, —C(O)O$C_2$-$C_6$alkenyl, —C(O)O$C_2$-$C_6$alkynyl, —C(O)O(CH$_2)_p$Ph, —(CH$_2)_p$SH, halogen, NH$_2$, SH, O$C_1$-$C_6$alkyl, p is a number between 0 and 2, In a further embodiment, $R_2$ and $R_3$, together with the nitrogen to which they are attached, form a saturated 5-, 6-, or 7-membered ring which may optionally contain 1, 2 or 3 additional nitrogen atoms, and wherein the 5-, 6-, or 7-membered ring may optionally be substituted by between one and three substituents selected from the group consisting of: SO$_2$NMe$_2$, SO$_2$NH$_2$, —C(O)Me, —C(O)pyridyl, —(CH$_2)_p$OH, —C(O)NH$_2$, —COOH, —C(O)NMe$_2$, —C(O)NEt$_2$, phenyl, pyridinyl, pyrimidinyl, pyrazinyl, triazinyl, pyrrolidinyl, imidazolyl, $C_1$-$C_6$-alkyl, $C_2$-$C_6$alkenyl, —C(O)O$C_1$-$C_6$alkyl, —C(O)O$C_2$-$C_6$alkenyl, halogen, NH$_2$, SH, p is a number between 0 and 2.

In a further embodiment $R_2$ and $R_3$ are independently selected from $C_1$-$C_{10}$ alkyl, or alternatively $R_2$ and $R_3$, together with the nitrogen to which they are attached, form a 5- or 6-membered ring which may optionally contain between 1 and 3 additional nitrogen atoms, and which may optionally be substituted with an aryl or heteroaryl group.

In a further embodiment $R_2$ and $R_3$ are independently selected from the $C_1$-$C_{10}$ alkyl, or alternatively $R_2$ and $R_3$, together with the nitrogen to which they are attached, form a 5- or 6-membered saturated ring which may optionally contain between 1 and 3 additional nitrogen atoms, and which may optionally be substituted with an aryl or heteroaryl group.

In another embodiment $R_2$ and $R_3$ are independently selected from $C_1$-$C_6$ alkyl, or alternatively $R_2$ and $R_3$, together with the nitrogen to which they are attached, form a saturated 5- or 6-membered ring which may optionally contain 1 or 2 additional nitrogen atoms, and which may optionally be substituted with a substituent selected from the group consisting of: pyrimidinyl, naphthyl, phenyl, pyrazinyl, triazinyl, triazolyl, imidazolyl, tetrazolyl and pyrrolyl.

In another embodiment $R_2$ and $R_3$ are independently selected from $C_1$-$C_6$ alkyl, or alternatively $R_2$ and $R_3$, together with the nitrogen to which they are attached, form a saturated 5- or 6-membered ring which optionally contains 1 additional nitrogen atom, and which may optionally be substituted with a substituent selected from the group consisting of: pyrimidinyl, naphthyl, phenyl, pyrazinyl, triazinyl, triazolyl, imidazolyl, tetrazolyl and pyrrolyl.

In another embodiment $R_2$ and $R_3$ are independently selected from $C_1$-$C_6$ alkyl, or alternatively $R_2$ and $R_3$, together with the nitrogen to which they are attached, form a saturated 5- or 6-membered ring which optionally contains 1 additional nitrogen atom, and which may optionally be substituted with a substituent selected from the group consisting of: pyrimidinyl, phenyl, pyrazinyl and triazinyl.

In yet another embodiment $R_2$ and $R_3$ are independently selected from methyl, ethyl or propyl, or alternatively $R_2$ and $R_3$, together with the nitrogen to which they are attached, form a saturated 5- or 6-membered ring which optionally contains 1 additional nitrogen atom, and which may optionally be substituted on the additional nitrogen with a substituent selected from the group consisting of: pyrimidinyl, phenyl, pyrazinyl and triazinyl.

In still a further embodiment $R_2$ and $R_3$ are independently selected from $C_1$-$C_6$ alkyl, or alternatively $R_2$ and $R_3$, together with the nitrogen to which they are attached, form a structure selected from the group consisting of:

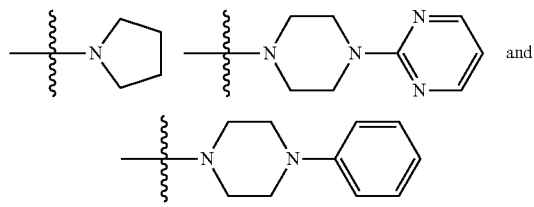

In a further embodiment $R_2$ and $R_3$ are independently selected from $C_1$-$C_6$ alkyl.

In yet another embodiment, $R_2$ and $R_3$ are independently selected from the group consisting of: methyl, ethyl, propyl and isopropyl.

In particular embodiments, $R_2$ and $R_3$, together with the nitrogen to which they are attached form the following structures:

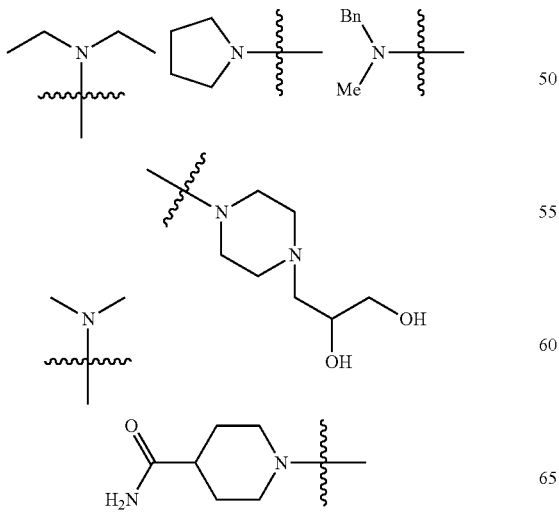

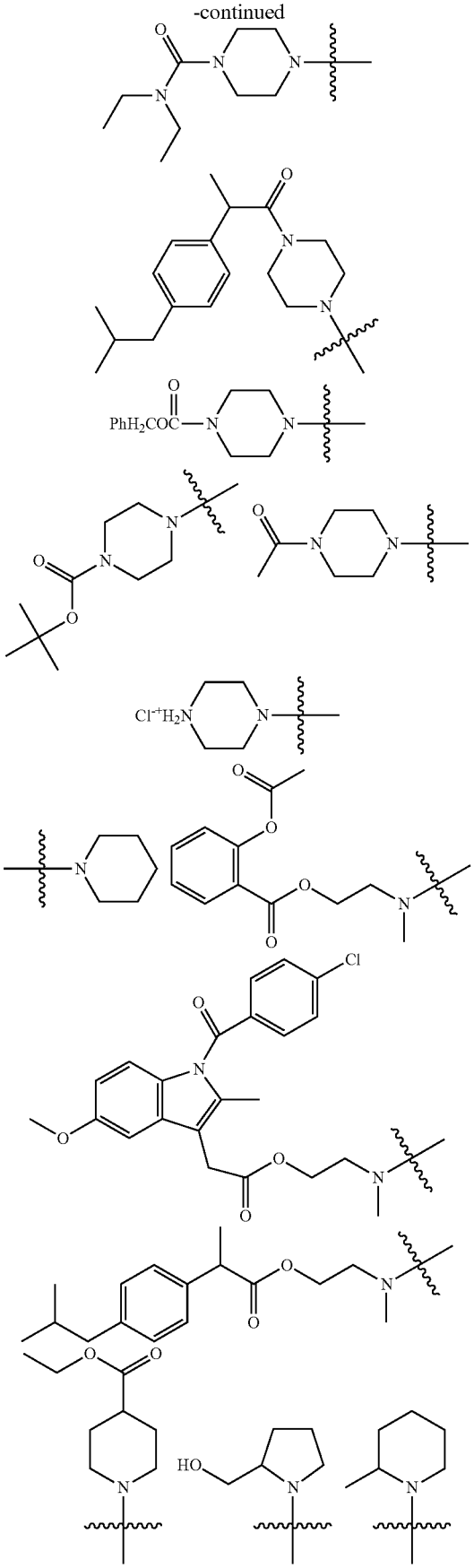

-continued
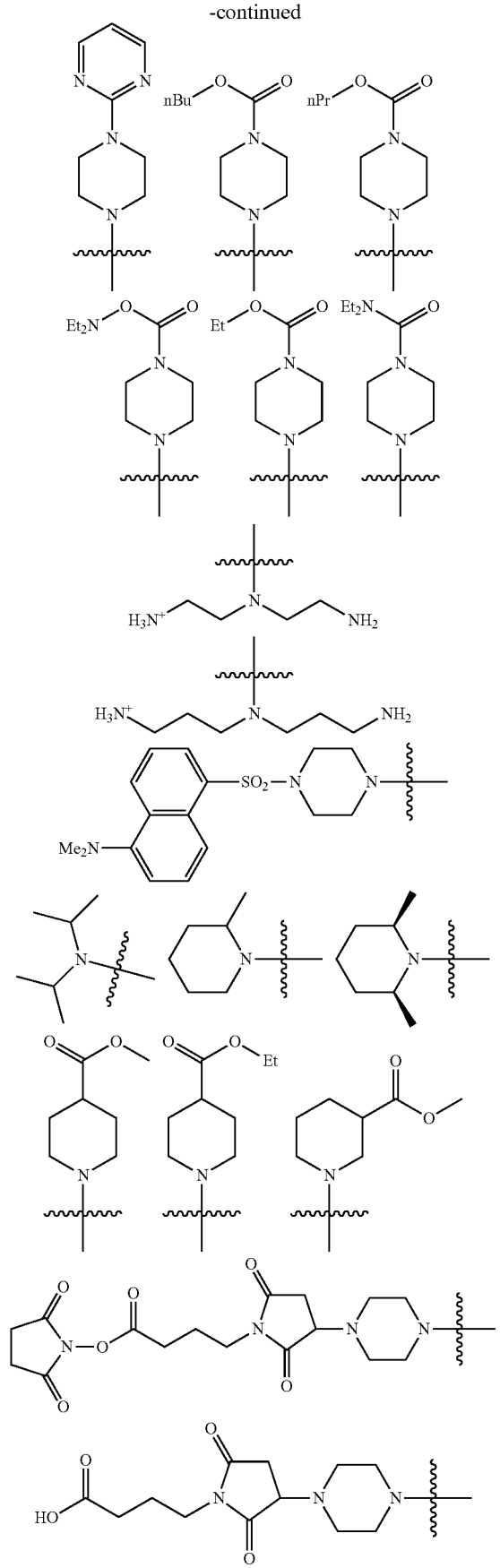
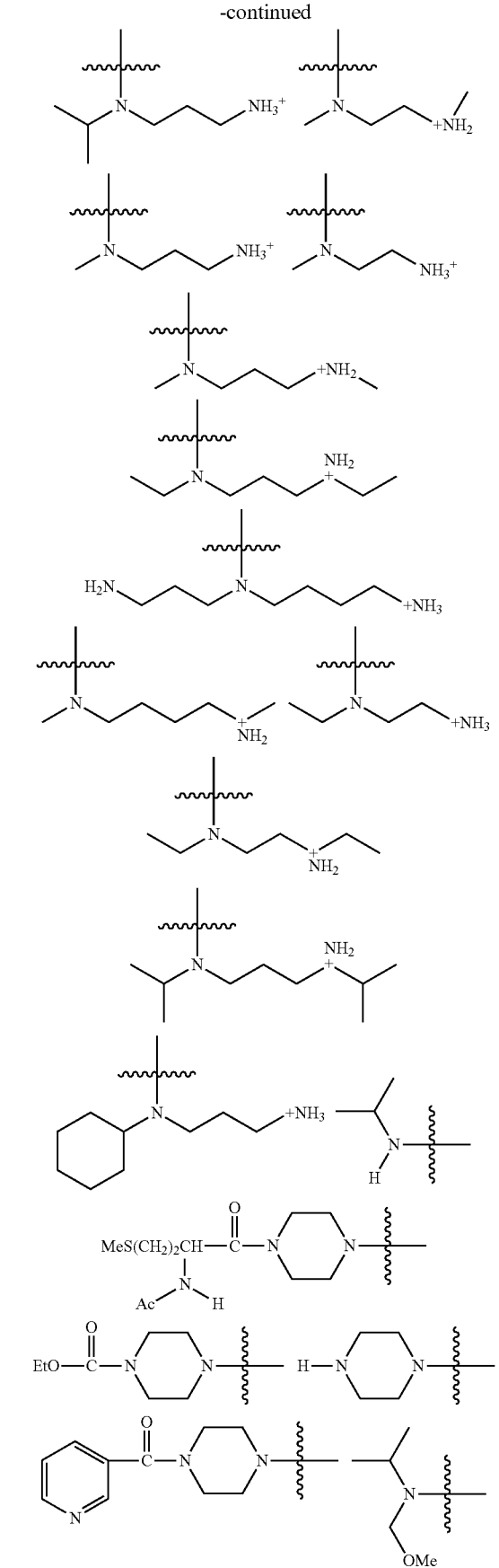

-continued
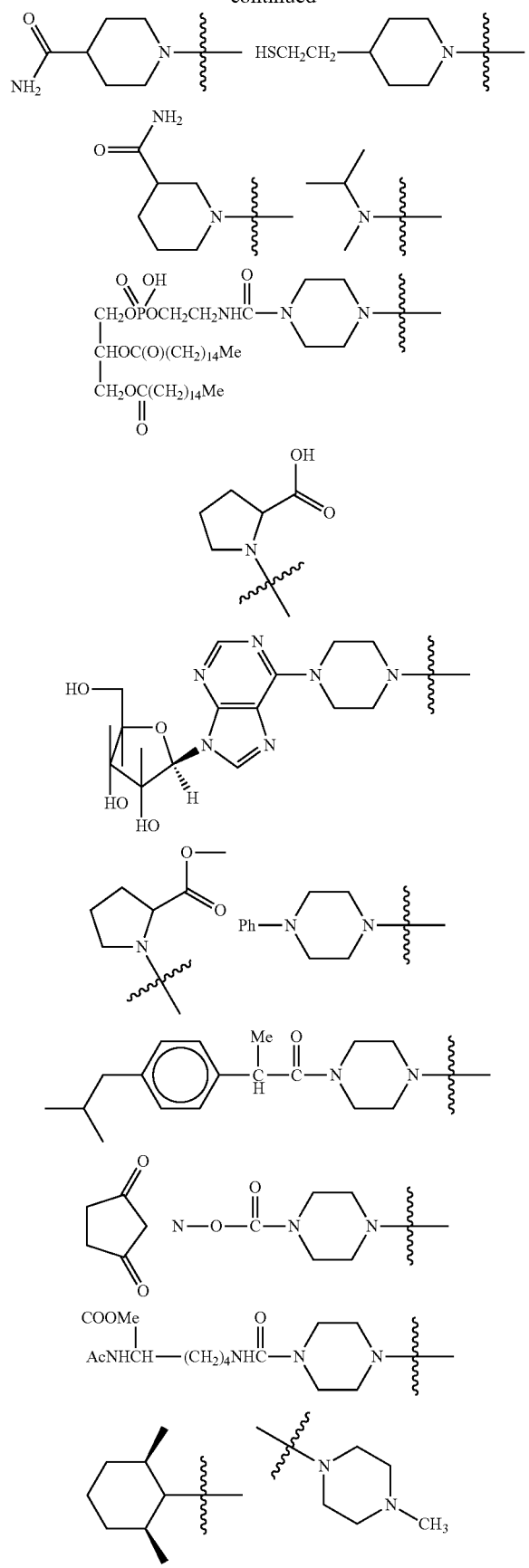
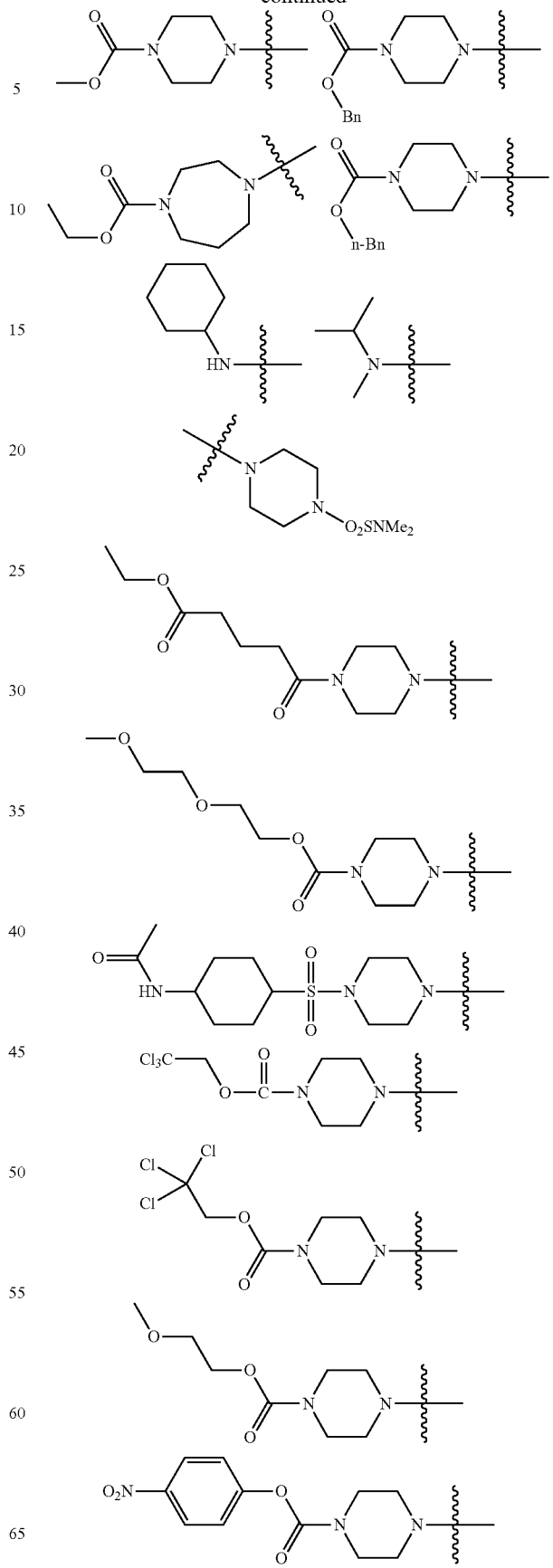

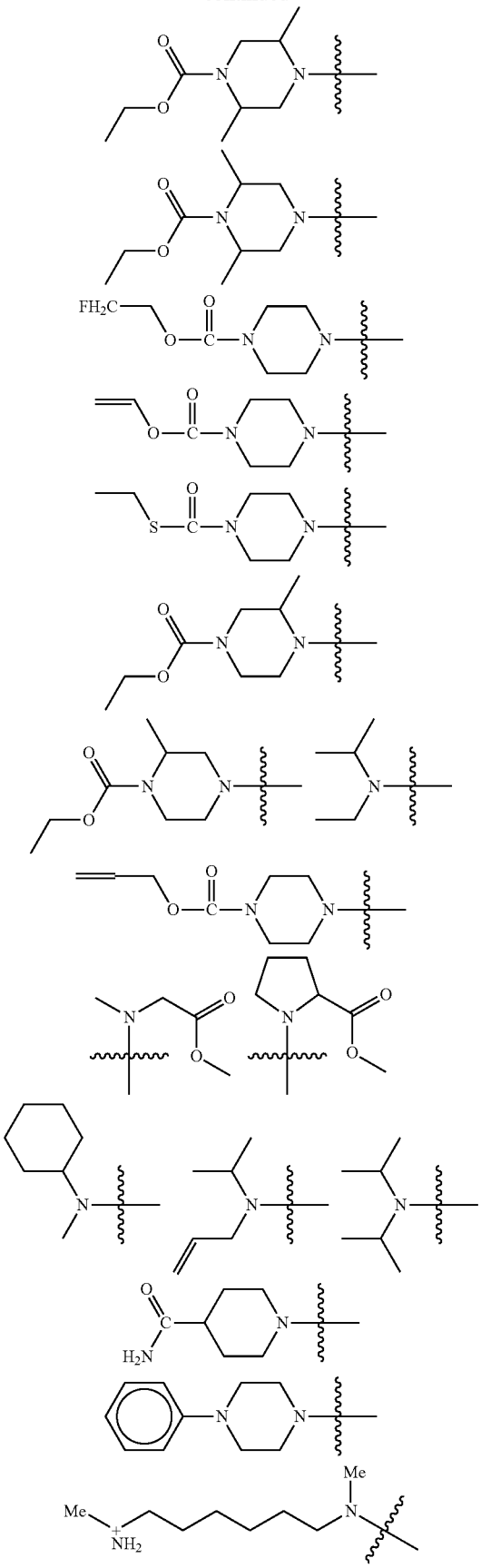
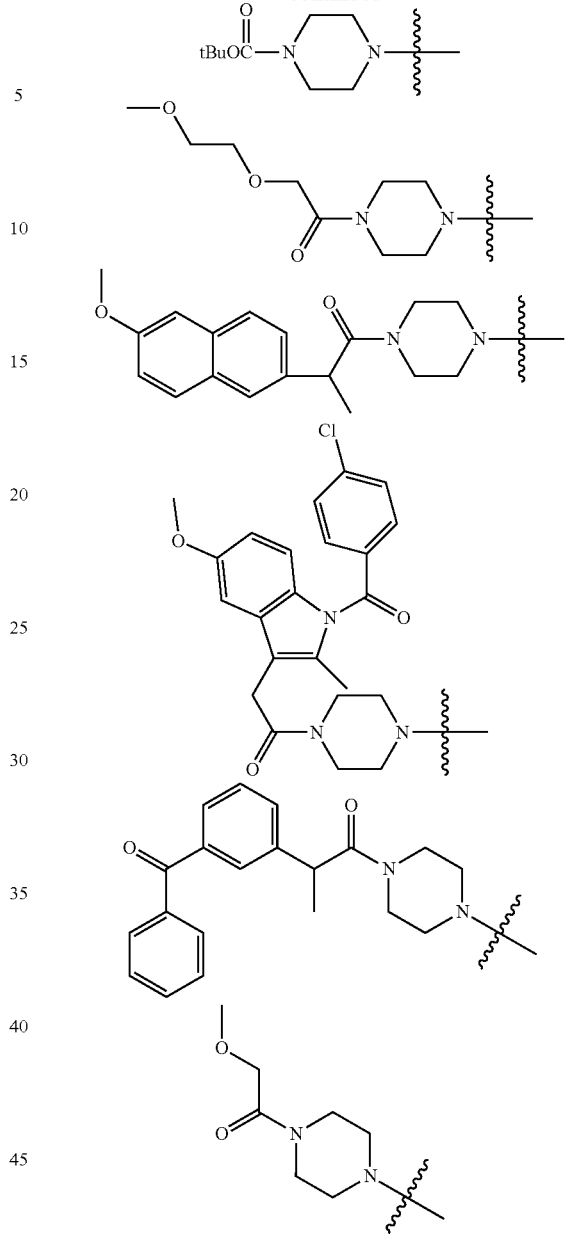

In an alternative embodiment T is $CH_2$, $R_1$ is Y-aryl or Y-heteroaryl where Y is a bivalent hydrocarbon having 1 to 4 carbon atoms and aryl and heteroaryl are optionally substituted with between 1 and 3 substituents selected from the group consisting of: $C_1$-$C_6$ alkyl, halo, amino and $OC_1$-$C_6$ alkyl, and $R_2$ and $R_3$ are independently selected from $C_1$-$C_{10}$ alkyl, or alternatively $R_2$ and $R_3$, together with the nitrogen to which they are attached, form a 5- or 6-membered ring which may optionally contain between 1 and 3 additional nitrogen atoms, and which may optionally be substituted with an aryl or heteroaryl group.

In an alternative embodiment T is $CH_2$, $R_1$ is Y-aryl or Y-heteroaryl where Y is a bivalent hydrocarbon having 1 to 4 carbon atoms and aryl and heteroaryl are optionally substituted, and $R_2$ and $R_3$ are independently selected from $C_1$-$C_{10}$ alkyl, or alternatively $R_2$ and $R_3$, together with the nitrogen to which they are attached, form a 5- or 6-membered ring which may optionally contain between 1 and 3 additional nitrogen atoms, and which may optionally be substituted with an aryl or heteroaryl group.

In a further embodiment T is $CH_2$, $R_1$ is Y-aryl or Y-heteroaryl where Y is a bivalent hydrocarbon having 1 to 4 carbon atoms, and the aryl group is selected from: phenyl, biphenyl, naphthyl, anthracenyl and phenanthrenyl, and the heteroaryl group is a 5- or 6-membered ring wherein between 1 and 4 carbon atoms are replaced with nitrogen and/or sulfur atoms, and wherein the aryl and heteroaryl groups may optionally be substituted with one or more substituents selected from: $C_{1-6}$ alkyl, halo, amino, hydroxyl, methoxy and ethoxy, and $R_2$ and $R_3$ are independently selected from $C_1$-$C_{10}$ alkyl, or alternatively $R_2$ and $R_3$, together with the nitrogen to which they are attached, form a 5- or 6-membered saturated ring which may optionally contain between 1 and 3 additional nitrogen atoms, and which may optionally be substituted with an aryl or heteroaryl group.

In a further embodiment T is $CH_2$, $R_1$ is Y-aryl or Y-heteroaryl where Y is a bivalent hydrocarbon having 1 to 4 carbon atoms, and the aryl group is selected from: phenyl, biphenyl, naphthyl, anthracenyl and phenanthrenyl, and the heteroaryl group is a 5- or 6-membered ring wherein between 1 and 4 carbon atoms are replaced with nitrogen and/or sulfur atoms, and $R_2$ and $R_3$ are independently selected from $C_1$-$C_6$ alkyl, or alternatively $R_2$ and $R_3$, together with the nitrogen to which they are attached, form a saturated 5- or 6-membered ring which may optionally contain 1 or 2 additional nitrogen atoms, and which may optionally be substituted with a substituent selected from the group consisting of pyrimidinyl, naphthyl, phenyl, pyrazinyl, triazinyl, triazolyl, imidazolyl, tetrazolyl and pyrrolyl.

In a further embodiment T is $CH_2$, $R_1$ is Y-aryl or Y-heteroaryl where Y is a bivalent hydrocarbon having 1 to 3 carbon atoms, and the aryl group is selected from: phenyl, biphenyl and naphthyl, and the heteroaryl group is selected from thienyl, tetrazolyl, imidazolyl, triazolyl, thiazolyl, isothiazolyl and pyrrolyl, and $R_2$ and $R_3$ are independently selected from $C_1$-$C_6$ alkyl, or alternatively $R_2$ and $R_3$, together with the nitrogen to which they are attached, form a saturated 5- or 6-membered ring which optionally contains 1 additional nitrogen atom, and which may optionally be substituted with a substituent selected from the group consisting of: pyrimidinyl, naphthyl, phenyl, pyrazinyl, triazinyl, triazolyl, imidazolyl, tetrazolyl and pyrrolyl.

In a further embodiment T is $CH_2$, $R_1$ is Y-aryl or Y-heteroaryl where Y is a bivalent hydrocarbon having 1 or 2 carbon atoms, and the aryl group is selected from: phenyl, biphenyl and naphthyl, and the heteroaryl group is selected from thienyl, tetrazolyl, imidazolyl, triazolyl, thiazolyl, isothiazolyl and pyrrolyl, and $R_2$ and $R_3$ are independently selected from $C_1$-$C_6$ alkyl, or alternatively $R_2$ and $R_3$, together with the nitrogen to which they are attached, form a saturated 5- or 6-membered ring which optionally contains 1 additional nitrogen atom, and which may optionally be substituted with a substituent selected from the group consisting of: pyrimidinyl, phenyl, pyrazinyl and triazinyl.

In a further embodiment T is $CH_2$, $R_1$ is Y-aryl or Y-heteroaryl where Y is —$CH_2$—, and the aryl group is selected from: phenyl, biphenyl and naphthyl, and the heteroaryl group is selected from thienyl, tetrazolyl, imidazolyl, triazolyl, thiazolyl, isothiazolyl and pyrrolyl and $R_2$ and $R_3$ are independently selected from $C_1$-$C_6$ alkyl, or alternatively $R_2$ and $R_3$, together with the nitrogen to which they are attached, form a saturated 5- or 6-membered ring which optionally contains 1 additional nitrogen atom, and which may optionally be substituted with a substituent selected from the group consisting of: pyrimidinyl, phenyl, pyrazinyl and triazinyl.

In a further embodiment T is $CH_2$, $R_1$ is Y-aryl or Y-heteroaryl where Y is —$CH_2$—, and the aryl group is selected from: phenyl, biphenyl and naphthyl, and the heteroaryl group is selected from thienyl, tetrazolyl, imidazolyl, triazolyl, thiazolyl, isothiazolyl and pyrrolyl, and $R_2$ and $R_3$ are independently selected from methyl, ethyl and propyl, or alternatively $R_2$ and $R_3$, together with the nitrogen to which they are attached, form a saturated 5- or 6-membered ring which optionally contains 1 additional nitrogen atom, and which may optionally be substituted on the additional nitrogen with a substituent selected from the group consisting of: pyrimidinyl, naphthyl, phenyl, pyrazinyl and triazinyl.

In a further embodiment T is $CH_2$, $R_1$ is Y-aryl or Y-heteroaryl where Y is —$CH_2$—, and the aryl group is selected from: phenyl, biphenyl and naphthyl, and the heteroaryl group is selected from thienyl, tetrazolyl, imidazolyl, triazolyl and pyrrolyl, and $R_2$ and $R_3$ are independently selected from $C_1$-$C_6$ alkyl, or alternatively $R_2$ and $R_3$, together with the nitrogen to which they are attached, form a saturated 5- or 6-membered ring which optionally contains 1 additional nitrogen atom, and which may optionally be substituted on the additional nitrogen with a substituent selected from the group consisting of pyrimidinyl, phenyl, pyrazinyl and triazinyl.

In a further embodiment T is $CH_2$, $R_1$ is Y-aryl or Y-heteroaryl where Y is —$CH_2$—, and the aryl group is selected from: phenyl and naphthyl, and the heteroaryl group is selected from thienyl, tetrazolyl, imidazolyl and triazolyl, and $R_2$ and $R_3$ are independently selected from $C_1$-$C_6$ alkyl, or alternatively $R_2$ and $R_3$, together with the nitrogen to which they are attached, form a saturated 5- or 6-membered ring which optionally contains 1 additional nitrogen atom, and which may optionally be substituted on the additional nitrogen with a substituent selected from the group consisting of: pyrimidinyl and phenyl.

In one embodiment T is $CH_2$, $R_1$ is selected from the group consisting of: —$CH_2$-phenyl, —$CH_2$-thienyl and —$CH_2$-tetrazolyl, and $R_2$ and $R_3$ are independently selected from $C_1$-$C_6$ alkyl, or alternatively $R_2$ and $R_3$, together with the nitrogen to which they are attached, form a structure selected from the group consisting of:

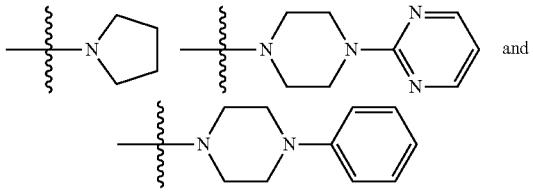

In still a further embodiment T is $CH_2$, $R_1$ is selected from the group consisting of: —$CH_2$-phenyl, —$CH_2$-thienyl and —$CH_2$-tetrazolyl, and $R_2$ and $R_3$ are independently selected from methyl, ethyl and propyl, or alternatively $R_2$ and $R_3$, together with the nitrogen to which they are attached, form a structure selected from the group consisting of:

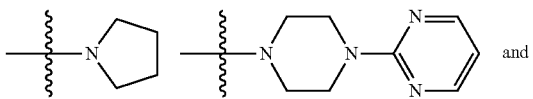

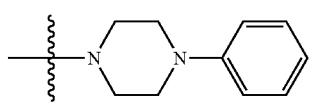

The compound of the formula (I) may have the following structure:

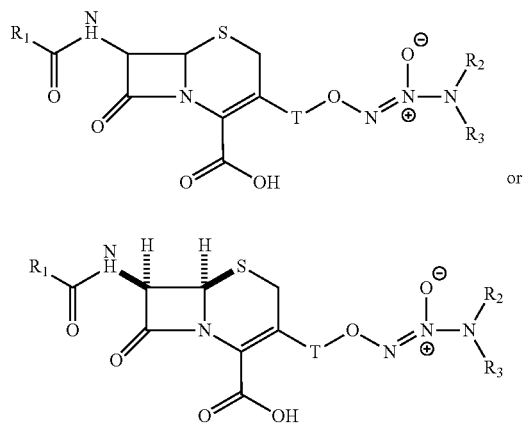

wherein $R_1$, $R_2$, $R_3$ and T are as defined above and herein.

When exposed to a β-lactamase or transpeptidase the compounds of the formula (I) ultimately undergo an elimination reaction which results in the liberation of nitric oxide. Accordingly, the compounds of formula (I) represent nitric oxide prodrugs. The mechanism by which nitric oxide is liberated from the compounds of the formula (I) is shown below in Scheme 1. Because the elimination reaction is instigated by exposure to a β-lactamase or transpeptidase, an enzyme specific to bacteria, the release of nitric oxide from the compounds of formula (I) can be localised in the vicinity of a biofilm thereby minimising side effects and toxicity at other locations that may be associated with the uncontrolled release of nitric oxide.

Scheme 1-Liberation of nitric oxide from compounds of the formula (I) following exposure to β-lactamase.

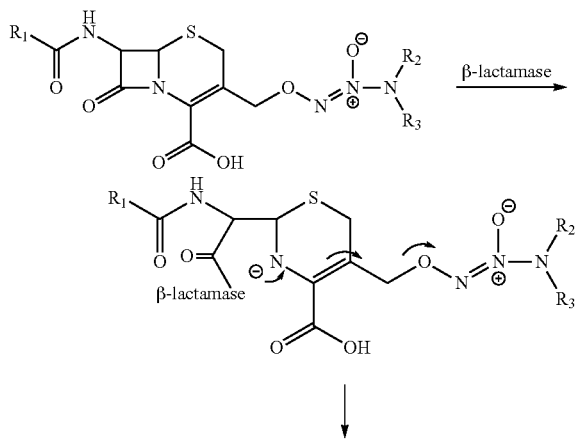

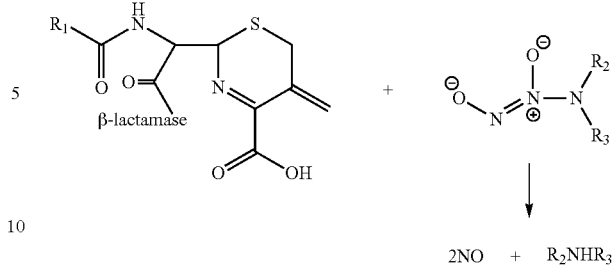

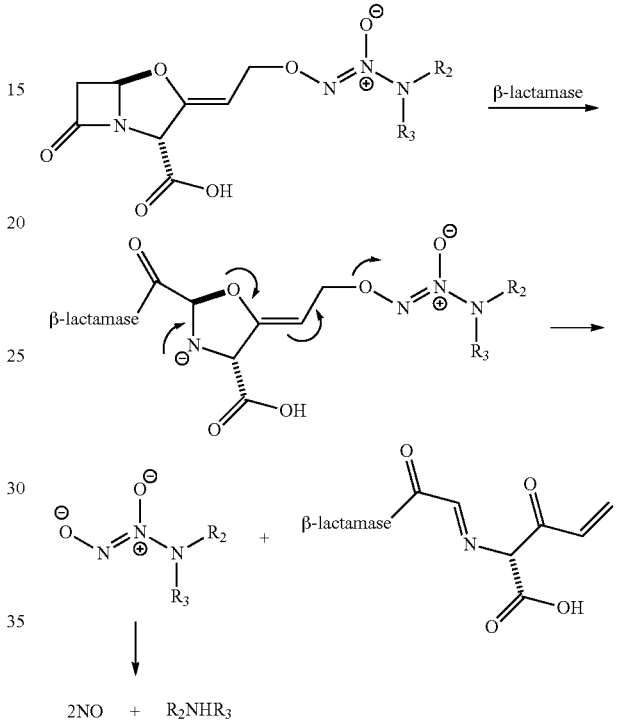

The rate of release of nitric oxide from the compounds of the formula (I) may be modulated by altering the $R_2$ and/or $R_3$ substituents. Release times in the order of a few seconds may be achieved when $R_2$ and $R_3$, together with the nitrogen to which they are attached, form a pyrrolidinyl ring, whereas release times in the order of a few minutes are possible when $R_2$ and $R_3$ are lower alkyl groups, such as ethyl for example. Release times in the order of about 3 to 20 hours may be achieved when $R_2$ and $R_3$ are lower alkyl groups having terminal amino substituents. Accordingly, an appropriate release rate of nitric oxide from the compounds of the formula (I) dependent on the intended application is achievable by selecting appropriate $R_2$ and $R_3$ substituents. Accordingly, those skilled in the art will recognise that $R_2$ and $R_3$ may be selected from amongst a broad range of organic residues depending on the desired release time.

Because of its remoteness from the β-lactam ring and diazeniumdiolate, the substituent $R_1$ exerts minimal effect on the reaction of a β-lactamase with the compounds of the formula (I) and the subsequent elimination of nitric oxide. Accordingly, those skilled in the art will recognise that $R_1$ is not limited to the specific substituents defined herein, but rather may represent any organic residue.

In particular embodiments, the compounds of the disclosure comprise a cephalosporin core or nucleus linked to a diazeniumdiolate. In further particular embodiments the cephalosporin is cephaloram. One exemplary compound of formula I provided by the present disclosure has the following structure. Both the free carboxylic acid and carboxylate salts (e.g. K⁺ salt) are contemplated

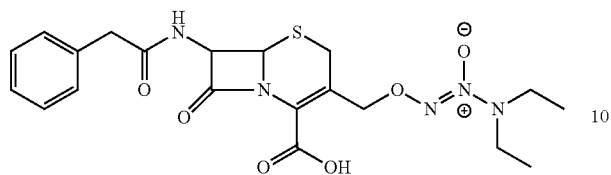

In additional embodiments the $R_2$ and/or $R_3$ substituents may further comprise an antibiotic which is liberated from the compounds of the formula (I) together with nitric oxide. The concomitant release of nitric oxide and the antibiotic may act in concert to more effectively kill biofilm microorganisms; the nitric oxide inducing and promoting the dispersal of microorganisms from a biofilm and the antibiotic acting on the dispersing cells. Those skilled in the art will appreciate that any suitable antibiotic may be linked to the $R_2$ and/or $R_3$ substituents of compounds defined herein, with the selection of the appropriate antibiotic depending on factors such as the identity of the biofilm-forming microorganisms, the extent of the biofilm and the environment in which the biofilm is located. The antibiotic may be an antibiotic comprising an NH group to facilitate formation of an antibiotic diazeniumdiolate conjugate. In one embodiment the antibiotic is ciprofloxacin or a related antibiotic such as N-desmethyl levofloxacin.

The compounds of the present disclosure may be prepared by coupling the —O—N═N⁺(O⁻)—N(R₂)(R₃) moiety to X, either via a linker or a direct bond. In one embodiment, exemplary compounds of the formula (I) may be prepared according to Scheme 2.

Scheme 2: Preparation of compounds of the formula (I).

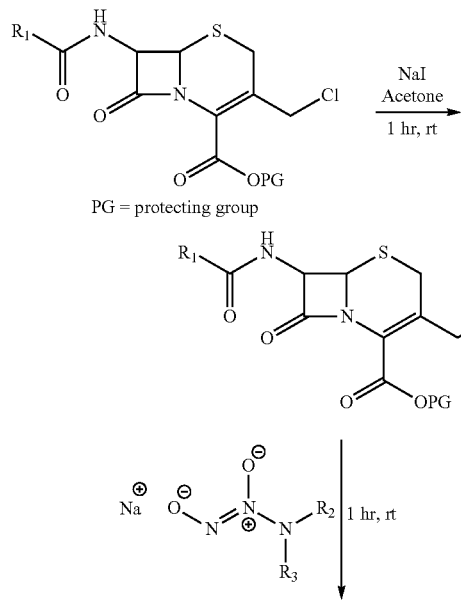

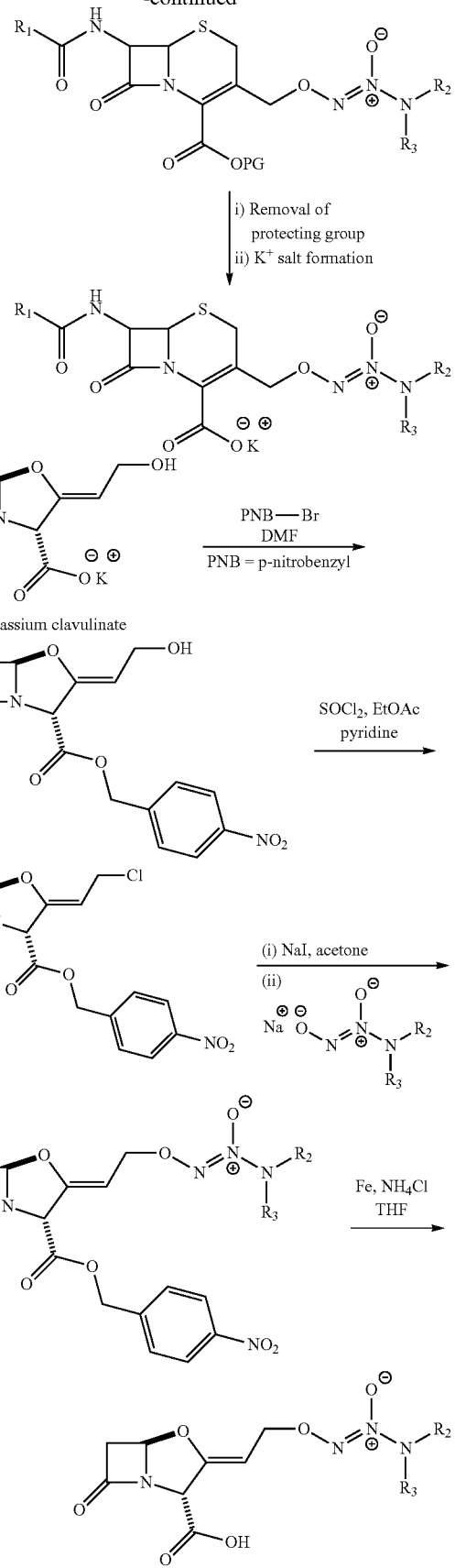

Compounds of the formula (I) wherein the $R_2$ and/or $R_3$ substituents further comprise an antibiotic may be prepared by the method depicted in Scheme 3.
Scheme 3: Preparation of a compound of formula (I) comprising an additional antibiotic (e.g. ciprofloxacin).
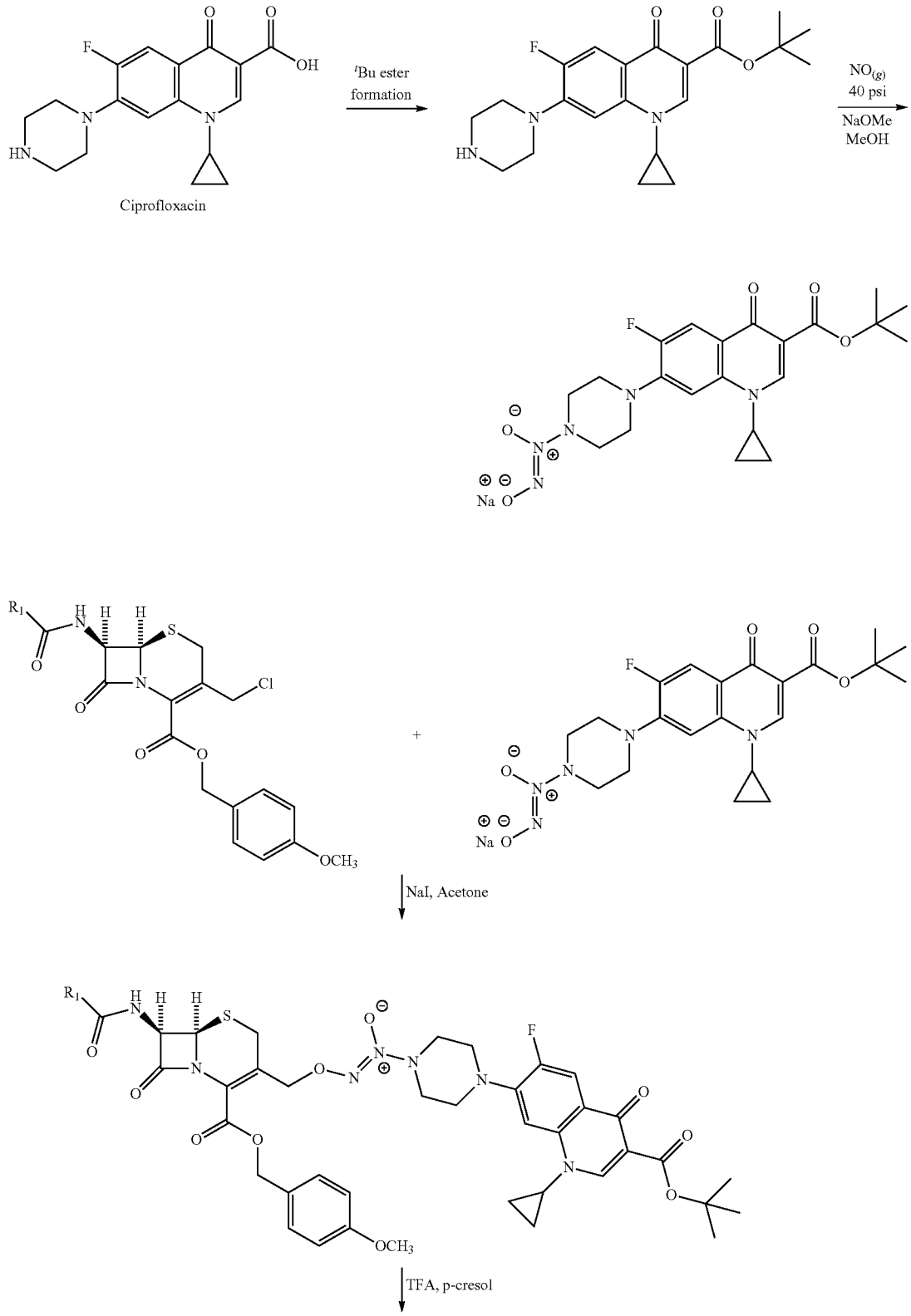

-continued

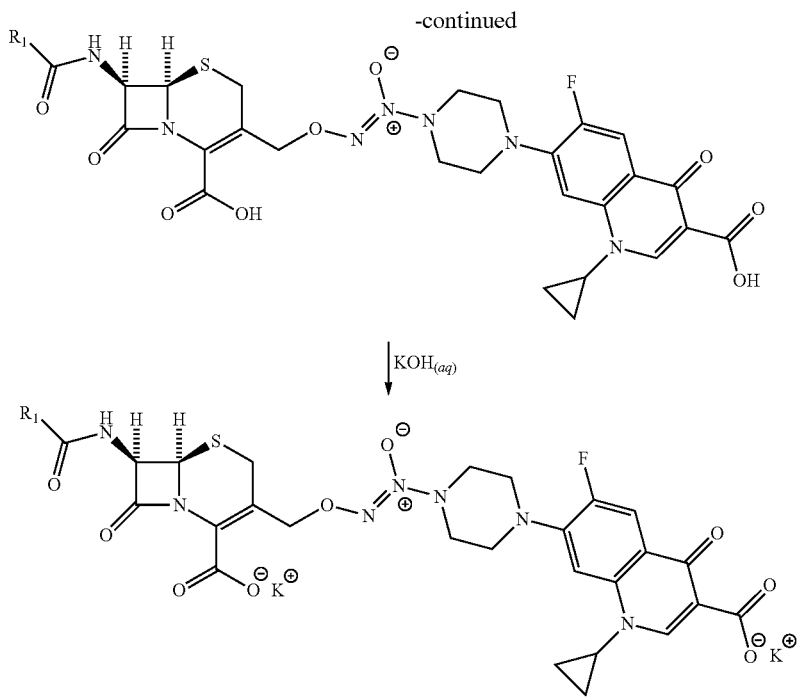

Whilst the antibiotic depicted in the method is ciprofloxacin those skilled in the art will appreciate that the method is applicable to other antibiotics that can be converted to diazeniumdiolate derivatives.

Typically, biofilms to be treated in accordance with embodiments described herein include microorganisms that express, or can be induced to express an enzyme such as a β-lactamase or a transpeptidase. Induction of expression of a β-lactamase may be achieved by pretreatment of microorganisms or biofilms with a suitable β-lactam antibiotic, or administration of a suitable β-lactam antibiotic together with administration of the compounds of formula (I). The β-lactam antibiotic may induce production of extracellular β-lactamase in said biofilm-forming microorganisms. The β-lactam antibiotic may be administered at any suitable concentration, which may be subinhibitory, bacteriostatic or bacteriocidal. The β-lactamase is one that is capable of recognising and cleaving a β-lactam ring. Suitable β-lactam antibiotics for use in inducing β-lactamase expression where necessary may therefore vary depending on the microorganisms to which the compounds of the formula (I) are to be delivered. Those of ordinary skill in the art would readily be able to determine the appropriate β-lactam antibiotic to be employed.

Accordingly, compounds, compositions and methods of the present disclosure enable the spatial and temporal control of nitric oxide release thereby facilitating the targeted delivery or administration of a nitric oxide generator or releasing agent to a desired site comprising a biofilm or at which a biofilm may form, and the release of nitric oxide with appropriate kinetics for the particular application.

Those skilled in the art will appreciate that embodiments of the present disclosure are applicable to single species or mixed species biofilms. Bacterial species to which the present invention relates may be any species capable of forming a biofilm or contributing to a biofilm and which produce or can be induced to produce a β-lactamase. Species may include, but are not limited to, *Pseudomonas* spp. such as *P. aeruginosa*, *Pseudoalteromonas* spp. such as *P. tunicata*, *Staphylococcus* spp. such as *S. aureus* and *S. epidermidis*, *Streptococcus* spp., *Escherichia* spp. such as *E. coli*, *Shigella* spp., *Mycobacterium* spp., *Enterococcus* spp., *Salmonella* spp., *Legionella* spp., *Haemophilus* spp., *Bacillus* spp., *Desulfovibrio* spp., *Shewanella* spp., *Geobacter* spp., *Klebsiella* spp. such as *K. pneumoniae*, *Proteus* spp. such as *P. mirabilis*, *Serratia* spp. such as *S. marcescens*, *Porhyromonas* spp., *Fusobacterium* spp., *Proteus* spp., *Aeromonas* spp., *Arthrobacter* spp., *Micrococcus* spp., and *Burkholderia* spp. Alternatively those skilled in the art will appreciate that in some applications of the present invention, the identities of the particular species in the mixed communities of the biofilm to be treated are undetermined and are not critical to the applicability of the invention.

In accordance with embodiments disclosed herein, compounds of the formula (I) are typically used in amounts such that a low, non-toxic concentration of nitric oxide is released in the vicinity of the biofilm or biofilm-forming microorganisms. The concentration may be in the nanomolar, micromolar, or millimolar range. In particular embodiments, the concentration may be between about 1 nM and about 100 mM, between about 10 nM and about 50 mM, between about 25 nM and about 50 mM, between about 50 nM and about 25 mM, between about 100 nM and about 10 mM, between about 200 nM and about 1 mM, between about 500 nM and 500 μM, between about 500 nM and 100 μM, or between about 1 μM and about 50 μM. The most suitable concentration to achieve the desired effect will depend on a number of factors and may be determined by those skilled in the art using routine experimentation. Such factors include, but are not limited to, the particular compound used for nitric oxide release, the means or route of administration of the compound, the nature, structure and age of the biofilm, the species of microorganism to be treated and so on.

Compounds, compositions and methods of the present disclosure may be employed in combination with at least one additional antibiotic or antimicrobial agent. As hereinbefore described the compounds of the present disclosure may incorporate an antibiotic linked to the $R_2$ and/or $R_3$ substituents. Alternatively, or in addition, compounds of the present disclosure may be administered or delivered in conjunction with one or more antibiotics or antimicrobial agents, either simultaneously or sequentially. For sequential application the antibiotics or antimicrobial agents may be formulated into the same composition as the compounds of the present disclosure. By way of example only, suitable antibiotics include but are not limited to β-lactams, monopenems, carboxypenems, aminoglycosides, quinolones, macrolides, lincozamides, tetracyclines, streptogramins, glycopeptides, rifamicins, sulphonamides chloramphenicol, nalidixic acid, azole-containing compounds and peptide antibiotics. Exemplary antibiotics include ceftazidime and tetracycline. Suitable antimicrobial agents include, but are not limited to, detergents, surfactants, agents that induce oxidative stress, bacteriocins and antimicrobial enzymes, peptides and phage. Antimicrobial enzymes include but are not limited to lipases, pronases, lyases (e.g. alginate lyases) and various other proteolytic enzymes and nucleases. The antibiotics and antimicrobial agents may be natural or synthetic. The antibiotic or antimicrobial agent employed may be selected for the particular application of the invention on a case-by-case basis, and those skilled in the art will appreciate that the scope of the present invention is not limited by the nature or identity of the particular antimicrobial agent.

The compounds, compositions and methods disclosed herein find application in a wide range of environments and circumstances. The following is a brief discussion of some general areas of application. However those skilled in the art will readily appreciate that any environment or situation in which biofilm development is a problem or in which it is desirable to inhibit microbial growth will be potentially suitable.

Compounds, compositions and methods of the present disclosure find particular application in the treatment, prevention and ongoing management of infectious diseases and of diseases and disorders associated with, characterised by, or caused by biofilms and biofilm-forming microorganisms. For example, a variety of bacterial infections associated with biofilm formation may be treated with methods and compositions of the invention, such as cystic fibrosis, otitis media, bacterial endocarditis, kidney stones, legionnaire's disease, urinary tract infections, pulmonary infections, dental plaque, dental caries and infections associated with surgical procedures or burns. Accordingly, compositions of the invention may be formulated as pharmaceutical compositions or form components of, for example, surgical dressings, mouthwash, toothpaste or saline solutions.

Compounds and compositions of the present disclosure may be included in pharmaceutical, cosmetic, dermatological or topical delivery compositions as preservatives to inhibit or prevent the growth and/or colonisation of unwanted microorganisms. The compositions of the invention are therefore useful for preventing spoilage and hence increasing the usable life of any type of pharmaceutical, cosmetic, dermatological or topical delivery compositions to which they are added. The compounds or compositions of the disclosure may be conveniently included in any solid or liquid pharmaceutical, cosmetic, dermatological or topical delivery composition during the manufacture thereof, or alternatively after manufacture. The term "cosmetic composition" is understood to mean a composition intended for placement in contact with any external part of an animal body, including the mucous membranes of the oral cavity, the teeth, the hair and the nails, for the purpose of, for example: protecting, perfuming, cleansing, maintaining (i.e. moisturising or exfoliating), beautifying, altering the appearance of, or altering the odour of, the body. Examples of cosmetic compositions include but are not limited to: nail care products, make up, products intended for application to the lips, face masks and scrubs, hair tints, dyes and bleaches, products for waving, straightening and fixing hair, cleansing products such as lotions, powders and shampoos, conditioning products such as. lotions, creams, oils, hairdressing products such as lotions and lacquers, products for care of the teeth and the mouth, including toothpastes, mouthwashes, tongue cleaners, dental bleaches/whiteners and denture cleansers, perfumes, toilet waters, Eau de colognes, feminine hygiene products, deodorants, antiperspirants, cleansers such as toilet soap, deodorant soap, astringent and skin washes, shaving products such as creams, foams and lotions, bath and shower preparations such as salts, foams, oils, gels, etc., depilatories, after-bath powders, hygienic powders, moisturising products such as creams, lotions, gels and foams, sunbathing products (without SPF or SPF<4), anti-wrinkle products (without SPF) and anti-ageing products (without SPF).

Compounds, compositions and methods of the present disclosure may also be used in coating medical devices, including medical and surgical equipment and implantable medical devices, including but not limited to venous catheters, drainage catheters (e.g. urinary catheters), stents, pacemakers, contact lenses, hearing-aids, percutaneous glucose sensors, dialysis equipment, drug-pump related delivery cannula, prostheses such as artificial joints, hearts, heart valves or other organs, medical fixation devices (e.g. rods, screws, pins, plates and the like). Further, embodiments of the present disclosure find application in wound repair, as for example, compounds and compositions comprising the same may be impregnated or coated onto sutures and wound dressings such as bandages.

Compounds, compositions and methods of the present disclosure also find application in a range of industrial and domestic applications, including bin not limited to water supply reservoirs and feed pipes, drain pipes (domestic or industrial scale), process equipment of, for example, cooling towers, water treatment plants, dairy processing plants, food processing plants, chemical manufacturing plants, pharmaceutical or biopharmaceutical manufacturing plants, oil pipelines and oil refinery equipment, and pulp and paper mills. Other amenable environments and settings include, for example, as marine anti-fouling paints or coatings, for example in treating ship hulls, aquaculture equipment, fishing nets or other in-water structures.

Compositions according to the present disclosure may be in any suitable form. Typically the form will depend on that which is most suitable for application or delivery to the required site and thus will vary with different medical, industrial and domestic applications. For example a composition may be formulated for in vivo administration, such as in the form of a liquid, suspension, nasal spray, eyedrops, powder, tablet, capsule, cream, paste, gel or lotion. For industrial and domestic applications the composition may be formulated as a paint, wax, other coating, emulsion, solution, gel, suspension, beads, powder, granules, pellets, flakes or spray. The skilled addressee will also recognise that the appropriate formulation will depend on the particular application and the proposed route of delivery. Suitable routes of administration for in vivo applications include, for example, oral, nasal, parenteral (e.g. intravenous, topical, intraarterial, intramuscular, intraocular), transdermal and subcutaneous administration.

Compositions of the invention typically also include carriers, diluents or excipients. Suitable carriers, diluents and excipients are known to those skilled in the art. The diluents, adjuvants and excipients must be "acceptable" in terms of being compatible with the other ingredients of the composition, and in the case of pharmaceutical compositions, not deleterious to the recipient thereof. Carriers may be liquid or solid. In the case of liquid carriers, the liquid may be an aqueous or non-aqueous solvent.

In addition to the controlled release of nitric oxide provided by the compounds of the present disclosure per se, a further level of controlled release may be desirable and may be imparted by the formulation of compounds into compositions. For pharmaceutical applications, a number of suitable controlled release systems are known in the art. For example, polymeric colloidal particles or microencapsulates (microparticles, microspheres or nanoparticles) in the form of reservoir and matrix devices may be employed, or the agent may be contained by a polymer containing a hydrophilic and/or leachable additive eg, a second polymer, surfactant or plasticiser, etc. to give a porous device, or a device in which the drug release may be osmotically 'controlled' (both reservoir and matrix devices). Large cage-like molecules such as the $C_{60}$ Buckminster-fullerenes ('Buckyballs') or hyperbranched (starburst) dendrimers may also be used.

Typically for anti-fouling and other industrial applications, the composition, for example in the form of a paint or other surface coating, employs a carrier enabling the controlled release of the active agent temporally and/or spatially. A variety of methods to achieve controlled release of bioactive agents are known to those skilled in the art and may include, for example, encapsulation of the active agent in a suitable polymer or polymer-based product. The polymer may be an organic or inorganic polymer, for example a polyolefin, polyether, polyester, polyamide, polyurethane or polypeptide. Suitable polymers for providing controlled release are known to those skilled in the art, for example as disclosed in U.S. Pat. No. 6,610,282, the disclosure of which is incorporated herein by reference.

Typically, the rate of release of the substance is determined by the properties of the polymer itself as well as environmental factors (such as pH, temperature etc). Controlled release systems are capable of delivering substances slowly and continuously for up to several years. Those skilled in art will appreciate that a number of controlled release systems are applicable to the delivery of agents according to the present invention. By way of example only, release may be diffusion controlled, chemically controlled or solvent activated.

In diffusion controlled systems, diffusion of the agent trapped within a polymer matrix is the rate-determining factor for the overall release rate. One type of diffusion controlled system employs a reservoir device in which the agent forms a core surrounded by an inert diffusion barrier. These systems include membranes, capsules, microcapsules, liposomes, and hollow fibers. Alternatively the device may be a monolithic device in which the active agent is dispersed or dissolved in an inert polymer. Diffusion through the polymer matrix is the rate-limiting step, and release rates are determined in part by the choice of polymer and its consequent effect on the diffusion and partition coefficient of the agent to be released.

In typical chemically controlled systems a polymer degrades over time and releases an agent in an amount proportional to the gradual erosion. Chemical control can be achieved using bioerodible or pendant chains. In a bioerodible system the agent is ideally distributed uniformly throughout a polymer in the same way as in monolithic diffusion systems. As the polymer surrounding the agent is eroded, the agent escapes. In a pendant chain system, the agent is covalently bound to the polymer and is released by bond scission owing to water or enzymes.

In typical solvent-activated controlled systems, the active agent is dissolved or dispersed within a polymeric matrix and is not able to diffuse through that matrix. Osmotic pressure is used as the driving force for release of the agent. In one type of solvent-controlled system, as the environmental fluid (e.g., water) penetrates the matrix, the polymer (e.g a hydrogel) swells and its glass transition temperature is lowered below the environmental (host) temperature. Thus, the swollen polymer is in a rubbery state and allows the drug contained within to diffuse through the encapsulant.

Chemical bonding of a bioactive agent to a polymer can be accomplished in several general ways based on different methods of synthesis well known to those skilled in the art including: reaction on preformed polymers; reactions on naturally-occurring polymers; polymerization of vinyl monomers containing the active ingredient; and step growth polymerizations. When the bioactive agent is chemically bonded to a polymer, the bond has to be cleaved by a chemical reaction—typically enzymatic, hydrolytic, thermal, or photochemical. A variety of chemical and physical variables can affect the rate of bond cleavage and subsequent release of chemically attached materials from polymers including the nature of the labile bone, length of the spacer group, molecular weight, hydrophilicity, neighbouring group effects, environmental factors and physical form and dimensions.

In anti-fouling applications, self-polishing antifouling coatings are known in the art. Such coatings are typically based on polymers of tributyltin methacrylate, methyl methacrylate, and film softening monomers such as 2-ethylhexyl acrylate. An organotin polymer typically acts as the paint binder. Such paints may also contain a toxicant additive such as cuprous oxide or a triorganotin compound. In addition, the usual paint additives such as pigments, thixotropic agents may also be present. In normally alkaline seawater, the polymeric organotin binder is gradually hydrolyzed, and the tributyltin is liberated in a form that is an active antifoulant. The hydrolyzed polymer formed is water-soluble or water-swellable and is easily eroded off the surface by moving seawater, exposing a fresh surface of paint.

Those skilled in the art will readily appreciate that the delivery systems and methods described above are merely examples of suitable methods and systems that may be employed in the present invention. Any other suitable carriers and delivery systems may be employed to achieve the desired means of application of agents according to embodiments of the present invention.

Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 1% to 99.9% by weight of the compositions.

For pharmaceutical applications, compositions may be formulated for delivery by any route, for example oral, topical, intracavitary, intravesical, intramuscular, intraarterial, intravenous or subcutaneous.

Those skilled in the art will appreciate that the aspects and embodiments described herein are susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations of any two or more of said steps or features.

The citation of any reference herein should not be construed as an admission that such reference is available as "Prior Art" to the present application. Further, the reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present disclosure is further described by reference to the following non-limiting examples.

EXAMPLES

Example 1

Synthesis of Compounds

The following representative compounds of the formula (I) were synthesised:

14

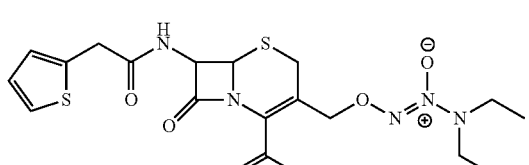

15

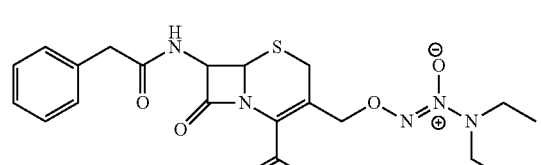

16

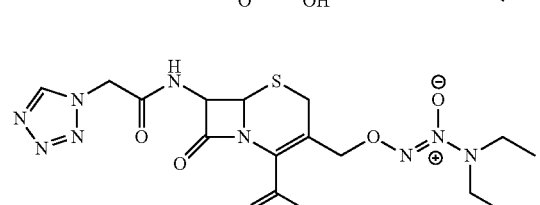

17

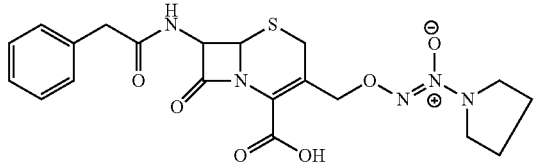

18

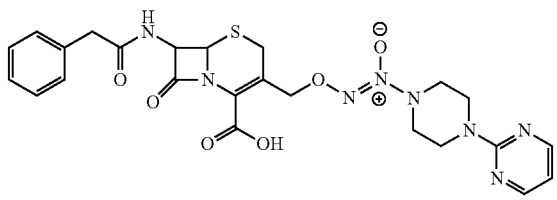

19

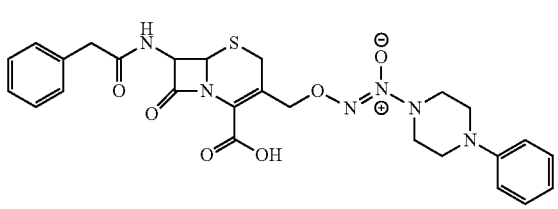

20

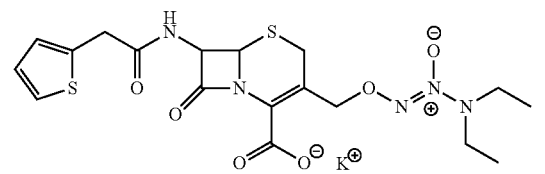

21

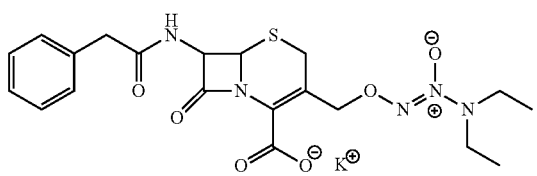

22

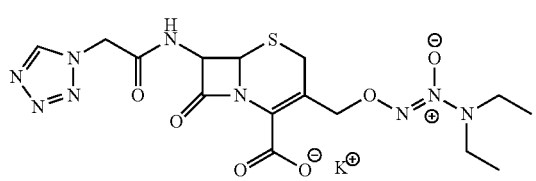

23

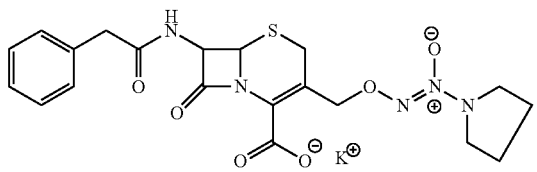

43
-continued
24
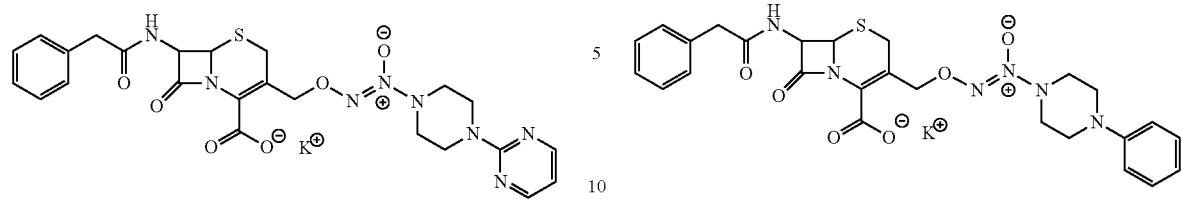
44
-continued
25
The compounds were synthesised according to Scheme 4:
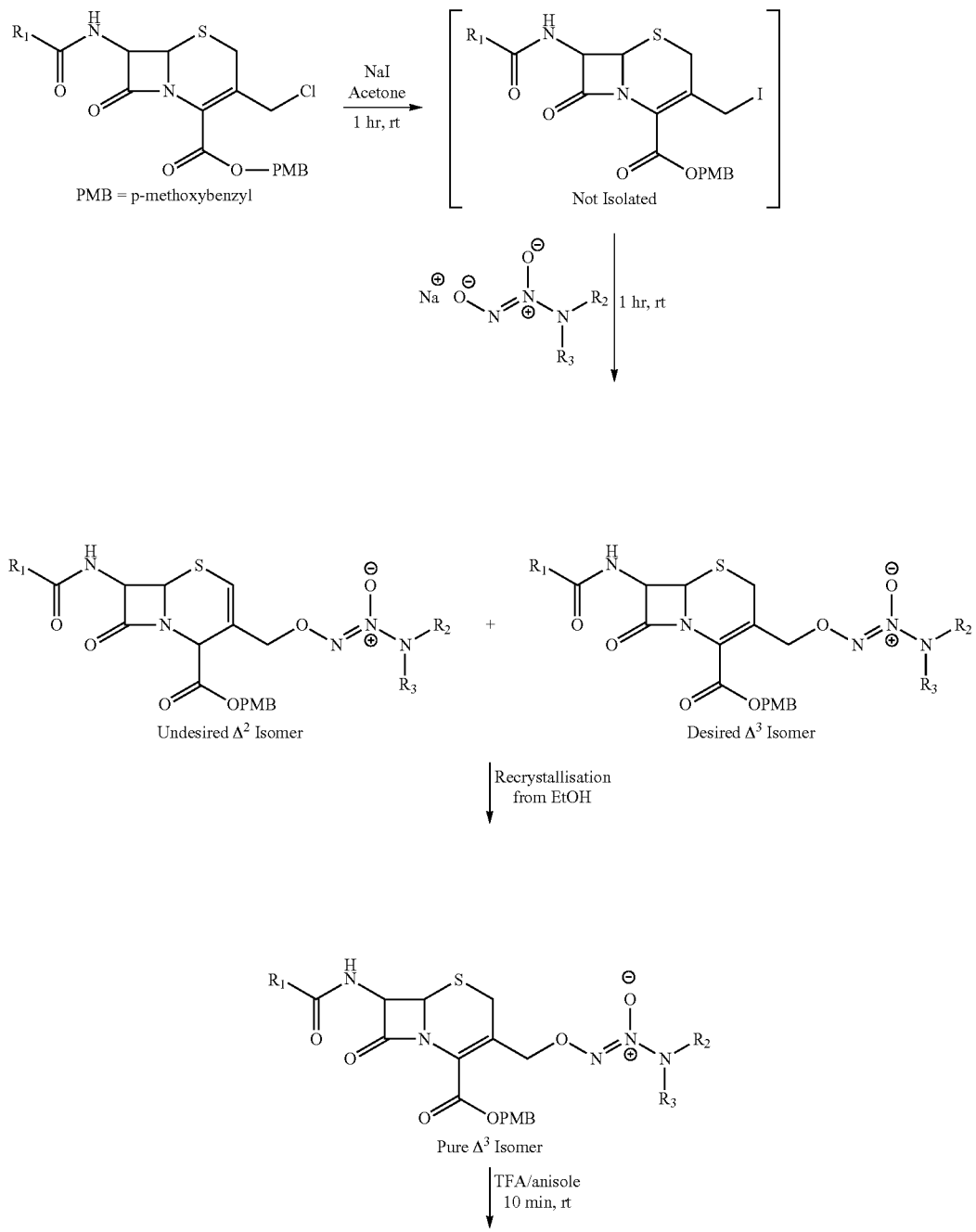

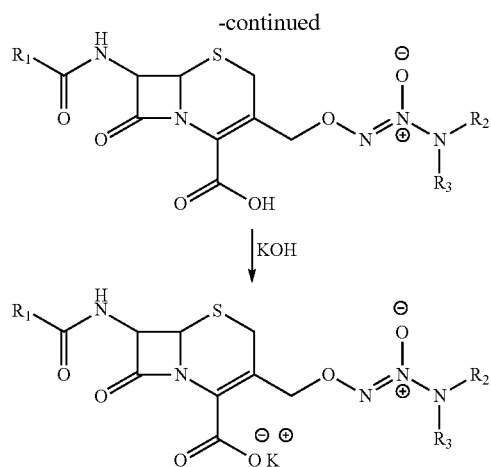

The first step in the synthesis of compounds 14 to 25 involved preparation of cephalosporin-3'-diazeniumdiolates 3 and 9-13 by reaction of appropriately functionalised PMB-protected cephalosporins 1, 4 and 5 with appropriately functionalised diazeniumdiolates 2 and 6 to 8, as shown below:

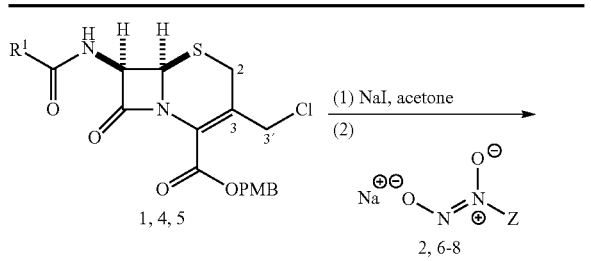

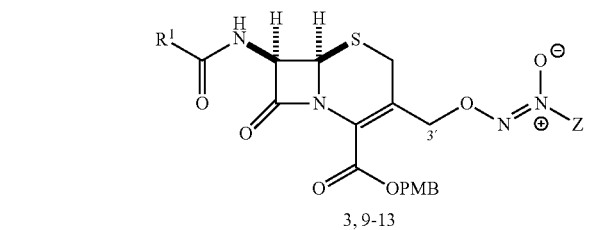

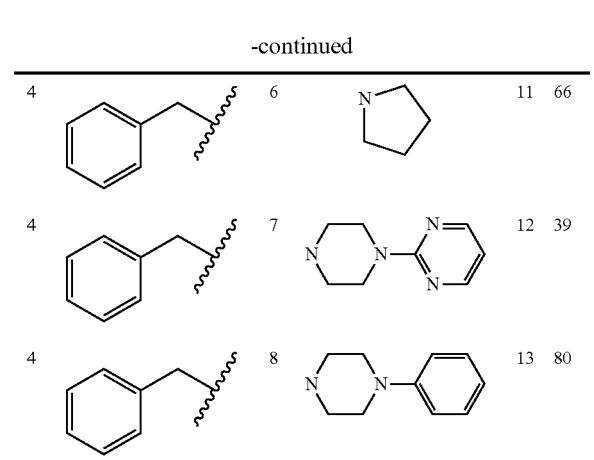

| Starting material, $R^1$ | | Sodium Diazeniumdiolate, Z | Product | Yield %[a] |
|---|---|---|---|---|
| 1 | (thiophene-CH2) | 2 | NEt$_2$ | 3 | 85 |
| 4 | (benzyl) | 2 | NEt$_2$ | 9 | 75[b] |
| 5 | (tetrazole-CH2) | 2 | NEt$_2$ | 10 | 14[c] |
| 4 | (benzyl) | 6 | N(pyrrolidine) | 11 | 66 |
| 4 | (benzyl) | 7 | N(piperazine-pyrimidine) | 12 | 39 |
| 4 | (benzyl) | 8 | N(piperazine-phenyl) | 13 | 80 |

[a] Isolated yield of pure Δ2-isomer,
[b] Δ3-isomer typically isolated in ~5% yield,
[c] 42% of pure Δ3-isomer isolated.

Compound 3 was prepared utilising the following method.

Sodium iodide (0.912 g, 6.08 mmol) was added to a suspension of the PMB-protected cephalosporin ester 1 (3.00 g, 6.08 mmol) in anhydrous acetone (25 mL) under $N_2$ and the mixture was stirred in the dark at room temperature for 1 h. Sodium (Z)-1-(N,N-diethylamino)diazen-1-ium-1,2-diolate 2 (0.944 g, 6.08 mmol) was then added in one shot and the mixture stirred at room temperature for a further 1.5 hrs (TLC analysis; Pet Spirit:EtOAc 7:3). The solvent was removed under reduced pressure and the residue diluted with $CH_2Cl_2$ (75 mL) and washed with 10% aq. sodium thiosulphate (2×40 mL) and water (1×40 mL). The organic fraction was dried over anhydrous $MgSO_4$ and concentrated in vacuo. The crude product was purified by silica gel column chromatography (Pet. Spirit:EtOAc, 7:3) and recrystallised from EtOH or MeOH to give 3 (3.04 g, 85%) as a pale yellow powder. $^1$H NMR (500 MHz, CDCl$_3$): δ 7.32 (d, 2H, J=8.5 Hz), 7.26 (d, 1H, J=5 Hz), 7.00-6.96 (m, 2H), 6.89 (d, 2H, J=8.5 Hz), 6.34 (d, 1H, J=9 Hz), 5.81 (dd, 1H, J=10, 4.5 Hz), 5.34 and 4.99 (ABq, 2H, J=14.5 Hz), 5.18 (s, 2H), 4.90 (d, 1H, J=5 Hz), 3.84 (s, 2H), 3.80 (s, 3H), 3.52 and 3.44 (ABq, 2H, J=18.5 Hz), 3.11 (q, 4H, J=7.5 Hz), 1.05 (t, 6H, J=7.5 Hz). $^{13}$C NMR (500 MHz, CDCl$_3$): δ 169.8, 164.4, 161.2, 159.9, 134.6, 130.6, 127.8, 127.5, 126.6, 126.4, 126.0, 125.4, 113.9, 71.9, 68.1, 59.2, 57.4, 55.2, 48.3, 37.1, 25.9 11.5. FTIR (cm$^{-1}$, Neat): 3275, 1754, 1706, 1648, 1517, 1362, 1248, 1177, 1096, 1027, 822. M.P 166° C. $[\alpha]_D$ (c=1.0, —CHCl$_3$)=+39.0. ESI-HRMS (m/z) Calcd. for 588.1592 [M-H]$^-$ $C_{26}H_{30}N_5O_7S_2^-$. Found 588.1550.

Compounds 9 to 13 were prepared using this same method by selecting appropriately functionalised PMB-protected cephalosporins and diazeniumdiolates. Spectroscopic data for compounds 9 to 13 is presented below.

Compound 9

$^1$H NMR (500 MHz, CDCl$_3$): δ 7.36-7.24 (m, 71-1), 6.88 (d, 2H, J=9 Hz), 6.08 (d, 1H, J=10 Hz), 5.81 (dd, 1H, J=10, 4.5 Hz), 5.33 and 4.98 (ABq, 2H, J=14 Hz), 5.17 (s, 2H), 4.88 (d, 1H, J=5 Hz), 3.79 (s, 31-1), 3.67 and 3.62 (ABq, 2H, J=9 Hz), 3.44 and 3.42 (ABq, 2H, J=18 Hz), 3.10 (q, 4H, J=7 Hz), 1.05 (m, 6H, J=7 Hz). $^{13}$C NMR (500 MHz, CDCl$_3$): 171.1, 164.6, 161.2, 159.9, 133.6, 130.7, 129.4, 129.2, 127.8, 126.7, 126.4, 125.5, 114.0, 72.0, 68.1, 59.2, 57.5, 55.2, 48.4, 43.3, 26.0, 11.5. FTIR (cm$^{-1}$, Neat): 3284, 1778, 1726, 1660, 1519, 1352, 1228, 1187, 1030, 982, 818, 716, 699, 679. M.P 126-128° C., [α]$_D$ (c=1.0, CH$_2$Cl$_2$)=+76.9, ESI-HRMS (m/z) Calcd. for 584.2179 [M+H]$^+$ C$_2$H$_{34}$N$_5$O$_7$S. Found 584.2205.

Compound 10

$^1$H NMR (500 MHz, CD$_3$OCD$_3$): δ 8.90 (s, 1H), 8.26 (d, 1H, J=6 Hz), 7.30 (d, 2H, J=8.5 Hz), 6.86 (d, 2H, J=8.5 Hz), 5.78 (q, 1H, J=5 Hz), 5.32 and 5.27 (ABq, 2H, J=16.5 Hz), 5.18 (s, 2H), 5.17 and 5.02 (ABq, 2H, J=13 Hz), 4.95 (d, 1H, J=5 Hz), 3.78 (s, 3H), 3.56 and 3.51 (ABq, 2H, J=19 Hz), 3.14 (q, 4H, J=7 Hz), 1.05 (t, 6H, J=7 Hz). $^{13}$C NMR (125 MHz, CD$_3$OD): δ 166.3, 164.4, 161.5, 160.2, 144.5, 130.0, 126.8, 126.6, 126.3, 114.2, 72.1, 68.5, 59.7, 57.5, 55.5, 50.1, 48.4, 26.5, 11.7. FTIR (cm$^{-1}$, Neat): 3290, 3137, 2973, 2902, 1771, 1702, 1662, 1556, 1378, 1233, 1170, 1094, 1049, 801. M.P 171° C., [α]$_D$ (c=1.0, acetone)=−51.9, ESI-HRMS (m/z) Calcd. for 574.1838 [M−H]$^-$ C$_{23}$H$_{28}$N$_9$O$_7$S$^-$. Found 574.1830.

Compound 11

$^1$H NMR (500 MHz, CDCl$_3$): δ 7.36 (m, 2H), 7.32 (d, 2H, J=8.5 Hz), 7.26 (m, 3H), 6.88 (d, 1H, J=8.5 Hz), 6.05 (d, 1H, J=9 Hz), 5.82 and 5.80 (dd, 1H, J=4.5, 5 Hz), 5.21-5.15 (m, 3H), 4.91 (d, 1H, J=4.4 Hz), 4.87 (d, 1H, J=13.5 Hz), 3.80 (s, 3H), 3.68 and 3.62 (ABq, 2H, J=16 Hz), 3.52 and 3.43 (ABq, 2H, J=18.5 Hz), 3.46 (t, 4H, J=7 Hz), 1.91 (t, 4H, J=7 Hz). $^{13}$C NMR (125 MHz, CDCl$_3$): 171.0, 164.7, 161.3, 159.9, 133.5, 130.6, 129.4, 129.2, 127.8, 126.8, 126.7, 125.3, 114.0, 71.4, 68.0, 59.1, 57.4, 55.2, 50.7, 43.3, 26.1, 22.8. FTIR (cm$^{-1}$, Neat): 3265, 2965, 2162, 2030, 1756, 1714, 1652, 1612, 1536, 1486, 1446, 1392, 1266, 1244, 1217, 1180, 1013, 986. M.P 157° C. [α]$_D$ (c=1.0, MeOH)=+20.6. ESI-HRMS (m/z) Calcd. for 580.1871 [M−H]$^-$ C$_{28}$H$_{30}$N$_5$O$_7$S$^-$. Found 580.1895.

Compound 12

$^1$H NMR (500 MHz, CDCl$_3$): δ 8.33 (d, 2H, J=4.5 Hz), 7.39-7.26 (m, 5H), 7.32 (d, 2H, J=7.5 Hz), 6.88 (d, 2H, J=7.5 Hz), 6.56 (t, 1H, J=2 Hz), 6.18 (d, 1H, J=9 Hz), 5.82 (q, 1H, J=5 Hz), 5.24 and 4.95 (ABq, 2H, J=13.5 Hz), 5.18 (d, 2H, J=2.5 Hz), 4.91 (d, 1H, =4.5 Hz), 3.98 (t, 4H, J=4.5 Hz), 3.78 (s, 3H), 3.66 and 3.61 (ABq, 2H, J=16 Hz), 3.53 and 3.40 (ABq, 2H, J=18.5 Hz), 3.41 (t, 4H, J=4.5 Hz). $^{13}$C NMR (500 MHz, CDCl$_3$): δ 171.0, 164.7, 161.3, 159.9, 157.8, 133.6, 130.7, 129.4, 129.2, 127.7, 126.6, 125.8, 125.7, 113.9, 110.7, 71.8, 68.1, 59.2, 57.4, 55.2, 50.9, 43.3, 42.3, 26.1. FTIR (cm$^{-1}$, Neat): 3286, 3137, 2976, 2908, 2904, 1772, 1702, 1662, 1557, 1411, 1377, 1232, 1049. [α]$_D$ (c=1.0, MeOH)=+ 39.5. ESI-HRMS (m/z) Calcd. for 675.2344 [M+H]$^+$ C$_{32}$H$_{35}$N$_8$O$_7$S$^+$. Found 675.2373. M.P 136° C.

Compound 13

$^1$H NMR (500 MHz, CDCl$_3$): δ 7.36-7.24 (m, 6H), 6.93-6.91 (m, 2H), 6.88 (d, 2H, J=9 Hz), 6.16 (m, 1H), 5.81 (q, 1H, J=5 Hz), 5.24 (d, 1H, J=2.5 Hz), 5.21 (s, 2H), 5.17 and 4.96 (ABq, 2H, J=12 Hz), 4.91 (d, 2H, J=2.5 Hz), 3.78 (s, 3H), 3.67 and 3.58 (ABq, 2H, J=16 Hz), 3.53 and 3.40 (ABq, 2H, J=18.5 Hz), 3.51 (m, 4H), 3.29 (m, 4H). $^{13}$C NMR (125 MHz, CDCl$_3$): δ 171.3, 164.9, 161.5, 160.2, 150.4, 133.8, 130.9, 129.6, 129.5, 129.4, 127.9, 126.9, 126.0, 121.0, 116.8, 114.2, 72.0, 68.4, 59.4, 57.7, 55.4, 51.1, 48.4, 43.5, 26.1. FTIR (cm$^{-1}$, Neat): 3389, 3286, 3197, 3030, 2897, 1756, 1647, 1607, 1546, 1492, 1448, 1384, 1351, 1224, 1004. [α]$_D$ (c=1.0, MeOH)=+54.3, ESI-HRMS (m/z) Calcd. for 673.2439 [M+H]$^+$ C$_{34}$H$_{37}$N$_6$O$_7$S$^+$. Found 673.2409. M.P 106° C.

The PMB-protected cephalosporin-3'-diazeniumdiolates (3 and 9 to 13) were then deprotected using neat trifluoroacetic acid to give the free carboxylic acids.

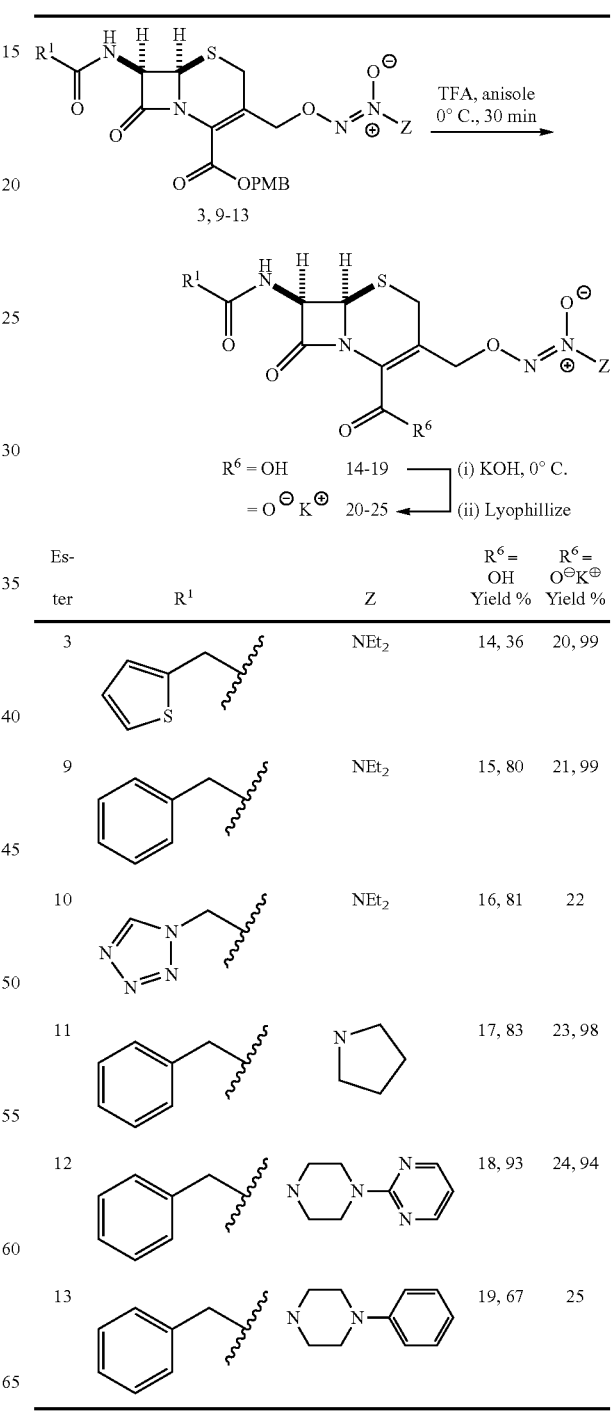

Compound 14 was prepared utilising the following method.

The PMB-protected cephalosporin-3'-diazeniumdiolate 3 (1.00 g, 1.69 mmol) and anhydrous anisole (0.55 g, 5.09 mmol) were stirred at 0° C. for 30 mins with trifluoroacetic acid (4.0 mL) after which the mixture was poured slowly onto crushed ice 100 g). Upon melting, the aqueous mixture was extracted with $CH_2Cl_2$ (3×70 mL) and the combined organic extracts were dried over anhydrous $MgSO_4$ and concentrated under reduced pressure. The residue was purified by silica gel column chromatography ($EtOAc:MeOH:H_2O$, 85:15:0.5) to provide the cephalosporin-3'-diazeniumdiolate free acid 14 (0.285 g, 36%) as a pale yellow powder. $^1H$ NMR (500 MHz, $CD_3OD$): δ 7.26 (s, 1H, J=1 Hz), 6.96-6.92 (m, 2H), 5.73 (d, 1H, J=5, Hz), 5.29 and 5.07 (ABq, 2H, J=12.9 Hz), 5.05 (d, 1H, 0.1=4.8 Hz), 3.83 and 3.79 (ABq, 2H, J=15 Hz), 3.62 and 3.53 (ABq, 2H, J=18 Hz), 3.16 (q, 4H, J=7.0 Hz), 1.04 (t, 6H, J=7.0 Hz). $^{13}C$ NMR (500 MHz, $CD_3OD$): δ 173.3, 166.1, 164.5, 137.4, 130.2, 128.4, 127.7, 126.9, 125.8, 73.0, 60.8, 59.0, 49.0, 37.1, 27.1, 11.7. FTIR ($cm^{-1}$, Neat): 3275, 2156, 1754, 1661, 1656, 1522, 1320, 1235, 1065, 995. M.P 87° C., $[α]_D$ (c=1.0, MeOH)=+84.4, ESI-HRMS (m/z) Calcd. for 468.1017 $[M-H]^- C_{18}H_{22}N_5O_6S_2^-$. Found 468.0996.

Compounds 15 to 19 were prepared using this same method. Spectroscopic data for compounds 15 to 19 is presented below.

Compound 15

$^1H$ NMR (500 MHz, $CD_3OD$): δ 7.35-7.26 (m, 5H), 5.75 (d, 1H, J=4.8, Hz), 5.36 and 5.07 (ABq, 2H, J=12.9 Hz), 5.05 (d, 1H, J=4.8 Hz), 5.03 (m, 1H), 3.68-3.45 (m, 4H), 3.19 (q, 4H, J=7.0 Hz), 1.07 (t, 6H, J=7.0 Hz). $^{13}C$ NMR (500 MHz, $CD_3OD$): δ 175.4, 167.3, 166.6, 137.2, 132.1, 131.0, 130.4, 128.8, 123.0, 74.6, 61.5, 59.8, 50.1, 44.0, 27.7, 12.6. FTIR ($cm^{-1}$, Neat): 3287, 1780, 1663, 1505, 1337, 1223, 998, 618. M.P 84-86° C., $[α]_D$ (c=1.0, $CH_2Cl_2$)=+19.4, ESI-HRMS (m/z) Calcd. for 462.1453 ($C_{20}H_{24}N_5O_6S$) $[M-H]^-$. Found 462.1465.

Compound 16

$^1H$ NMR (300 MHz, $CD_3OCD_3$): δ 9.40 (d, 1H, J=6 Hz), 9.11 (s, 1H), 5.72 (d, 2H, J=8 Hz), 5.29 (s, 2H), 5.22 and 4.99 (ABq, 2H, J=22 Hz), 5.01 (s, 1H), 3.52 and 3.49 (ABq, 2H, J=19 Hz), 3.10 (q, 4H, J=7 Hz), 0.95 (t, 6H, J=7 Hz). $^{13}C$ NMR (125 MHz, $CD_3OD$): δ 167.4, 165.8, 164.4, 146.0, 128.1, 127.5, 72.9, 60.6, 58.7, 50.3, 49.3, 27.1, 11.7. FTIR ($cm^{-1}$, Neat): 3282, 3136, 2975, 2875, 1773, 1703, 1662, 1559, 1414, 1227, 1170, 1026, 800. M.P 156° C. $[α]_D$ (c=1.0, MeOH)=+117.3, ESI-HRMS (m/z) Calcd. for 454.1263 $[M-H]^- C_{15}H_{20}N_9O_6S^-$. Found 454.1266.

Compound 17

$^1H$ NMR (500 MHz, $CD_3OD$): δ 7.30-7.22 (m, 5H), 5.72 (d, 1H, J=7.5 Hz), 5.23 and 4.97 (ABq, 2H, J=22.5 Hz), 5.07 (d, 1H, J=8 Hz), 3.64-3.50 (m, 4H), 3.50 (t, 4H, J=7 Hz), 1.93 (t, 4H, J=7 Hz). $^{13}C$ NMR (125 MHz, $CDCl_3$): 174.5, 166.2, 164.5, 136.4, 130.4, 129.5, 127.9, 127.6, 72.5, 60.7, 59.1, 51.5, 43.1, 27.2, 23.7. FTIR ($cm^{-1}$, Neat): 3296, 1756, 1729, 1642, 1530, 1469, 1429, 1388, 1318, 1141, 1028, 944. $[c]_p$ (c=1.0, MeOH)=122.8, ESI-HRMS (m/z) Calcd. for 484.1261 $[M+Na]^+ C_{20}H_{23}N_5NaO_6S^+$. Found 484.1281. M.P 146° C.

Compound 18

$^1H$ NMR (300 MHz, $CD_3OCD_3$): δ 8.37 (s, 2H), 7.34-7.23 (m, 5H), 6.65 (s, 1H), 5.84 (s, 1H), 5.24 and 4.97 (ABq, 2H, J=7.8 Hz), 5.14 (s, 1H), 3.97 (s, 4H), 3.69-3.41 (m, 4H), 3.46 (s, 4H). $^{13}C$ NMR (75 MHz, $CDCl_3$): 172.1, 166.4, 164.0, 163.0, 159.5, 137.5, 130.9, 129.9, 128.0, 126.7, 111.9, 72.8, 61.5, 58.2, 52.0, 43.3, 42.3, 26.1. FTIR ($cm^{-1}$, Neat): 3286, 3137, 2976, 2908, 2904, 1772, 1702, 1662, 1557, 1411, 1232, 1049. $[α]_D$ (c=1.0, MeOH)=+36.6, ESI-HRMS (m/z) Calcd. for 555.1769 $[M+H]^+ C_{24}H_{27}N_8O_6S^+$. Found 555.1799. M.P 116° C.

Compound 19

$^1H$ NMR (500 MHz, $CD_3COCD_3$): δ 8.05 (d, 1H, J=8.5 Hz), 7.36-7.23 (m, 8H), 7.02 (d, 2H, J=7.5 Hz), 6.84 (t, 1H, J=7.5), 5.85 (q, 1H, J=5 Hz), 5.25 and 5.01 (ABq, 2H, J=13.5 Hz), 5.14 (d, 1H, J=4.5 Hz), 3.70 and 3.58 (m, 4H), 3.55 (m, 4H), 3.35 (m, 4H). $^{13}C$ NMR (500 MHz, $CD_3COCD_3$): 171.6, 165.8, 163.1, 151.5, 136.5, 130.0, 129.8, 129.1, 127.4, 125.9, 120.7, 117.2, 72.2, 60.3, 58.5, 51.6, 48.7, 42.9, 26.7. FTIR ($cm^{-1}$, Neat): 3397, 3286, 3197, 3028, 2897, 1755, 1647, 1607, 1548, 1492, 1448, 1383, 1351, 1225, 1004, 985. $[α]_D$ (c=1.0, MeOH)=+57.7 ESI-HRMS (m/z) Calcd. for 553.1864 $[M+H]^+ C_{26}H_{29}N_6O_6S^+$. Found 553.1847. M.P 96° C.

Compounds 14, 15 17 and 18 were then converted to their potassium salts. Compound 20 was prepared utilising the following method.

Cephalosporin-3'-diazeniumdiolate free acid 14 (0.20 g, 0.42 mmol) was suspended in $H_2O$ (1.0 ml) at 0° C. to which was then added an ice-cold aqueous solution of KOH (0.023 g in 100 µL $H_2O$, 0.42 mmol). A pale yellow solution was rapidly formed and stirring was continued for a further 20 minutes at 0° C. The aqueous solution was washed with $CH_2Cl_2$ (2×2 mL) and then frozen and lyophilized to provide the potassium cephalosporin-3'-diazeniumdiolate carboxylate salt 20 (0.21 g, 99%) as a pale yellow powder. $^1H$ NMR (300 MHz, $D_2O$): δ 7.21 (d, 1H, J=10 Hz), 6.89-6.88 (s, 2H), 5.49 (d, 1H, J=4.5, Hz), 5.08 and 4.85 (ABq, 2H, J=12.6 Hz), 4.96 (d, 1H, J=4.8 Hz), 3.81 and 3.74 (ABq, 2H, J=15 Hz), 3.46 and 3.25 (ABq, 2H, J=18 Hz), 2.96 (q, 4H, J=7.0 Hz), 0.85 (t, 6H, J=7.0 Hz). $^{13}C$ NMR (125 MHz, $D_2O$): δ 174.4, 168.3, 164.7, 135.8, 132.9, 127.6, 127.5, 125.9, 115.4, 73.9, 59.4, 57.7, 49.0, 36.2, 25.5, 10.7. FTIR ($cm^{-1}$, Neat): 3395, 3326, 3210, 2883, 2816, 1600, 1369, 1233, 1034. $[α]_D$ (c=1.0, MeOH)=+90.9, ESI-HRMS (m/z) Calcd. for 508.0721 $[M+H]^+ C_{18}H_{23}N_5O_6S_2K^+$. Found 508.0742.

Compounds 21, 23 and 24 were prepared using this same method. Spectroscopic data for compounds 21, 23 and 24 is presented below.

Compound 21

$^1H$ NMR (500 MHz, $CD_3OD$): δ 7.30-7.20 (m, 5H), 5.65 (d, 1H, J=4.8, Hz), 5.35 and 4.85 (ABq, 2H, J=12.0 Hz), 4.98 (d, 1H, J=4.8 Hz), 3.60 and 3.55 (ABq, 2H, J=14 Hz), 3.57 and 3.37 (ABq, 2H, J=18 Hz), 3.15 (q, 4H, J=7.0 Hz), 1.04 (t, 6H, J=7.0 Hz). $^{13}C$ NMR (500 MHz, $CD_3OD$): δ 174.6, 168.7, 165.3, 136.5, 134.5, 130.2, 129.6, 128.0, 116.9, 74.7, 60.4, 58.9, 49.4, 43.1, 26.8, 11.8. IR ($cm^{-1}$, Neat): 3395, 1765, 1609, 1495, 1345, 1248, 997, 679. M.P 35-37° C. $[α]_D$ (c=1.0, $CH_2Cl_2$)=+19.0, ESI-HRMS (m/z) Calcd. for 502.1157 $C_{20}H_{25}KN_5O_6S$ $[M+H]^+$. Found 502.1163.

Compound 23

$^1H$ NMR (500 MHz, $D_2O$): δ 7.35-7.2 (m, 5H), 5.53 (d, 1H, J=4 Hz), 5.05 and 4.72 (ABq, 2H, J=12 Hz), 4.99 (d, 1H, J=4 Hz), 3.62-3.58 (m, 2H), 3.50 and 3.30 (ABq, 2H, J=13 Hz), 3.4 (m, 4H), 1.82 (m, 41-1). $^{13}C$ NMR (125 MHz, $D_2O$): δ 175.5, 168.4, 164.9, 135.0, 132.3, 129.3, 129.1, 127.9, 116.5, 72.9, 59.2, 58.0, 51.6, 42.3, 25.8, 22.5. FTIR ($cm^{-1}$, Neat): 3399, 3283, 3194, 2976, 2980, 2897, 1758, 1648, 1609, 1542, 1492, 1451, 1386, 1351, 1224, 1001. $[α]_D$ (c=1.0, MeOH)=−390.3. ESI-HRMS (m/z) Calcd. for 500.1001 $[M+H]^+ C_{20}H_{23}KN_5O_6S^+$. Found 500.1015.

Compound 24

$^1H$ NMR (300 MHz, $CD_3OD$): δ 8.33 (s, 2H), 7.39-7.26 (m, 5H), 7.32 (d, 1H, J=7.5 Hz), 6.56 (t, 1H, J=2 Hz), 5.63 (d, 1H, J=5 Hz), 5.24 and 4.95 (ABq, 2H, J=13.5 Hz), 5.18 (d, 2H, J=2.5 Hz), 4.91 (d, 1H, J=4.5 Hz), 3.98 (m, 4H, J=4.5 Hz), 3.66 and 3.61 (ABq, 2H, J=16 Hz), 3.53 and 3.40 (ABq, 2H, J=18.5 Hz), 3.41 (t, 4H, 0.1=4.5 Hz). $^{13}$C NMR (125 MHz, CD$_3$OD): 171.0, 164.7, 161.3, 159.9, 157.8, 133.6, 130.7, 129.4, 129.2, 127.7, 126.6, 125.8, 125.7, 113.9, 110.7, 71.8, 68.1, 59.2, 57.4, 55.2, 50.9, 43.3, 42.3, 26.1. FTIR (cm$^{-1}$, Neat): 3394, 3282, 3190, 3034, 2980, 2894, 1756, 1645, 1609, 1543, 1492, 1448, 1352, 1224, 994. $[\alpha]_D$ (c=1.0, MeOH)=−190.6, ESI-HRMS (m/z) Calcd. for 593.1328 $[M+H]^+$ C$_{24}$H$_{26}$KN$_8$O$_6$S$^+$. Found 593.1366.

Diazeniumdiolates 2 and 6 to 8 may be prepared according to literature procedures. By way of example, compound 2 was prepared as follows.

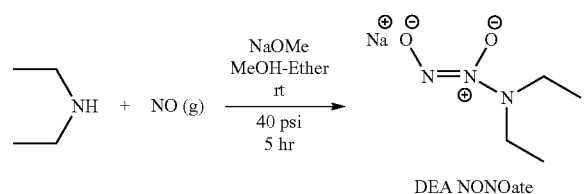

DEA NONOate (Reference: K. R. A. Abdellatif et al./*Bioorg. Med. Chem.* 15 (2007) 6796-6801).

Diethylamine (7.3 g, 0.1 mol) was added to a solution of NaOMe (0.1 mol, 24 mL of a 25% w/v solution in MeOH) and diethyl ether (300 mL) with stirring at 25° C. This mixture was purged with dry argon for 5 min, and then the reaction was pressurised under an atmosphere of nitric oxide (40 psi internal pressure) with stirring at 25° C. for 5 h. The product, which precipitated as a fine white powder, was isolated by filtration, suspended in diethyl ether (100 mL) and stirred for 15 min. The suspension was filtered and the solid collected was dried at 25° C. under reduced pressure until a constant weight was obtained. O$^2$-sodium 1-(N,N-diethylamino)diazen-1-ium-1,2-diolate (DEA NONOate) was afforded as a fine white powder (4.0 g, 26%). The product was stored in amber coloured bottles at −20° C. under argon atmosphere and used without further purification. $^1$H NMR (D$_2$O) δ 1.12 (t, J=7.3 Hz, 6H, N(CH$_2$CH$_3$)$_2$), 2.93 [q, J=7.3 Hz, 4H, N(CH$_2$CH$_3$)$_2$]. m.p. 200-202° C.

Example 2

Nitric Oxide Release from Compounds 14 to 19 In Vitro and by P. aeruginosa Extracts Nitric oxide release from compounds 14 to 19 was detected using the nitric oxide specific probe ISO-NOP with an Apollo 4000 analyser (World Precision Instruments). The nitric oxide probe, which was freshly calibrated using a solution of SNAP according to the manufacturer's instructions, was immersed in a vial containing Tris buffer at pH 7.0 and continuously stirred at room temperature. Various reagents were added successfully while monitoring nitric oxide levels.

Referring to FIG. 1, low μM concentrations of nitric oxide were shown to be released from all of the cephalosporin-3'-diazeniumdiolate free acids 14 to 19 when exposed in aqueous buffer (pH 7) to a commercially available β-lactamase (penicillinase, Sigma Aldrich). Nitric oxide release could not be detected when the enzyme was added without cephalosporin-3'-diazeniumdiolate (data not shown). Similarly, when cephalothin alone (closely related to the β-lactam antibiotic backbone of the cephalosporin-3'-diazeniumdiolates) was used instead of a cephalosporin-3'-diazeniumdiolate, no release of nitric oxide was observed in the presence or absence of penicillinase (data not shown).

Figure 2:
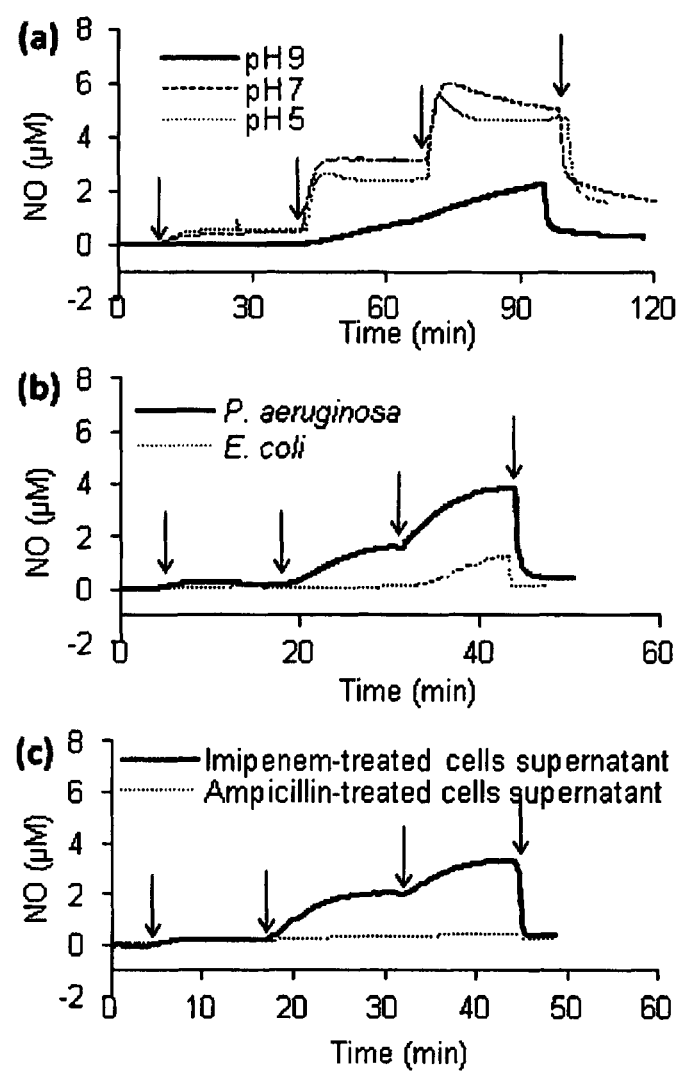
FIG. 2. Amperometric characterization of nitric oxide release from Compound 15. (a) Nitric oxide release in the presence of penicillinase at varying pH. Arrows indicate addition of the following to a reaction vial containing 10 mL Tris buffer at pH 9.0 (thick line), 7.0 (dashed line) or 5.0 (dotted line): (i) 10 μL of 150 mM Compound 15, (ii) 5 μL of 0.1 U/μL penicillinase, (iii) 10 μL of 0.1 U/μL penicillinase, (iv) 80 μL of 10 mM free radical scavenger PTIO. (b) Nitric oxide release in the presence of β-lactamase-expressing $P.$ $aeruginosa$ (thick line) or non-β-lactamase-expressing $E.$ $coli$ (dotted line) cell extracts. Arrows indicate addition of the following to a reaction vial containing 10 mL Tris buffer at pH 7.0: (i) 10 μL of 150 mM Compound 15, (ii) 100 μL cell extract, (iii) 200 μL cell extract, (iv) PTIO. Nitric oxide was undetectable in the presence of penicillinase (1 U/mL) or a representative non-nitric oxide releasing cephalosporin cefalotin (150 μM) either alone or from cefalotin/penicillinase mixtures (data not shown). The data is representative of at least three independent experiments. (c) Nitric oxide release in the presence of supernatants of $P.$ $aeruginosa$ cultures grown for 5 h in the absence of antibiotic then treated for 1 h with extracellular β-lactamase-inducing imipenem a 0.5 μg/ml (thick line) or ampicillin at 100 μg/ml (dotted line). Arrows indicate addition of the following to a reaction vial containing 10 mL Tris buffer at pH 7.0: (i) 10 μL of 150 mM Compound 15, (ii) 500 μL supernatant, (iii) 500 μL supernatant, (iv) PTIO. Addition of 500 μl of 100 μg/ml ampicillin to the vials with imipenem-treated cells supernatant did not inhibit nitric oxide release from Compound 15. (data not shown).

The release of nitric oxide by cleavage of compound 15 was studied further using β-lactamase producing P. aeruginosa extracts. P. aeruginosa cells were grown in the presence of subinhitory concentrations of ampicillin (50 μg/ml) to induce β-lactamase activity. β-lactamase producing P. aeruginosa cells were then lysed using CelLytic reagents (Sigma) and cell extracts were added to a 10-ml-solution of compound 15 while monitoring nitric oxide production using the nitric oxide electrode. FIG. 2a shows that release of nitric oxide from compound 15 triggered by penicillinase varies slightly between pH 5 and 7, while at pH 9 nitric oxide release is greatly reduced. FIG. 2b shows that nitric oxide is released from compound 15 following treatment with β-lactamase expressing P. aeruginosa cell extracts, and that a smaller yet measurable release of nitric oxide from compound 15 occurs upon treatment with non-β-lactamase expressing E. coli cells. This suggests that biofilm-forming bacteria that do not express β-lactamase may also be induced to disperse by triggering cephalosporin-3'-diazeniumdiolates to release nitric oxide, possibly via reaction with transpeptidases, the principal target of bactericidal cephalosporin antibiotics.

Cephalosporin-3'-diazeniumdiolates may be expected to release nitric oxide better if the biofilm bacteria being targeted secrete extracellular β-lactamases, as opposed to expressing β-lactamases that are more typically localised in the periplasmic space of cells, which in biofilms would make the enzymes potentially inaccessible to compounds. FIG. 2c shows that P. aeruginosa can be induced to express extracellular β-lactamases that trigger release of nitric oxide from compound 15 by pre-treatment with the β-lactam antibiotic imipenem. The same induction of extracellular β-lactamase is not apparent with all β-lactam antibiotics, as evidenced in FIG. 2c by the failure of ampicillin to induce expression. Thus, imipenem pretreatment affords extracellular β-lactamase expression, which subsequently leads to increased nitric oxide release from cephalosporin-3'-diazeniumdiolates.

Example 3

Induction of Nitric Oxide Release from Compound 21 in P. aeruginosa Cells

To study nitric oxide release in intact cells of P. aeruginosa, the P. aeruginosa NSGFP reporter strain was used (Barraud et al., 2009). This strain harbours a gene reporter construct that expresses green fluorescent protein (GFP) when the nitric oxide-inducible nirS gene is expressed. P. aeruginosa NSGFP cells were grown with or without ampicillin at subinhibitory concentration (50 μg/ml) to induce β-lactamase activity. Aliquots of 3 ml bacterial culture were then incubated with compound 21, the known nitric oxide donor sodium nitroprusside (SNP), cephalothin (Sigma ref# C4520) or penicillinase for 2 h, before measuring the GFP fluorescence of NSGFP cells.

Figure 3:
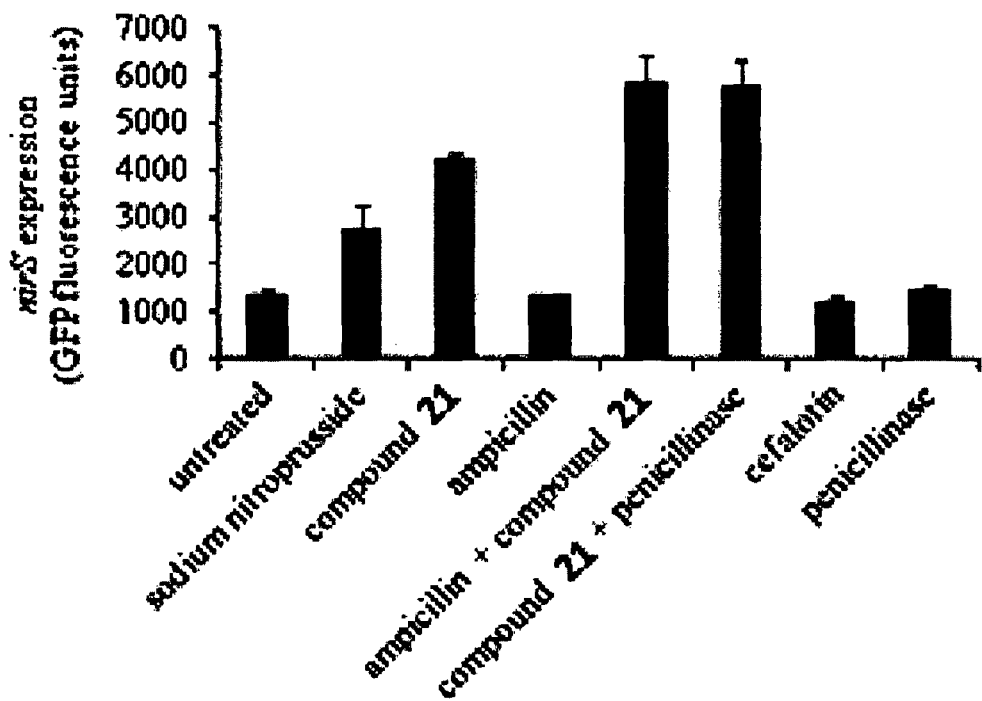
FIG. 3. Compound 21 induces a nitric oxide-dependent genetic response in a $P.$ $aeruginosa$ NSGFP reporter strain. NSGFP cells grown with or without sub-inhibitory ampicillin (50 μg/mL) were exposed to the spontaneous nitric oxide donor sodium nitroprusside (150 μM), compound 21 (150 μM), compound 21 (150 μM) plus penicillinase (0.2 U/mL), a representative non-nitric oxide releasing cephalosporin cefalotin (150 μM) or penicillinase (0.2 U/mL), or left untreated.

As shown in FIG. 3 compound 21 (150 μM) alone induced a GFP-response greater than the response triggered by SNP in P. aeruginosa cells with or without pre-activation of β-lactamase activity. Moreover, compound 21 cleavage and nitric oxide availability to bacteria were enhanced when P. aeruginosa β-lactamase activity was induced by treatment with a subinhibitory concentration of ampicillin. The enhanced response was equivalent to that observed when compound 21 was co-administered with penicillinase to cells grown in the absence of ampicillin. Control treatments that consisted of penicillinase alone or cephalothin had no effect on GFP fluorescence in the NSGFP reporter assay.

Example 4

Release of Nitric Oxide from Compound 21 Induces Biofilm Dispersal

*P. aeruginosa* PAO1 wild type ATCC and MA67 strains, *P. aeruginosa* FRD1, a mucoid, cystic fibrosis (CF) isolate (Oilman and Chakrabarty, 1981), and the clinical strain *P. aeruginosa* 18A, which was isolated from CF sputum samples of chronically infected individual in Tasmania (Kirov et al, 2007) were used for biofilm dispersal assays. Biofilms were grown in M9 minimal medium (containing 48 mM $Na_2HPO_4$, 22 mM $KH_2PO_4$, 9 mM NaCl, 19 mM $NH_4Cl$, pH 7.2, 2 mM $MgSO_4$, 20 mM glucose, and 100 µM $CaCl_2$) in 24-well plates batch cultures at 37° C. with shaking at 200 rpm. After 6 h incubation for PAO1 wild-type biofilms or 24 h incubation for FRD1 and 18A biofilms, treatments were added to each well in less than 1 min per plate and the plates were incubated for a further 10 min at 37° C. with shaking at 200 rpm. Planktonic biomass was quantified by direct measurement of $OD_{600}$ of the supernatant, and the remaining biofilm biomass was quantified by crystal violet staining (O'Toole and Kolter, 1998).

Figure 4:
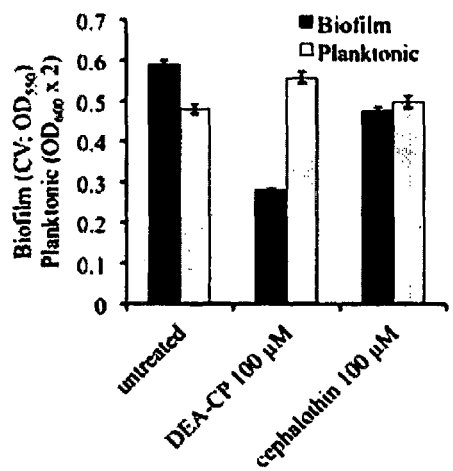
FIG. 4. Compound 21 (denoted as "DEA-CP" in the figure) induces rapid dispersal in $P.$ $aeruginosa$ biofilms. Exposure of preestablished biofilms to Compound 21 for 10 min induces a concomitant decrease in biofilm biomass (dark gray bars) and increase in planktonic biomass (light gray bars). Error bars represent standard error; n=6.

As shown in FIG. 4 Compound 21 (denoted as "DEA-CP") is potent at inducing dispersal of preestablished biofilms of *P. aeruginosa*. After 10 min exposure, the biofilm biomass, as measured with CV staining, was reduced by 55%, while the planktonic biomass, as measured by measurements of $OD_{600nm}$ of the supernatants, simultaneously increased by 20% compared to controls that were left untreated (P<0.01, 1-way ANOVA and Tukey's multiple comparison test). In contrast, cephalothin alone did not induce significant dispersal events.

Figure 5:
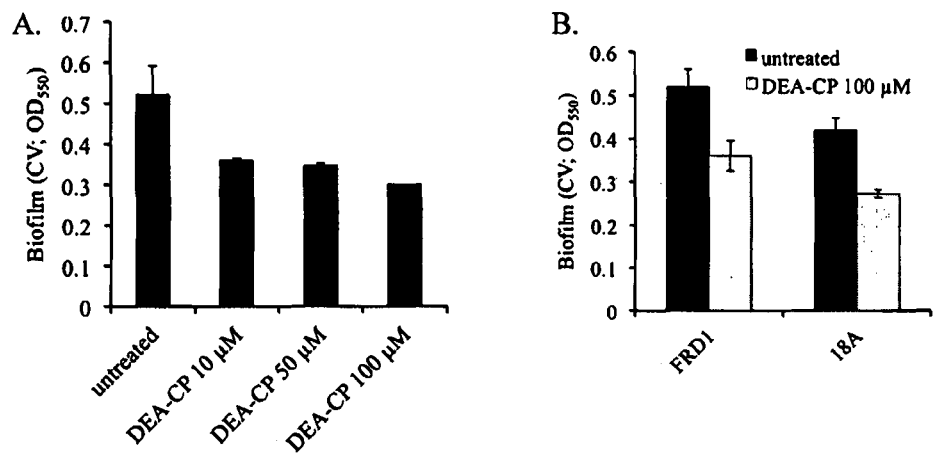
FIG. 5. Compound 21 (denoted as "DEA-CP" in the figure) induces rapid dispersal in $P.$ $aeruginosa$ biofilms in a dose dependent manner (A). Biofilms of $P.$ $aeruginosa$ CF isolates strains grown of 24 h also disperse after exposure to Compound 21 for 10 min (light gray bars) compared to biofilms that were left untreated (dark gray bars) (B). Error bars represent standard error, n=2.

Compound 21 was then tested in a range of concentrations against *P. aeruginosa* PAO1 wild type biofilms. As shown in FIG. 5 Compound 21 (denoted as "DEA-CP") induces dispersal in a dose dependent manner in the range 10-100 µM (FIG. 5A). Compound 21 was also tested against biofilms of *P. aeruginosa* CF isolate strains FRD 1 and 18A grown for 24 h. Exposure to 100 µM Compound 21 for 10 min induced 30% and 35% dispersal in FRD1 and 18A biofilms, respectively, as measured by CV staining (FIG. 5B).

Figure 6:
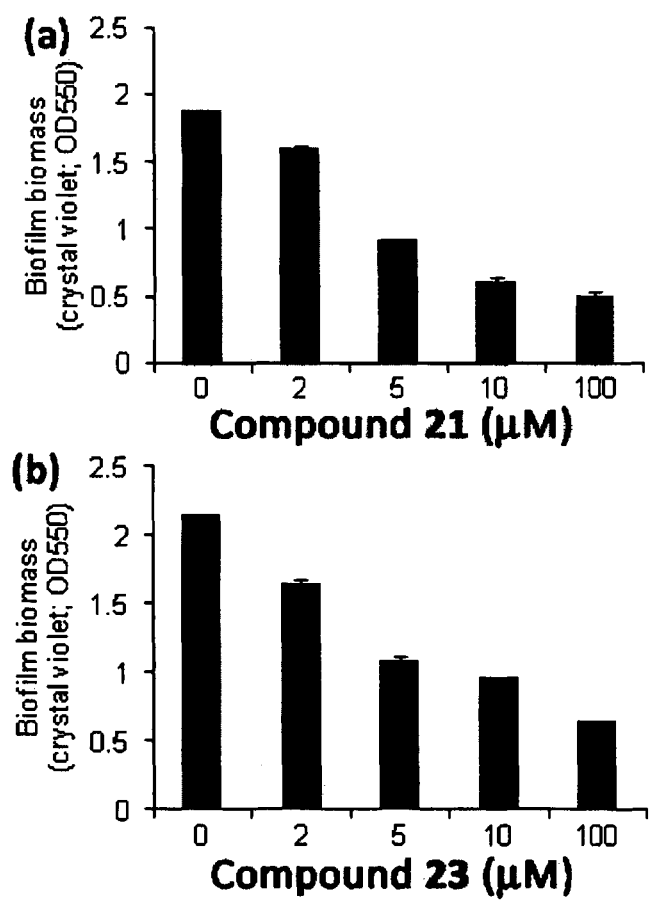
FIG. 6. Dose-dependent dispersal of $P.$ $aeruginosa$ biofilms by compounds 21 (a) and 23 (b). $P.$ $aeruginosa$ biofilms were grown in microtiter plates with shaking at 37° C. and pre-treated with imipenem (0.5 μg/mL) for 1 h before exposing to various concentrations of compounds for 15 mins. Remaining biofilm mass was quantified by crystal violet staining.

The dispersal of pre-established *P. aeruginosa* biofilms (using strain MA67 that forms better biofilms than the strain used in experiments described above) by compound 21 and its analogue (compound 23) was further assessed and shown to be dose dependent (see FIG. 6).

Figure 7:
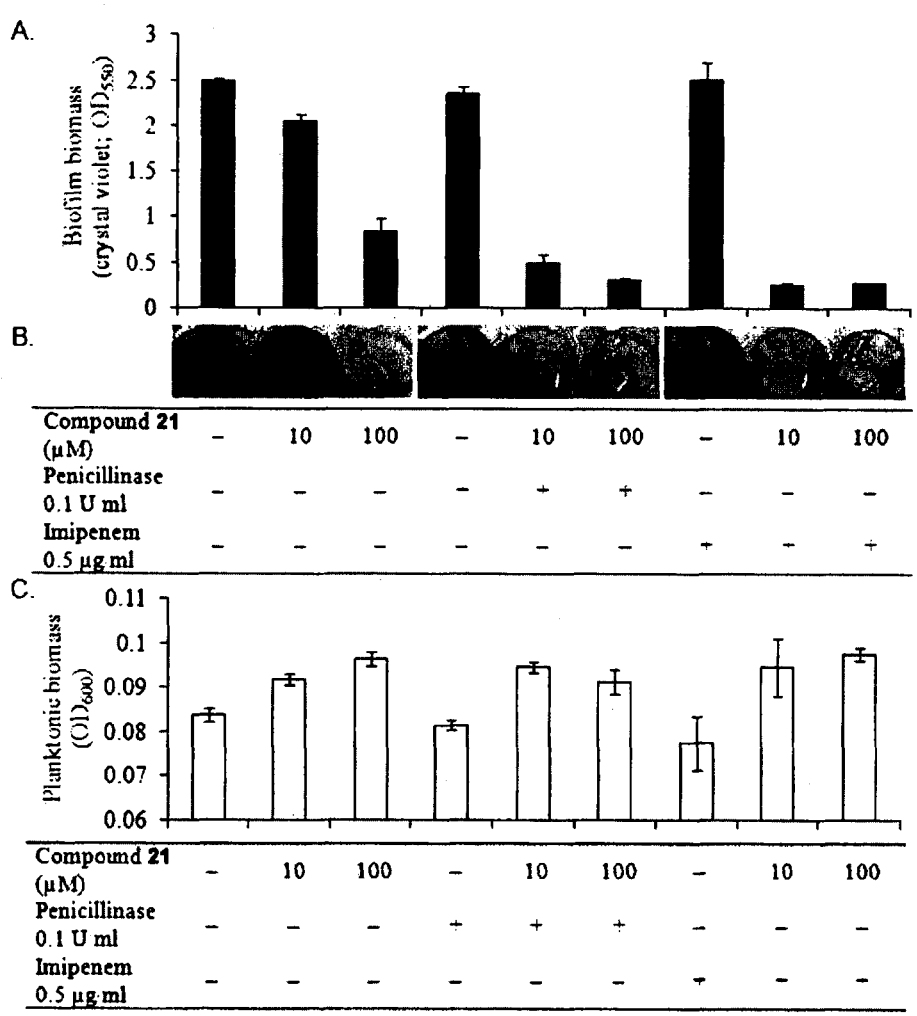
FIG. 7. Upon reaction with β-lactamase, Compound 21 induces a rapid dispersal response in $P.$ $aeruginosa$ biofilms. (A) Biofilms were quantified by crystal violet staining. (B) Pictures of crystal-violet-stained biofilms. (C) Planktonic cells were quantified by $OD_{600}$ measurement of the supernatant. Error bars indicate standard errors (n=2). In these experiments, biofilm dispersal is supported by the increase in planktonic OD readings that correspond with decreases in crystal violet staining of biofilms.

Further experiments with compound 21 demonstrated the enhanced biofilm-dispersion effects in *P. aeruginosa* after induction of extracellular β-lactamase expression through pre-treatment of biofilms with imipenem (see FIG. 7). In these experiments, pre-established *P. aeruginosa* biofilms were grown in microtiter plates with shaking at 37° C. and treated with compound 21 at 10 µM and 100 µM in the presence or absence of penicillinase (0.1 U/mL) for 15 min or left untreated. Pre-established *P. aeruginosa* that were pre-treated with imipenem at 0.5 µg/mL for 1 h to induce release of extracellular β-lactamase were then exposed to compound 21 at 10 µM and 100 µM for 15 min.

Figure 8:
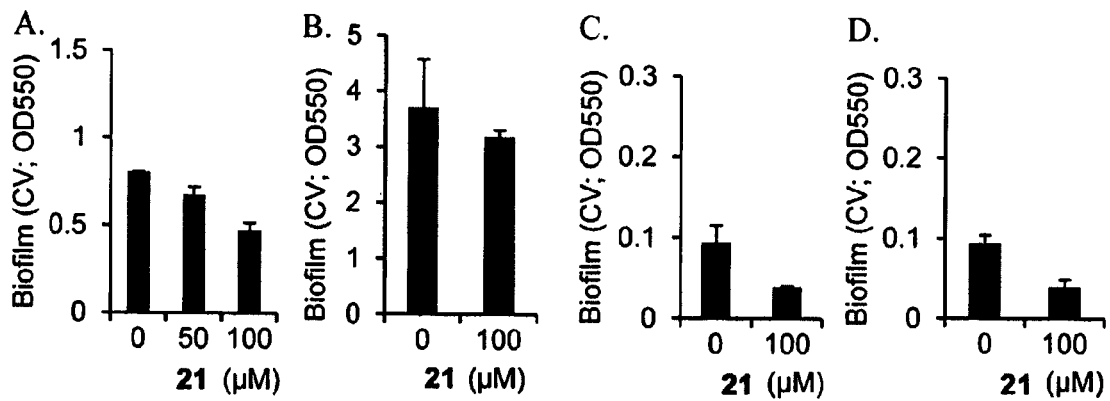
FIG. 8. Compound 21 induces rapid dispersal (10 min after treatment) in biofilms of various Gram-negative bacteria: (A) $Escherichia$ $coli$, (B) $Vibrio$ $cholerae$, (C) $Serratia$ $marcescens$; and Gram-positive bacteria: (D) $Staphylococcus$ $aureus$.

The inventors then investigated the ability of compound 21 to induce dispersal of biofilms from other Gram negative bacterial species (*Escherichia coli, Vibrio cholerae* and *Serratia marcescens*) and the Gram positive species *Staphylococcus aureus*. As shown in FIG. 8, compound 21 induces rapid dispersal (10 min after treatment) in biofilms of these species.

Figure 9:
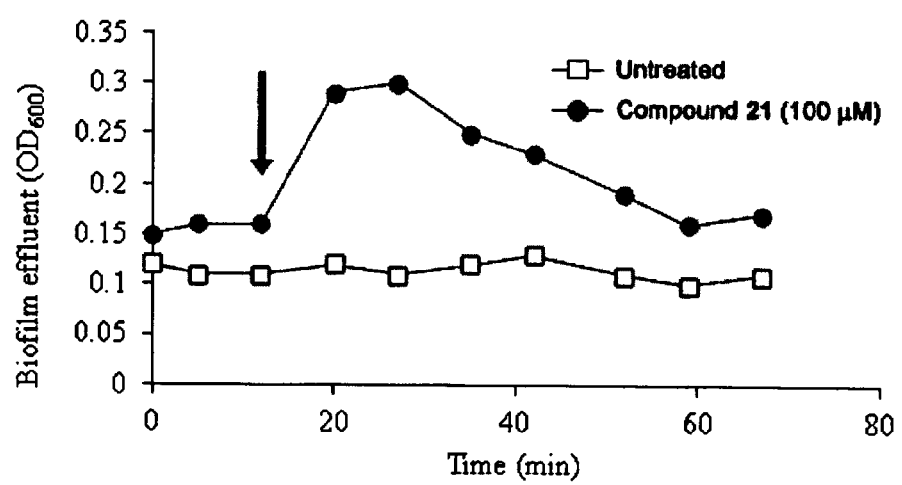
FIG. 9. Compound 21 induces dispersal of $P.$ $aeruginosa$ PAO1 biofilms grown in glass microfermentors under continuous flow conditions. After 24 h growth, $OD_{600}$ measurements of the biofilm effluent showed a substantial increase in released cells after addition of compound 21, while the amount of released cells from untreated biofilms remained unchanged. Arrow indicates addition of compound. Data is representative of two independent experiments.

The biofilm dispersing properties of compound 21 were further investigated using continuous-flow biofilm culture assays. *P. aeruginosa* PAO1 biofilms were established in glass microfermenters receiving a continuous flow of fresh M9 minimal medium. The inlet was switched to vessels containing fresh medium, with or without compound 21 (100 µM), and $OD_{600}$ measurements of the effluent taken. A rapid and significant increase in released cells was observed after addition of compound 21, while the amount of cells released from untreated biofilms remained unchanged (FIG. 9).

Example 5

Minimum Inhibitory Concentration of Compound 21

*P. aeruginosa* PAO1 wild type cells were grown in M9 minimal medium in 96-well plates at 37° C. under static conditions in the presence of a range of concentrations of Compound 21 diethylamine diazeniumdiolate (DEA; nitric oxide donor used for synthesis of Compound 21), and/or the antibiotics cephalothin, ceftazidime and tetracycline. Planktonic growth was quantified at various time points by direct measurement of $OD_{600}$ of the supernatant. The minimum inhibitory concentration (MIC) for antibiotic treatments was defined as the concentration of antibiotic that resulted in an $OD_{600nm}$ of 35% or less after 20 h growth. For biofilm viability experiments, *P. aeruginosa* biofilms were grown in 24-well microtitre plates as described above (see Example 4) for 7 h, before adding treatments of Compound 21 and antibiotics at the indicated final concentrations and incubating for another 1 h or 2 h under normal culture conditions. For each time point, planktonic bacteria were collected, serially diluted in sterile phosphate-buffered saline (PBS) and spread on LB agar plates. Biofilms were gently rinsed once with PBS and resuspended from the wall and bottom well surfaces (total surface area=4.4 $cm^2$) using a sterile cotton swab. Bacterial aggregates were further disrupted in a bath sonicator for 10 min. Biofilm bacteria were then serially diluted and spread on LB agar plates. Colony forming units (CFU) were determined after 1 day incubation at 37° C.

Figure 10:
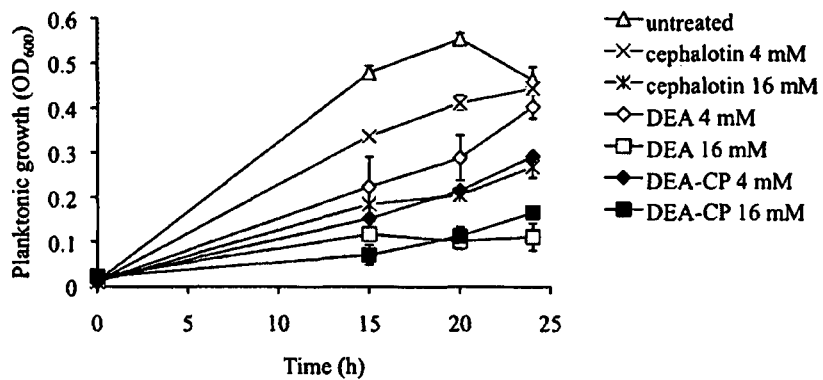
FIG. 10. Planktonic growth inhibition by cephalothin, DEA and Compound 21 (denoted as "DEA-CP" in the figure) in wild type $P.$ $aeruginosa$. The graph only shows data for concentrations at 4 mM and 16 mM; lower concentrations had no effect and higher concentrations completely inhibited growth for all 3 compounds. Error bars indicate standard error; n=2.

Compound 21 alone was found to be more potent at inhibiting *P. aeruginosa* planktonic growth with a MIC of 4 mM compared to cephalothin or DEA, which were both found to have an MIC of 16 mM (FIG. 10 Compound 21 denoted as "DEA-CP"). The growth inhibitory effects of Compound 21 are likely due to toxic levels of nitric oxide, and its increased toxicity compared to DEA is suggested to be the result of targeted release of nitric oxide within bacteria.

Example 6

Combinatorial Treatments Involving Compound 21 and Antibiotics

Figure 11:
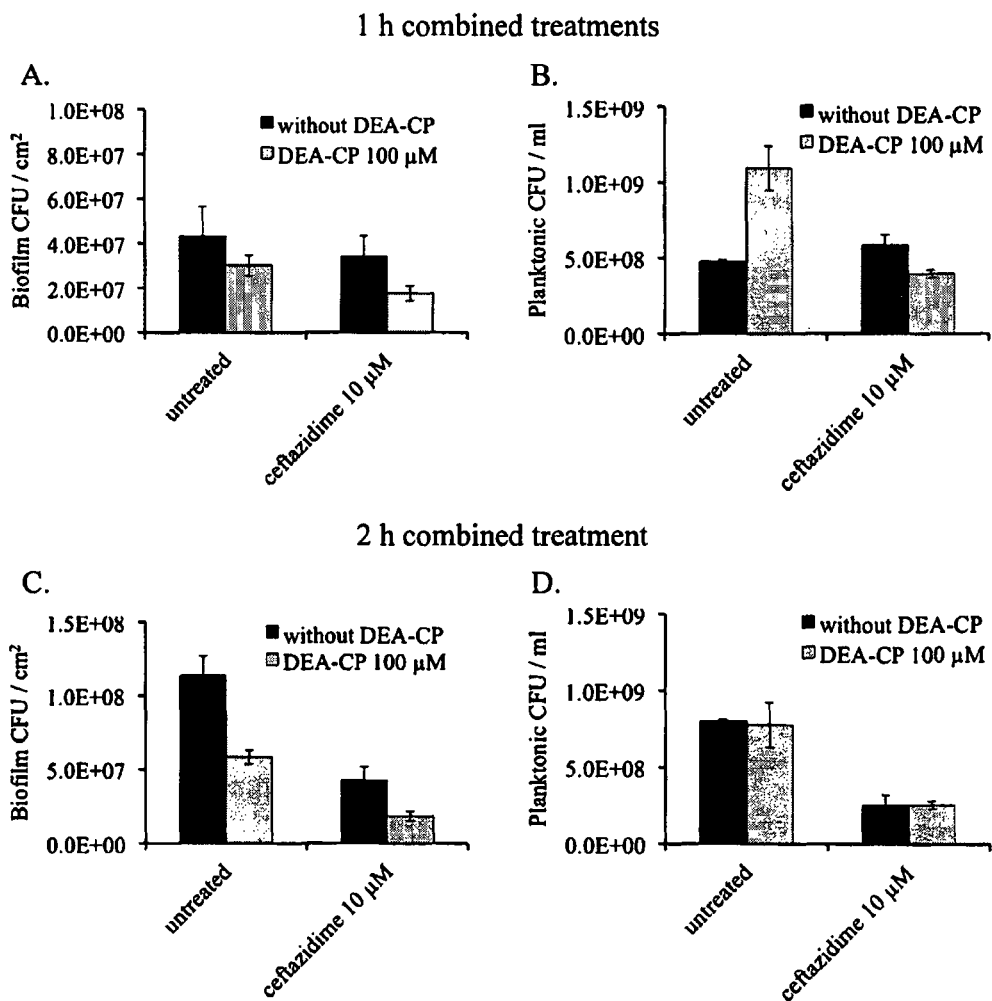
FIG. 11. Effect of combined treatments of Compound 21 (denoted as "DEA-CP" in the figure) an antibiotic on viability of $P.$ $aeruginosa$ biofilm and planktonic cells. Preestablished biofilms grown in wells of microtiter plates were exposed, in the presence or absence of Compound 21, to ceftazidime or left untreated. After 1 h (A, B) or 2 h (C, D) treatments, supernatants were collected and planktonic CFU were enumerated (B, D); biofilm bacteria were resuspended in buffer and biofilm CFU enumerated (A, C). Error bars indicate standard error; n=2.

To assess the effect of Compound 21 and antibiotics on the viability of biofilm and dispersed cells, combinatorial treatments of Compound 21 with ceftazidime were carried out on biofilms grown in microtitre plates (as described above in Example 5), and both biofilm CFU and planktonic CFU were determined. The results demonstrate a concomitant decrease in biofilm CFU, from $1.9 \times 10^8$ to $1.3 \times 10^8$ CFU per well, and increase in planktonic CFU, from $4.8 \times 10^8$ to $11 \times 10^8$ CFU per well, after 1 h treatment with Compound 21 100 µM alone (see FIGS. 11A and 11B), which is consistent with OD and CV measurements previously obtained (see Example 4; FIG. 4). Further, the efficacy of 10 µM ceftazidime against both biofilm and planktonic bacteria was increased when incubated in the presence of Compound 21 for 1 h compared to biofilm and planktonic bacteria that were treated with ceftazidime alone (FIGS. 8A and 8B). The efficacy of ceftazidime against biofilm bacteria was also increased by 2.3-fold in the presence of Compound 21 after 2 h treatments compared to biofilms that were treated without Compound 21 (FIG. 11C).

The inventors further found that compound 21 potentiates the anti-biofilm efficacy of the clinically employed antibiotics tobramycin and ciprofloxacin (Table 1). Established *P. aeruginosa* biofilms grown in microtiter plates with shaking at 37° C. were pre-treated with sub-inhibitory imipenem (10 µg/mL) for 1 h to induce release of extracellular β-lactamase. Tobramycin or ciprofloxacin were then added either with or without compound 21, or biofilms were left untreated (controls). Biofilm bacteria were incubated for a further 1 h before resuspension and enumeration of cfu. Values represent the log-fold reductions in cfu compared to control biofilms and are the mean of two independent experiments (±SEM). Bacteria in the supernatants were fully eradicated (below the detection limit; 10 cfu/mL) after treatment with either antibiotic alone or either antibiotic in combination with compound 21.

TABLE 1

| Antibiotic | Compound 21 (µM) | Log Reduction in Biofilm cfu |
|---|---|---|
| Tobramycin | 0 | 2.15 ± 0.16 |
| 80 µg/mL/170 µM | 10 | 3.92 ± 0.06 |
|  | 100 | 3.58 ± 0.15 |
| Ciprofloxacin | 0 | 3.54 ± 0.09 |
| 5 µg/mL/15 µM | 10 | 5.06 ± 0.02 |
|  | 100 | 4.90 ± 0.13 |

In combinational treatments with tetracycline, against planktonic *P. aeruginosa* Compound 21 increased the inhibitory effects of 6 µM tetracycline by 45% and the inhibitory effects of 25 µM tetracycline by 60% (data not shown).

References

Barraud N, et al. (2009) Nitric oxide signaling in *Pseudomonas aeruginosa* biofilms mediates phosphodiesterase activity, decreased cyclic di-GMP levels, and enhanced dispersal. *J. Bacteriol*. 191(23):7333-7342.

Hope et al, 2002, Determining the spatial distribution of viable and non viable bacteria in hydrated microcosm dental plaques by viability profiling, *J. Appl. Microbiol.*, 1993: 448-455.

Kirov S M, et al. (2007) Biofilm differentiation and dispersal in mucoid *Pseudomonas aeruginosa* isolates from patients with cystic fibrosis. *Microbiology* 153 (Pt 10):3264-3274.

Ohman D E & Chakrabarty A M (1981) Genetic mapping of chromosomal determinants for the production of the exopolysaccharide alginate in a *Pseudomonas aeruginosa* cystic fibrosis isolate. *Infect. Immun*. 33(1):142-148.

O'Toole G A & Kolter R (1998) Initiation of biofilm formation in *Pseudomonas fluorescens* WCS365 proceeds via multiple, convergent signalling pathways: a genetic analysis. *Mol. Microbiol*. 28(3):449-461.

Webb et al, 2003, Cell death in *Pseudomonas aeruginosa* biofilm development, *J. Bact.*, 185: 4585-4592.

The invention claimed is:
1. A compound of the formula (I), or a salt thereof:

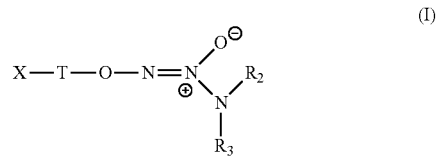

wherein T is a bond or a bivalent hydrocarbon having between 1 and 6 carbon atoms, $R_2$ and $R_3$ are independently selected from: hydrogen, $C_3$-$C_7$ cycloalkyl, $C_3$-$C_7$ cycloalkenyl, $(CH_2)_pOC(O)PhOC(O)C_1$-$C_6$alkyl, $(CH_2)_pOC(O)APhC_1$-$C_6$alkyl, branched or straight chain $C_1$-$C_{20}$ alkyl, branched or straight chain $C_2$-$C_{20}$ alkenyl, branched or straight chain $C_2$-$C_{20}$ alkynyl, wherein the alkyl, alkenyl or alkynyl chains may optionally be interrupted by one or more groups/heteroatoms selected from O, S, NH, $NH_2^+$, and wherein the alkyl, alkenyl or alkynyl groups may optionally be substituted by one or more substituents selected from the group consisting of: halogen, cyano, COOH, $(CH_2)_pC(O)OC_1$-$C_6$alkyl, $C(O)OC_1$-$C_6$alkenyl, $SO_3H$, $SO_2$halogen, $SO_2NH_2$ $NH_2$, $NH_3^+$, OH, SH, $OC_1$-$C_6$alkyl, $OC_2$-$C_6$alkenyl, $OC_2$-$C_6$alkynyl, aryl and heteroaryl, or alternatively $R_2$ and $R_3$, together with the nitrogen to which they are attached, form a 4-, 5-, 6-, 7- or 8-membered ring which may optionally contain 1, 2, 3, 4, 5 or 6 additional nitrogen atoms and may be saturated, unsaturated or partially unsaturated, and wherein the 4-, 5-, 6-, 7- or 8-membered ring may optionally be substituted by one or more substituents selected from the group consisting of: —C(O)$C_1$alkylene-naphthyl-O$C_1$-$C_6$alkyl, —C(O)$C_1$-$C_3$alkylene-Ph-C(O)-Ph, —C(O)CH$_2$O(CH$_2$)$_p$OCH$_3$, —C(O)OPhNO$_2$, —C(O)OPhNH$_2$, —C(O)O(CH$_2$)$_p$Chalogen$_3$, —C(O)O(CH$_2$O)$_p$CH$_3$, $C_1$-$C_6$-alkyl, $C_2$-$C_6$alkenyl, $C_2$-$C_6$alkynyl, —C(O)$C_1$-$C_6$alkyleneCOO$C_1$-$C_6$alkyl, —C(O)$C_1$-$C_3$alkylenePh$C_1$-$C_6$alkyl, —C(O)O-pyrrolidinyl-2,5-dione, —C(O)$C_1$-$C_3$alkylenePh$C_1$-$C_6$alkyl, —C(O)(CH$_2$)$_p$O$C_1$-$C_6$alkyl, —C(O)(CH$_2$)$_p$halogen, —C(O)O(CH$_2$)$_p$Ph, —(CH$_2$)$_p$SH, —SO$_2$naphthyl-N$C_1$-$C_6$alkyl, —C(O)ON$C_1$-$C_6$alkyl, —(CH$_2$)$_p$OH, —C(O)PhOAc, —C(O)(CH$_2$)$_p$NHC(O)$C_1$-$C_6$alkyl, —C(O)NH$_2$, —C(O)M, —C(O)NR$_4$R$_5$, —(CH$_2$)$_p$CH(OH)CHOH, halogen, cyano, —COOH, —C(O)O(CH$_2$)$_p$Ph, —C(O)O$C_1$-$C_6$alkyl, —C(O)O$C_2$-$C_6$alkenyl, —C(O)O$C_2$-$C_6$alkynyl, —C(O)S$C_1$-$C_6$alkyl, —C(O)S$C_2$-$C_6$alkenyl, —C(O)S$C_2$-$C_6$alkynyl, —C(O)$C_1$-$C_6$alkyl, SO$_3$H, SO$_2$halogen, SO$_2$phenyl, SO$_2$NH$_2$, SO$_2$NR$_4$R$_5$, SO$_2$PhNHCO$C_1$-$C_6$alkyl, NH$_2$, OH, SH, O$C_1$-$C_6$alkyl, O$C_2$-$C_6$alkenyl, O$C_2$-$C_6$alkynyl, aryl and heteroaryl, and wherein A is a bivalent hydrocarbon radical having between 1 and 4 carbon atoms, p is a number between 0 and 4, R$_4$ and R$_5$ independently represent $C_1$-$C_6$alkyl and M is pyridyl, pyrimidinyl, pyrazinyl, phenyl or triazinyl; or wherein R$_2$ and R$_3$ are independently selected from: hydrogen, $C_5$-$C_7$ cycloalkyl, $(CH_2)_pOC(O)PhOC(O)C_1$-$C_6$alkyl, $(CH_2)_pOC(O)APhC_1$-$C_6$alkyl, branched or straight chain $C_1$-$C_{10}$ alkyl, branched or straight chain $C_2$-$C_{10}$ alkenyl and branched or straight chain $C_2$-$C_{10}$ alkynyl, wherein the alkyl, alkenyl or alkynyl chains may optionally be interrupted by between one and three groups/heteroatoms selected from O, S, NH and $NH_2^+$, and wherein the alkyl, alkenyl or alkynyl chains may optionally be substituted by between one and six substituents selected from the group consisting of: halogen, phenyl, ethoxy, methoxy, propoxy, COOH, $(CH_2)_p COOC_1$-$C_4$alkyl, $NH_2$, $NH_3^+$, OH and SH, and wherein A is a bivalent hydrocarbon radical having between 1 or 2 carbon atoms and p is 0, 1 or 2; or wherein $R_2$ and $R_3$ are independently selected from: hydrogen, $C_5$-$C_7$ cycloalkyl, branched or straight chain $C_1$-$C_{10}$ alkyl, branched or straight chain $C_2$-$C_{10}$ alkenyl, branched or straight chain $C_2$-$C_{10}$ alkynyl, wherein the alkyl, alkenyl or alkynyl chains may optionally be interrupted by between one and three groups selected from O, NH and $NH_2^+$, and wherein the alkyl, alkenyl or alkynyl chains may optionally be substituted by between one and four substituents selected from the group consisting of: halogen, phenyl, methoxy, COOH, $CH_2COOC_1$-$C_4$alkyl, $NH_2$ and $NH_3^+$; or wherein $R_2$ and $R_3$ are independently selected from: hydrogen, cyclohexyl, branched or straight chain $C_1$-$C_{10}$ alkyl or branched or straight chain $C_2$-$C_{10}$ alkenyl, wherein the alkyl or alkenyl chains may optionally be interrupted by one or two groups selected from NH and $NH_2^+$, and wherein the alkyl, alkenyl or alkynyl chains may optionally be substituted by between one and three substituents selected from the group consisting of: phenyl, methoxy, COOH, $NH_2$ and $NH_3^+$; or wherein $R_2$ and $R_3$, together with the nitrogen to which they are attached, form a 4-, 5-, 6- or 7-membered ring which may optionally contain 1, 2, 3, 4 or 5 additional nitrogen atoms and may be saturated, unsaturated or partially unsaturated, and wherein the 4-, 5-, 6- or 7-membered ring may optionally be substituted by one or more substituents selected from the group consisting of: $SO_2NMe_2$, $SO_3H$, $SO_2$halogen, $SO_2NH_2$, —C(O)O$(CH_2)_p$Ph, —C(O)Me, —C(O)pyridyl, —$(CH_2)_p$OH, —C(O)$NH_2$, —COOH, —C(O)$NMe_2$, —C(O)$NEt_2$, phenyl, naphthyl, pyridinyl, pyrimidinyl, pyrazinyl, triazinyl, pyrrolidinyl, imidazolyl, $C_1$-$C_6$-alkyl, $C_2$-$C_6$alkenyl, $C_2$-$C_6$alkynyl, —C(O)O$C_1$-$C_6$alkyl, —C(O)O$C_2$-$C_6$alkenyl, —C(O)O$C_2$-$C_6$alkynyl, —C(O)O$(CH_2)_p$Ph, —$(CH_2)_p$SH, halogen, $SO_2$PhNHCO$C_1$-$C_6$alkyl, $NH_2$, SH, O$C_1$-$C_6$alkyl, and wherein p is a number between 0 and 2; or wherein $R_2$ and $R_3$, together with the nitrogen to which they are attached, form a 5-, 6-, or 7-membered ring which may optionally contain 1, 2 or 3 additional nitrogen atoms and may be saturated, unsaturated or partially unsaturated, and wherein the 5-, 6-, or 7-membered ring may optionally be substituted by between one and four substituents selected from the group consisting of: $SO_2NMe_2$, $SO_2NH_2$, —COO$(CH_2)_p$Ph —C(O)Me, —C(O)pyridyl, —$(CH_2)_p$OH, —C(O)$NH_2$, —COOH, —C(O)$NMe_2$, —C(O)$NEt_2$, phenyl, pyridinyl, pyrimidinyl, pyrazinyl, triazinyl, pyrrolidinyl, imidazolyl, $C_1$-$C_6$-alkyl, $C_2$-$C_6$alkenyl, $C_2$-$C_6$alkynyl, —C(O)O$C_1$-$C_6$alkyl, —C(O)O$C_2$-$C_6$alkenyl, —C(O)O$C_2$-$C_6$alkynyl, —C(O)O$(CH_2)_p$Ph, —$(CH_2)_p$SH, halogen, $NH_2$, SH, O$C_1$-$C_6$alkyl, p is a number between 0 and 2; or wherein $R_2$ and $R_3$, together with the nitrogen to which they are attached, form a saturated 5-, 6-, or 7-membered ring which may optionally contain 1, 2 or 3 additional nitrogen atoms, and wherein the 5-, 6-, or 7-membered ring may optionally be substituted by between one and three substituents selected from the group consisting of: $SO_2NMe_2$, $SO_2NH_2$, —C(O)Me, —C(O)pyridyl, —$(CH_2)_p$OH, —C(O)$NH_2$, —COOH, —C(O)$NMe_2$, —C(O)$NEt_2$, phenyl, pyridinyl, pyrimidinyl, pyrazinyl, triazinyl, pyrrolidinyl, imidazolyl, $C_1$-$C_6$-alkyl, $C_2$-$C_6$alkenyl, —C(O)O$C_1$-$C_6$alkyl, —C(O)O$C_2$-$C_6$alkenyl, halogen, $NH_2$, SH, O$C_1$-$C_6$alkyl, p is a number between 0 and 2; or wherein $R_2$ and $R_3$, together with the nitrogen to which they are attached form a structure selected from the group consisting of:

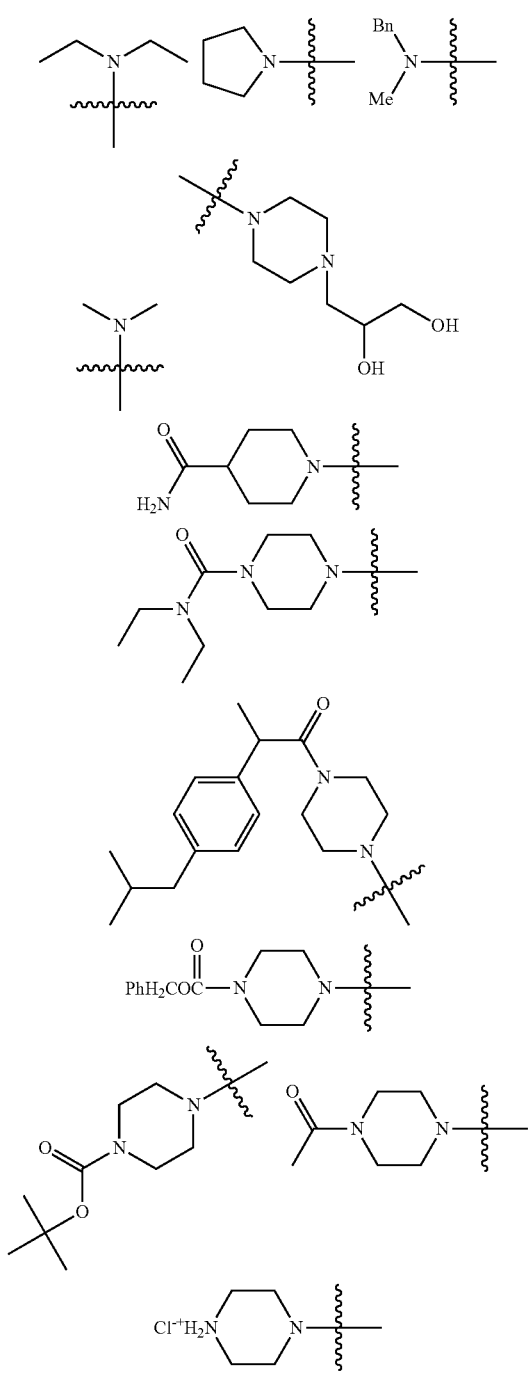

59
-continued
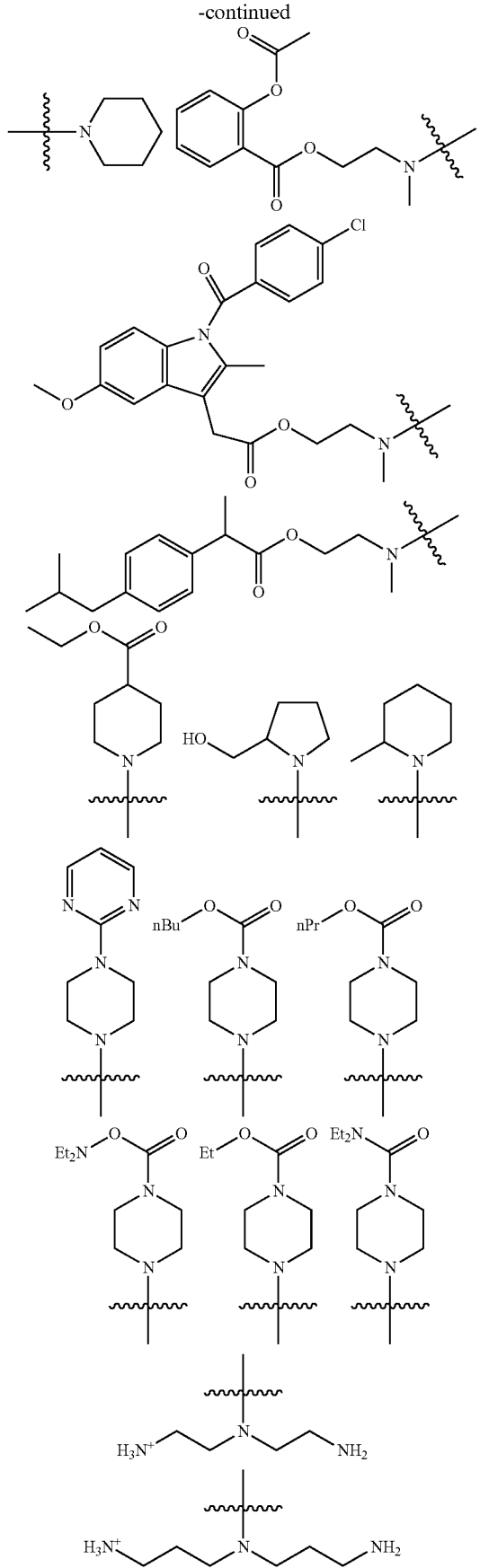
60
-continued
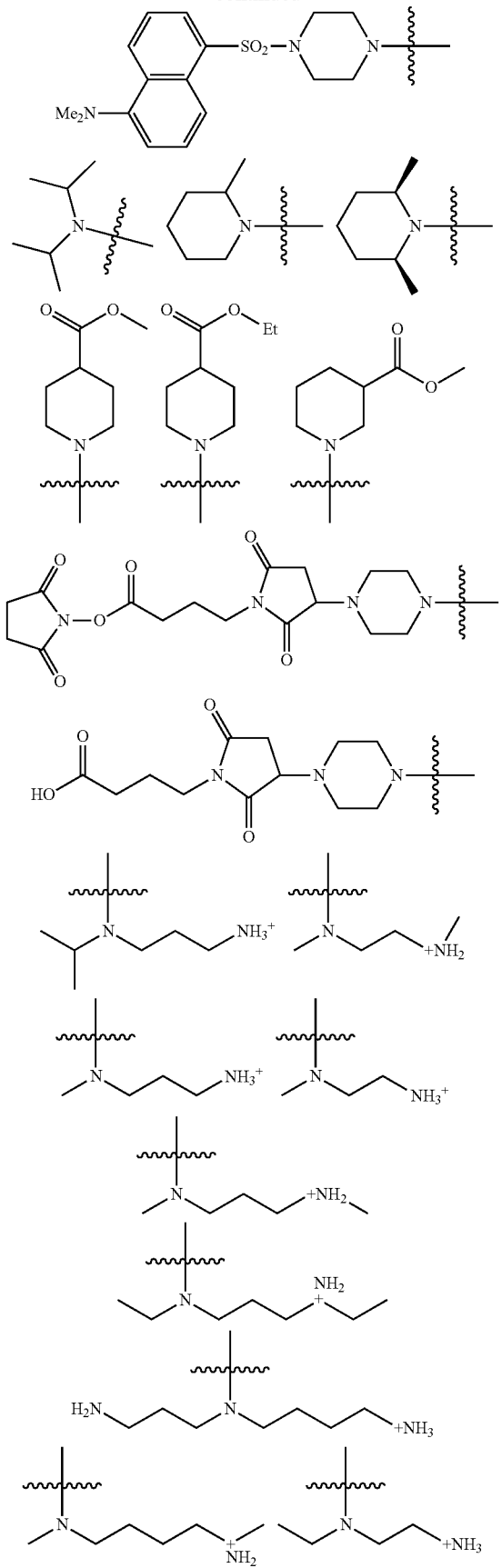

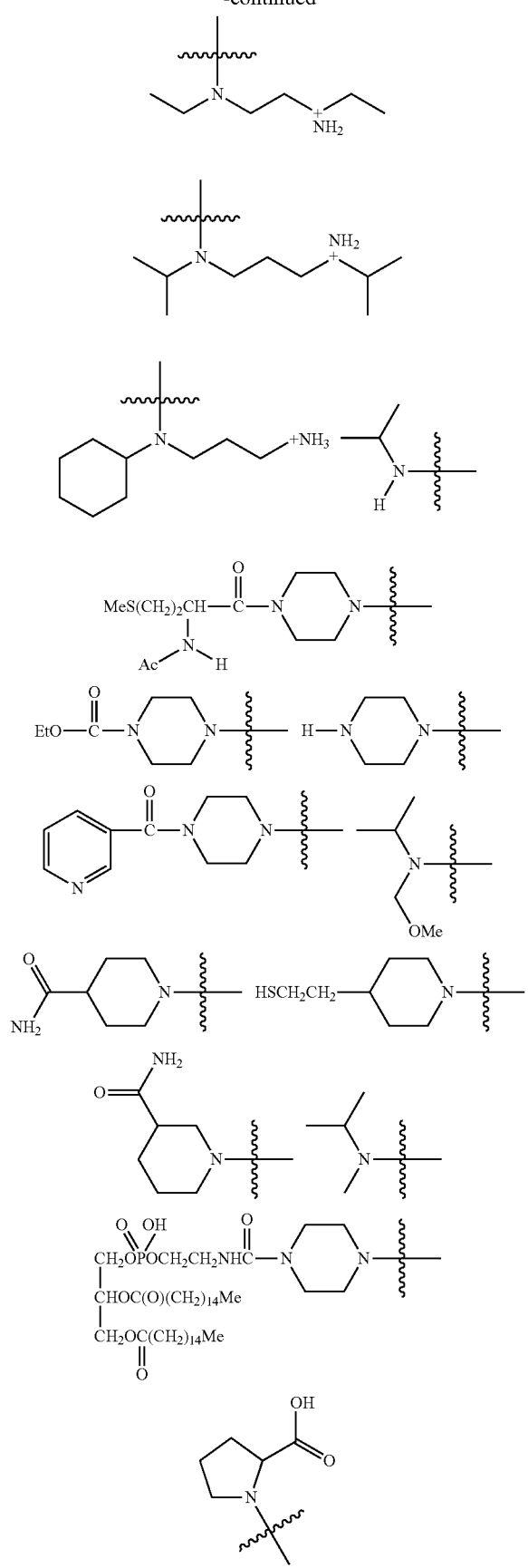
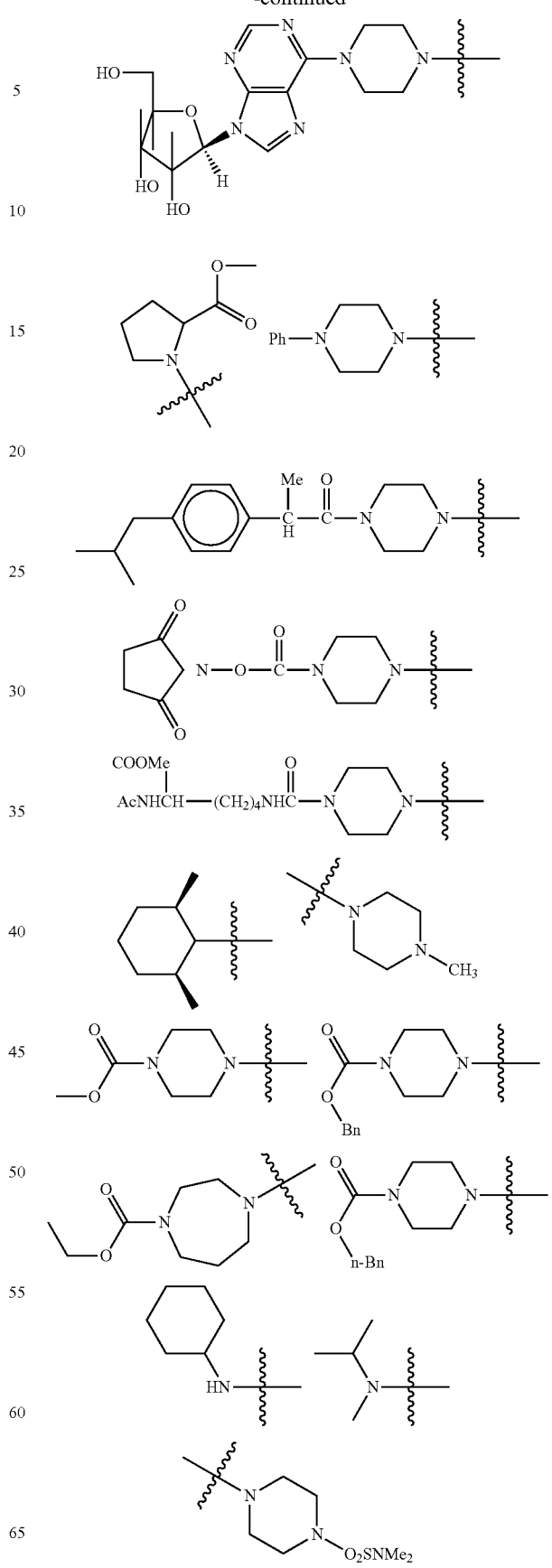

63
-continued
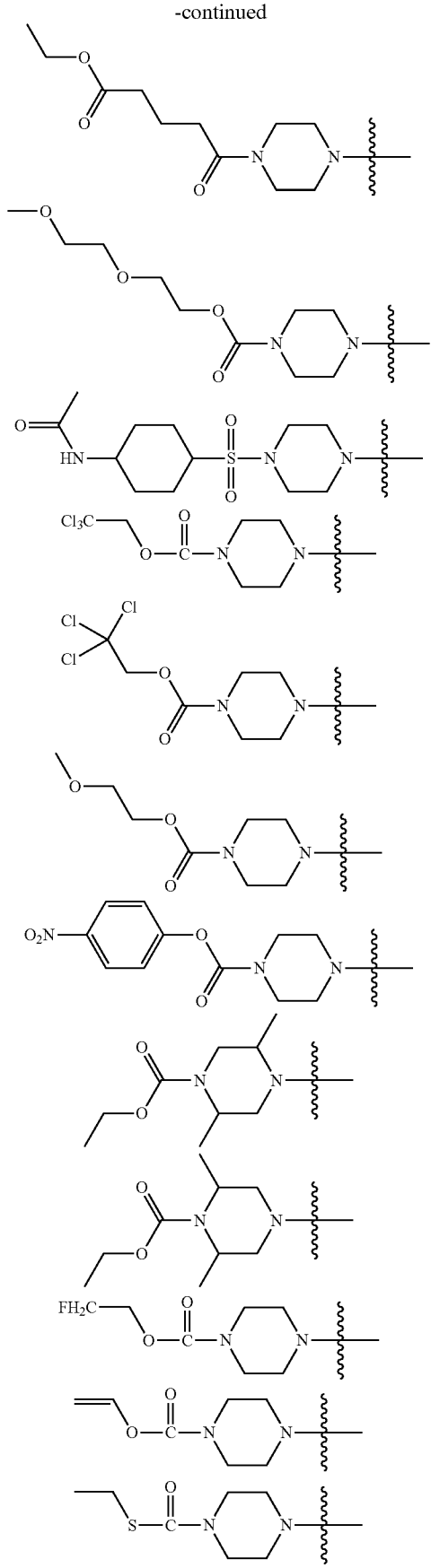
64
-continued
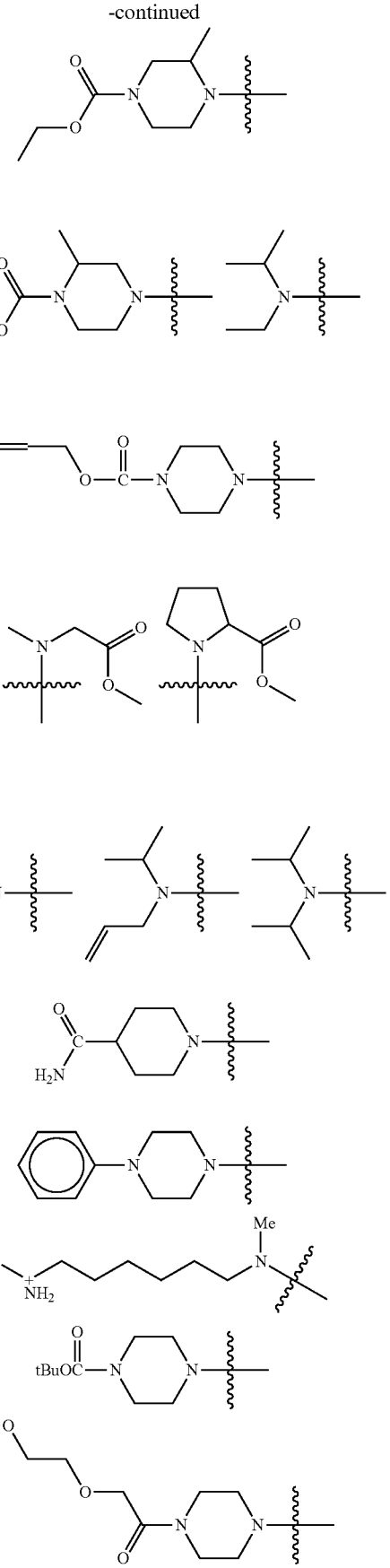

-continued

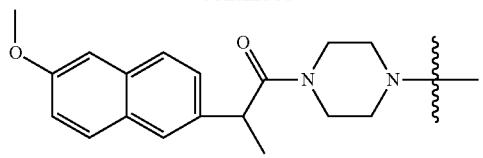

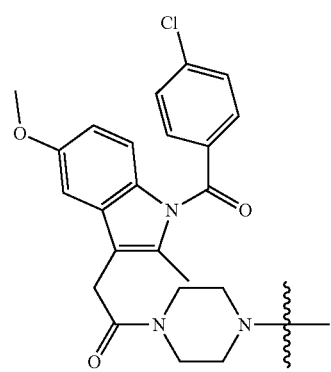

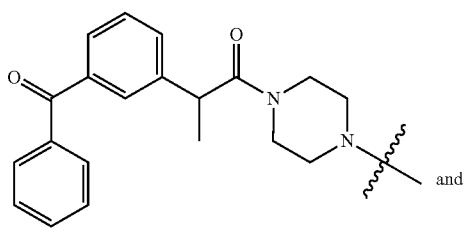

and

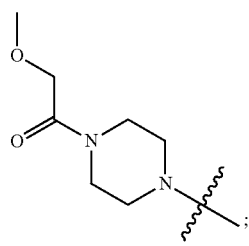

;

or
wherein R₂ and R₃ are independently selected from $C_1$-$C_{10}$ alkyl, or alternatively R₂ and R₃, together with the nitrogen to which they are attached, form a 5- or 6-membered ring which may optionally contain between 1 and 3 additional nitrogen atoms, and which may optionally be substituted with an aryl or heteroaryl group and X is selected from the group consisting of:

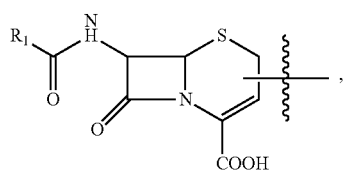

wherein R₁ is a substituent that corresponds to a substituent attached to the 7-NHC(O)— group of a cephalosporin antibiotic; or wherein R₁ is Y-aryl or Y-heteroaryl where Y is a bivalent hydrocarbon having between 1 and 4 carbon atoms.

2. A compound according to claim 1 having the structure:

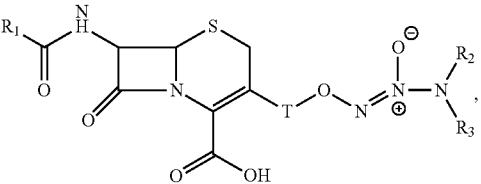

including salts thereof.

3. A compound according to claim 1 having a structure selected from the group consisting of:

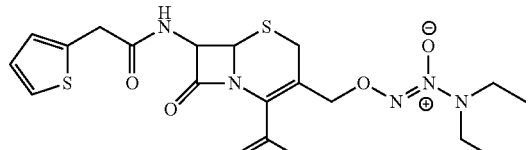

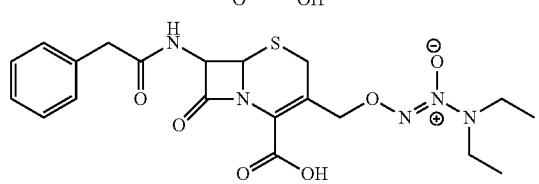

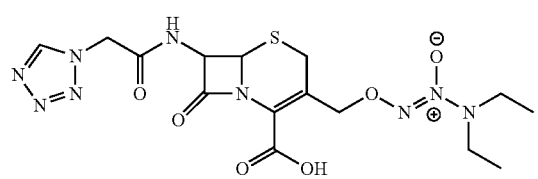

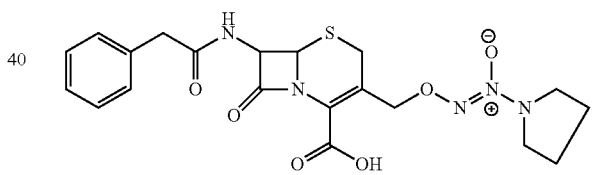

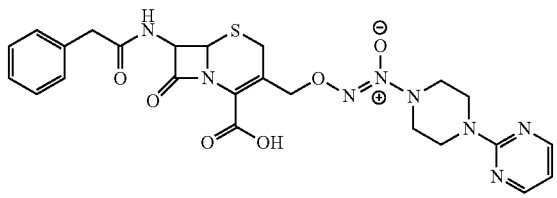

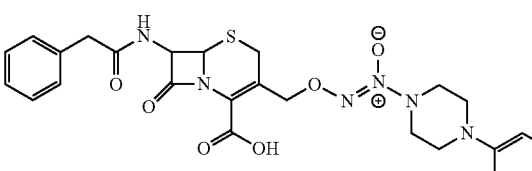

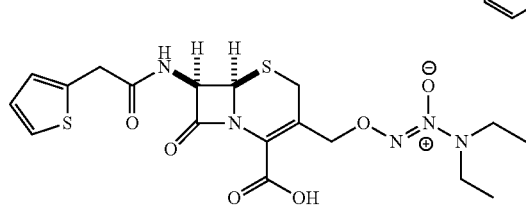

-continued

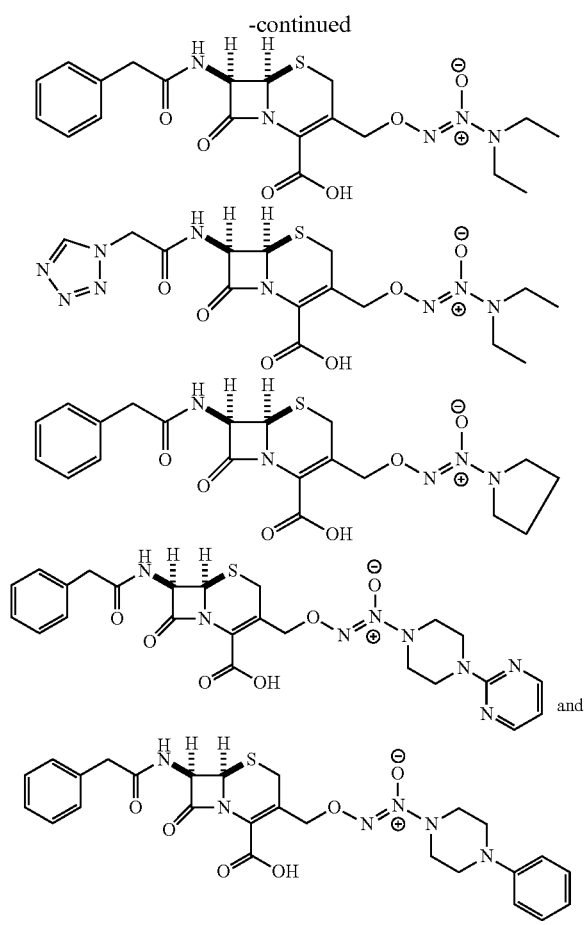

including salts thereof.

4. A compound according to claim 1 further comprising an antibiotic compound attached via the $R_2$ and/or $R_3$ substituent.

5. A compound according to claim 4 wherein the antibiotic is ciprofloxacin or N-desmethyl levofloxacin.

6. A composition for promoting the dispersal of microorganisms from a biofilm or inhibiting the formation and/or development of biofilms, the composition comprising a compound according to claim 1.

7. A composition according to claim 6 further comprising one or more additional antibiotics or antimicrobial agents.

8. A method for promoting dispersal of microorganisms from a biofilm, or for inhibiting biofilm formation and/or development, or for treating or preventing a biofilm-associated infection, disease or disorder in a subject, wherein the infection is caused by a microorganism capable of forming a biofilm, the method comprising exposing the biofilm or biofilm-forming microorganisms, or subject to an effective amount of a compound according to claim 1.

9. A method according to claim 8 wherein the compound is coated, impregnated or otherwise contacted with a surface or interface susceptible to biofilm formation.

10. A method according to claim 9 wherein the surface is a surface of an implantable medical device, prosthesis or medical or surgical equipment.

11. A method according to claim 8 wherein the biofilm-forming microorganisms express a β-lactamase or a transpeptidase.

12. A method according to claim 11 wherein the β-lactamase is a penicillinase.

13. A method according to claim 8 wherein the biofilm or biofilm-forming microorganisms are exposed to a β-lactam antibiotic prior to or concomitant with exposure to the compound.

14. A method according to claim 8 wherein the biofilm forms on a bodily surface of the subject, internal or external to the subject, and exposure of the biofilm or biofilm-forming microorganisms to the compound is via administration of the compound to the subject.

15. A method according to claim 8 wherein promoting dispersal of microorganisms from a biofilm or preventing formation of biofilms comprises inducing differentiation events in microorganisms within biofilms which lead to dispersal or comprises preventing induction of differentiation events in microorganisms which lead to biofilm formation; or
  wherein promoting dispersal of microorganisms from a biofilm or preventing formation of biofilms comprises increasing the sensitivity of a microorganism to antimicrobial agents.

16. A method according to claim 8 wherein the biofilm or biofilm-forming microorganisms are exposed to an effective amount of the compound such that the concentration of the nitric oxide donor or nitric oxide released and thus exposed to the biofilm or microorganisms is non-toxic to the environment or to the subject in which the biofilm or microrgansims are found.

17. A method according to claim 8 wherein the biofilm is on or within the body of the subject and is associated with a disease or disorder suffered by the subject.

18. A method according to claim 17 wherein the disease or disorder is selected from cystic fibrosis, bacterial endocarditis, otitis media, Legionnaire's disease, tuberculosis and kidney stones.

* * * * *